(12) United States Patent
Clark et al.

(10) Patent No.: US 11,954,146 B2
(45) Date of Patent: **\*Apr. 9, 2024**

(54) GEOGRAPHIC POPULATION HEALTH INFORMATION SYSTEM

(71) Applicant: Blue Cross and Blue Shield Association, Chicago, IL (US)

(72) Inventors: Teresa Nguyen Clark, Lake Forest, IL (US); Michael Steven Weinberg, Berwyn, IL (US); Carlos Ricardo Villarreal, Bloomington, IN (US); Nathania Hau, Chicago, IL (US); Jelani Akil McLean, Chicago, IL (US); Abigail Berube, Chicago, IL (US); Trent Tyrone Haywood, Lewisville, TX (US)

(73) Assignee: Blue Cross and Blue Shield Association, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,278

(22) Filed: Jan. 6, 2023

(65) Prior Publication Data

US 2023/0161813 A1 May 25, 2023

Related U.S. Application Data

(63) Continuation of application No. 17/333,167, filed on May 28, 2021, now Pat. No. 11,550,842, which is a (Continued)

(51) Int. Cl.
*G06F 16/58* (2019.01)
*G06F 3/0482* (2013.01)
(Continued)

(52) U.S. Cl.
CPC ........ *G06F 16/5866* (2019.01); *G06F 3/0482* (2013.01); *G06F 16/29* (2019.01);
(Continued)

(58) Field of Classification Search
CPC ....... G06T 17/20; G06T 17/205; G06T 15/04; G06T 11/40; G06T 15/005; G06T 3/40;
(Continued)

(56) References Cited

U.S. PATENT DOCUMENTS 5,734,709 A 3/1998 Dewitt et al.
6,307,573 B1 10/2001 Barros
(Continued)

FOREIGN PATENT DOCUMENTS

CN 304857845 10/2018
WO WO2016067299 5/2016

OTHER PUBLICATIONS

ArcGIS, "Interactive Data Visualization for Spatial Analysis," YouTube, published Jun. 7, 2017, Retrieved from website https://www.youtube.com/watch?v=iPPGfEA2s2M, 2 pp.
(Continued)

*Primary Examiner* — Todd Buttram
(74) *Attorney, Agent, or Firm* — Neal, Gerber & Eisenberg LLP

(57) ABSTRACT

A method and system for providing a data analysis in the form of a customized geographic visualization on a graphical user interface (GUI) on a remote client computing device using only a web browser on the remote client device. The system receives a user's selected data analysis to be performed by the system for display on the remote client device. The system verifies the data access permissions of the user to render a data analysis solution customized to that particular user, and automatically prevents that user from gaining access to data analysis solutions to which that user
(Continued)

is prohibited. The system is configured to respond to the user's data analysis request, perform the necessary computations on the server side on the fly, and send a dataset interpretable by the client device's web browser for display on the client device or on a device associated with the client device.

20 Claims, 51 Drawing Sheets

Related U.S. Application Data continuation of application No. 16/882,406, filed on May 22, 2020, now Pat. No. 11,023,563, which is a continuation of application No. 15/336,466, filed on Oct. 27, 2016, now Pat. No. 10,664,570.

(60) Provisional application No. 62/247,190, filed on Oct. 27, 2015.

(51) Int. Cl.
| | | |
|---|---|---|
| *G06F 16/29* | (2019.01) | |
| *G06F 16/951* | (2019.01) | |
| *G06F 21/62* | (2013.01) | |
| *G16H 40/63* | (2018.01) | |
| *G16H 50/80* | (2018.01) | |
| *G06T 3/40* | (2006.01) | |
| *G06T 11/00* | (2006.01) | |
| *H04L 67/01* | (2022.01) | |

(52) U.S. Cl.
CPC ........ *G06F 16/951* (2019.01); *G06F 21/6245* (2013.01); *G16H 40/63* (2018.01); *G16H 50/80* (2018.01); *G06F 2203/04806* (2013.01); *G06T 3/40* (2013.01); *G06T 11/001* (2013.01); *G06T 2207/20112* (2013.01); *H04L 67/01* (2022.05)

(58) Field of Classification Search
CPC .... G06F 3/0481; G06F 3/0485; G06F 3/0486; G06F 3/04855
See application file for complete search history.

(56) References Cited

U.S. PATENT DOCUMENTS

| | | |
|---|---|---|
| 6,389,355 B1 | 5/2002 | Gibbs et al. |
| 6,879,836 B2 | 4/2005 | Nakamoto et al. |
| 7,158,878 B2 | 1/2007 | Rasmussen et al. |
| 7,207,012 B1 | 4/2007 | House et al. |
| D543,551 S | 5/2007 | Blencowe |
| D553,627 S | 10/2007 | Blencowe |
| D553,631 S | 10/2007 | Blencowe |
| D562,836 S | 2/2008 | Blencowe |
| D566,716 S | 4/2008 | Rasmussen et al. |
| D586,361 S | 2/2009 | Horowitz et al. |
| D586,362 S | 2/2009 | Horowitz et al. |
| D586,363 S | 2/2009 | Horowitz et al. |
| 7,509,579 B1 | 3/2009 | House et al. |
| D595,304 S | 6/2009 | Rasmussen et al. |
| D621,846 S | 8/2010 | Rasmussen et al. |
| D636,398 S | 4/2011 | Matas |
| 8,164,599 B1 | 4/2012 | Kadous et al. |
| D671,953 S | 12/2012 | Lee et al. |
| D671,954 S | 12/2012 | Wojcik et al. |
| D674,403 S | 1/2013 | Pearcy et al. |
| 8,761,491 B2 | 6/2014 | Chen et al. |
| D731,510 S | 6/2015 | Kiruluta et al. |
| D740,842 S | 10/2015 | Liu et al. |
| D755,195 S | 5/2016 | Meyers et al. |
| D757,053 S | 5/2016 | Nadiadi et al. |
| D765,107 S | 8/2016 | Heinrich et al. |
| D765,673 S | 9/2016 | Leabman |
| D767,599 S | 9/2016 | Le Pors et al. |
| D769,270 S | 10/2016 | Hazam et al. |
| D781,884 S | 3/2017 | Parmar et al. |
| D808,980 S | 1/2018 | Hazam et al. |
| D814,494 S | 4/2018 | Stiansen |
| D818,474 S | 5/2018 | Kato et al. |
| D845,973 S | 4/2019 | Jaycobs |
| D857,735 S | 8/2019 | Ferrante et al. |
| D861,705 S | 10/2019 | Inose et al. |
| D871,427 S | 12/2019 | Clark et al. |
| D879,819 S | 3/2020 | Bhardwaj et al. |
| 10,609,114 B1 | 3/2020 | Bicket et al. |
| 10,664,570 B1* | 5/2020 | Clark .................. G06F 21/6245 |
| 10,783,686 B2 | 9/2020 | Cervelli et al. |
| D921,005 S | 6/2021 | Rowlett |
| 11,023,563 B2* | 6/2021 | Clark .................. G06F 16/5866 |
| D926,209 S | 7/2021 | Wu et al. |
| D930,024 S | 9/2021 | Stein |
| D936,081 S | 11/2021 | Rubin et al. |
| 11,550,842 B2* | 1/2023 | Clark .................... G06F 3/0482 |
| 2002/0145620 A1 | 10/2002 | Smith et al. |
| 2004/0021584 A1 | 2/2004 | Hartz et al. |
| 2004/0243299 A1 | 12/2004 | Scaer et al. |
| 2005/0034075 A1 | 2/2005 | Riegelman et al. |
| 2006/0105775 A1 | 5/2006 | Von Kaenel et al. |
| 2007/0094045 A1 | 4/2007 | Cobbs et al. |
| 2007/0198299 A1* | 8/2007 | Puckrein ................ G06Q 30/02 702/19 |
| 2008/0040028 A1 | 2/2008 | Crump |
| 2008/0077474 A1* | 3/2008 | Dumas ............... G06Q 30/0201 705/7.29 |
| 2008/0082572 A1 | 4/2008 | Ballard et al. |
| 2008/0140718 A1 | 6/2008 | Evans et al. |
| 2008/0168396 A1 | 7/2008 | Matas et al. |
| 2008/0208443 A1 | 8/2008 | Massie et al. |
| 2009/0273613 A1* | 11/2009 | Subherwal ............ G06T 3/4038 345/473 |
| 2011/0087503 A1* | 4/2011 | Desai ..................... G16H 10/20 705/3 |
| 2011/0173045 A1 | 7/2011 | Jaine |
| 2011/0271192 A1 | 11/2011 | Jones et al. |
| 2011/0271207 A1 | 11/2011 | Jones et al. |
| 2011/0289010 A1 | 11/2011 | Rankin, Jr. et al. |
| 2013/0219334 A1 | 8/2013 | Campbell et al. |
| 2013/0339891 A1 | 12/2013 | Blumenberg et al. |
| 2013/0346873 A1 | 12/2013 | Vasudev et al. |
| 2014/0026088 A1 | 1/2014 | Monte |
| 2014/0108374 A1 | 4/2014 | Dodge et al. |
| 2014/0278306 A1 | 9/2014 | Taghavi et al. |
| 2015/0193595 A1* | 7/2015 | McNamara .......... A61B 5/0205 705/2 |
| 2015/0278369 A1 | 10/2015 | Wong et al. |
| 2015/0371161 A1* | 12/2015 | Mueller ............... G06Q 30/018 705/7.12 |
| 2015/0371421 A1 | 12/2015 | Hadfield |
| 2016/0055420 A1 | 2/2016 | Karanam et al. |
| 2016/0180386 A1 | 6/2016 | Konig |
| 2016/0203628 A1* | 7/2016 | Okumura ............... G06T 1/0007 715/733 |
| 2016/0299639 A1 | 10/2016 | Adams et al. |
| 2016/0314615 A1 | 10/2016 | Kim |
| 2016/0350507 A1* | 12/2016 | Guerin .................... G16Z 99/00 |
| 2017/0212992 A1 | 7/2017 | Pah et al. |
| 2017/0322710 A1 | 11/2017 | Cockburn et al. |
| 2017/0351833 A1 | 12/2017 | Cahan et al. |
| 2018/0053326 A1 | 2/2018 | Ingrassia et al. |
| 2019/0380020 A1 | 12/2019 | Pellegrini et al. |
| 2019/0392019 A1 | 12/2019 | Brannon et al. |
| 2020/0057555 A1 | 2/2020 | Walkin et al. |
| 2020/0286619 A1* | 9/2020 | Clark ..................... G06F 21/31 |

OTHER PUBLICATIONS

Bresnick, "Using Visual Analytics, Big Data Dashboards for Healthcare Insights," Health IT Analytics, Sep. 18, 2017, 14 pp.

(56) References Cited

OTHER PUBLICATIONS

Melnykov, "Industrial Analytics Senso Map Overview Dashboard," Dribble, Dec. 8, 2016, 4 pp.

* cited by examiner

FIG. 7

GEOGRAPHIC POPULATION HEALTH INFORMATION SYSTEM

CROSS-REFERENCE TO RELATED APPLICATION

This application is a continuation of U.S. Nonprovisional application Ser. No. 17/333,167, filed May 28, 2021, which is a continuation of U.S. Nonprovisional application Ser. No. 16/882,406, filed May 22, 2020, which issued as U.S. Pat. No. 11,023,563 on Jun. 1, 2021, which is a continuation of U.S. Nonprovisional application Ser. No. 15/336,466, filed Oct. 27, 2016, which issued as U.S. Pat. No. 10,664,570 on May 26, 2020, which claims the benefit of U.S. Provisional Application No. 62/247,190, filed Oct. 27, 2015, all of which are incorporated herein by reference in their entirety.

BACKGROUND

This application relates generally to the field of healthcare data analysis, and more specifically to systems and methods for displaying geographic population health information.

Existing systems for analyzing population healthcare data based on population distribution, disease state, and access to options to improve health requires software residing on the user's computing device or system to store, compute, manipulate, integrate multiple data sources, and display the results of massive datasets. Most likely, such software residing on the user's computing device or system includes database management software to perform data management functions. As new datasets are made available, software on the user's computing device or system requires updates to enable access to the new datasets as such software updates are released. In addition, to render a spatial distribution on a user's computing device or system, existing methods and systems require software on the user's computing device or system to facilitate integration of the disparate data assets with geographical information system software to produce a composite rendering on the graphical user interface.

The proposed software and associated system of the instant disclosure addresses these and other limitations of existing systems by using a client device's web browser to display geographical population health information data that the system collects, assembles, and preformats from disparate data sources for on-demand, dynamic, interactive display in the web browser.

SUMMARY

A geographic population health information system is disclosed, comprising: (a) a map server configured to receive client identification information from a client device, the map server connected to a custom geographic data selection manager which is connected to a geo-spatial database server, and (b) a web server configured to receive client user ID information, the web server connected to a user security tabular data assessor which is connected to a custom data selection manager, wherein the custom data selection manager is connected to a plurality of databases, wherein the geographic population information system is configured to asynchronously match the data from the geo-spatial database server with data from the plurality of databases so as to render a user customized, dynamic visualization of healthcare data in a web browser of the client device connected to the map server and the web server.

A geographic population health information system is disclosed comprising: (i) one or more first servers configured to: receive a request from a client system for a geographical area and a desired segmenting of the geographical area; command a geo-spatial database to deliver one or more shapefiles based on the geographical area and the desired segmenting of the geographical area, the one or more shapefiles including polygons with vertices having coordinates located within the outer boundaries; serve the shapefiles to the client system; (ii) the client system, which is configured to: receive one or more sets of health data after receiving the served shapefiles; match each portion of the received health data to at least one of the served shapefiles; generate shading instructions for at least some of the polygons of the one or more shapefiles based on the matched health data; produce a plurality of image tiles based on the served shapefiles and the shading instructions; arrange and display the plurality of image tiles on a graphical user interface of the client system.

The geographical area of the request may comprise coordinates of a center of the geographical area and a zoom level.

The one or more servers may be configured to command the geo-spatial database to deliver the one or more shapefiles based on the center of the geographical area and the zoom level.

The zoom level may correspond to a current zoom level of the graphical user interface of the client system.

The system may further comprise the one or more second servers, the one or more second servers storing hypertension prevalence data for each of a plurality of zip codes.

The client system may be configured to receive the hypertension prevalence data as the one or more sets of health data and generate the shading instructions for the at least some of the polygons based on the received hypertension prevalence data.

The one or more second servers may be configured to serve at least some of the one or more sets of health data to the client system in a tabular format.

The client system may be configured to display the at least some of the one or more sets of health data in the tabular format in response to a user selection.

The client system may be configured to map a user selection of a pixel of at least one of the one or more image tiles to the portion the received one or more sets of health data matched with a polygon encompassing the pixel.

The client system may be configured to display the matched portion of the received one or more sets of health data in tabular form in response to the user selection of the pixel.

A geographic population health information system is disclosed comprising: one or more first servers configured to: receive a request from a client system for a layer including (a) one or more sets of health data (b) a geographical area, and (c) a desired segmenting of the geographical area; command a geo-spatial database to deliver one or more shapefiles based on the geographical area and the desired segmenting of the geographical area, the one or more shapefiles including polygons with vertices having coordinates located within the outer boundaries; receive the one or more sets of health data from one or more second servers; match the each portion of the one or more sets of health data with at least one of the polygons; generate shading instructions for at least some of the polygons of the one or more shapefiles based on the received one or more sets of health data matched with the at least some of the polygons; produce a plurality of image tiles based on the shapefiles and the shading instructions; serve the plurality of image tiles to the client system.

The geographical area of the request may comprise coordinates of a center of the geographical area and a zoom level.

The one or more servers may be configured to command the geo-spatial database to deliver the one or more shapefiles based on the center of the geographical area and the zoom level.

The zoom level may correspond to a current zoom level of a graphical user interface of the client system.

The system may further comprise the one or more second servers, the one or more second servers storing hypertension prevalence data for each of a plurality of zip codes.

The one or more first servers may be configured to receive the hypertension prevalence data as the one or more sets of health data and generate the shading instructions for the at least some of the polygons based on the received hypertension prevalence data.

The one or more first servers may be configured to serve at least some of the one or more sets of health data to the client system in a tabular format.

The system may further comprise the client system, which is configured to display the at least some of the one or more sets of health data in the tabular format in response to a user selection.

The system may further comprise the client system, which is configured to assemble and arrange the plurality of image tiles received from the one or more first servers in an array of image tiles.

The one or more first servers may be configured to serve tile arrangement instructions to the client system along with the plurality of image tiles and the client system is configured to arrange the plurality of image tiles into the array based on the tile arrangement instructions.

BRIEF DESCRIPTION OF THE DRAWINGS

FIGS. 5 to 52 illustrate various embodiments of geographic population health information data displayed on a graphical user interface according to various constraints and filters.

DETAILED DESCRIPTION

Although the figures and the instant disclosure describe one or more embodiments, one of ordinary skill in the art would appreciate that the teachings of the instant disclosure would not be limited to these embodiments. Various embodiments of the instant disclosure relate to integrating, analyzing, and visualizing geographic, population-based, health data on computer displays associated with one or more remote client computing devices without requiring client-side software on the client device other than a web browser. The system herein disclosed eliminates the need for enterprise-wide software installations on client devices, and of the need to modify client-side computing devices to access the requested data. The system herein disclosed also avoids data capacity limitations that would prevent the client computing device from rendering the requested topographical data. The system provides users with on-demand, user customized data analysis through a server system that may include a cloud-based server system.

Figure 1:
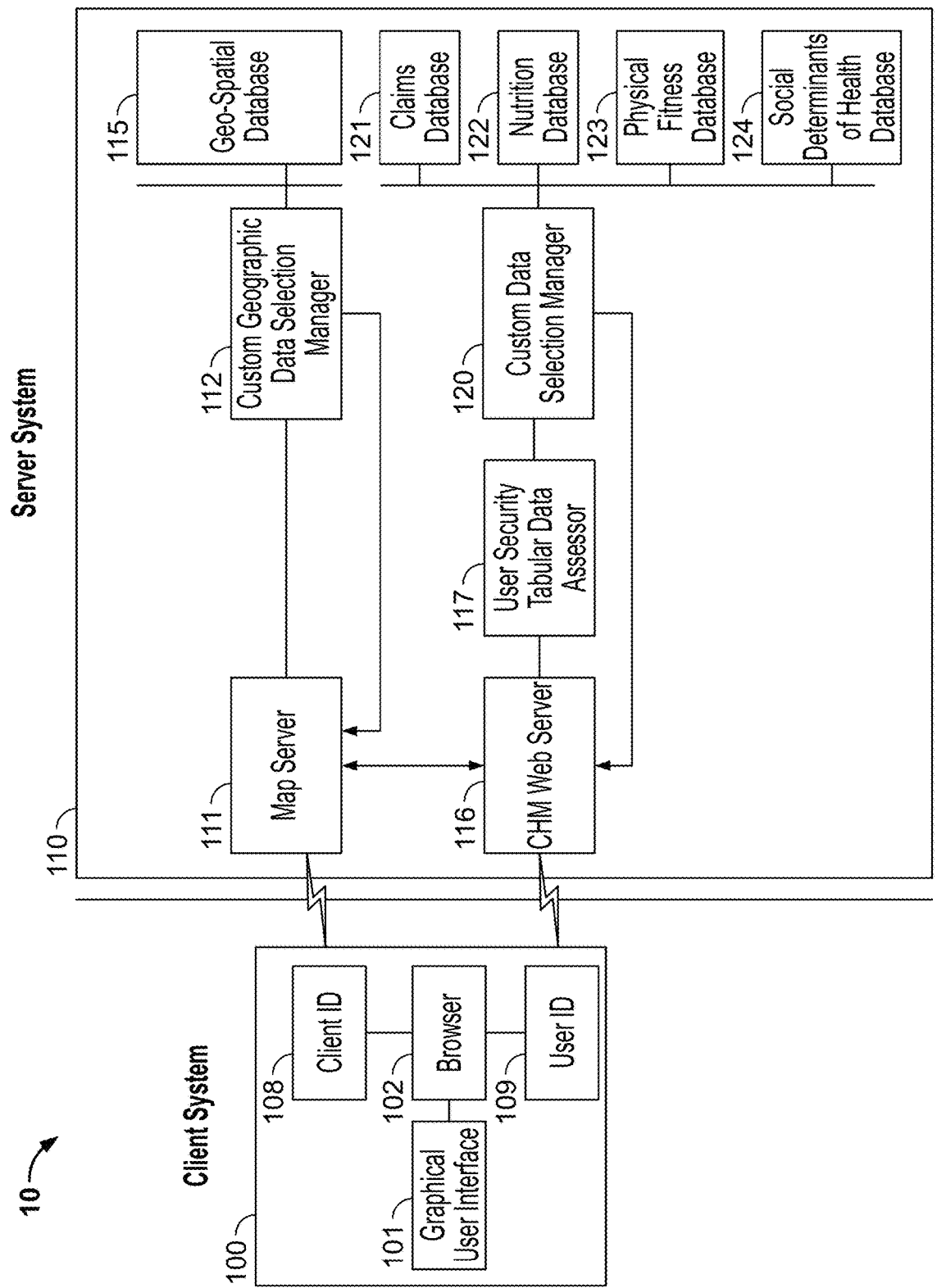
FIG. 1 illustrates one embodiment of a system architecture of the instant disclosure in block diagram form.

Turning now to the drawings wherein like reference numerals refer to like elements, FIG. 1 shows an illustration of one embodiment of a system architecture that solves the problems associated with existing systems. In this embodiment, system 10 includes server system 110 hosting application software that responds to requests from client system 100.

Figure 3:
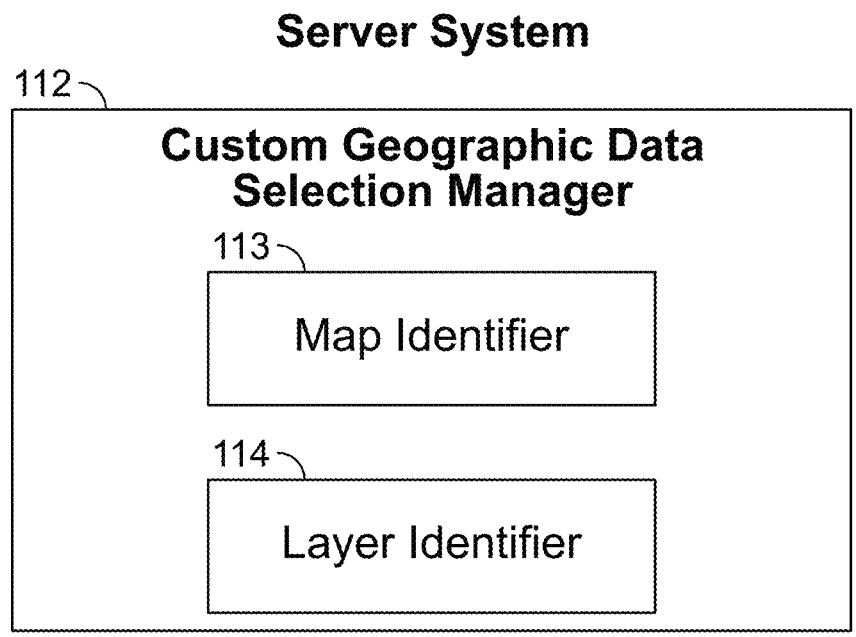
FIG. 3 illustrates a detailed block diagram of the customer geographic data selection manager shown in FIG. 1.
Figure 4:
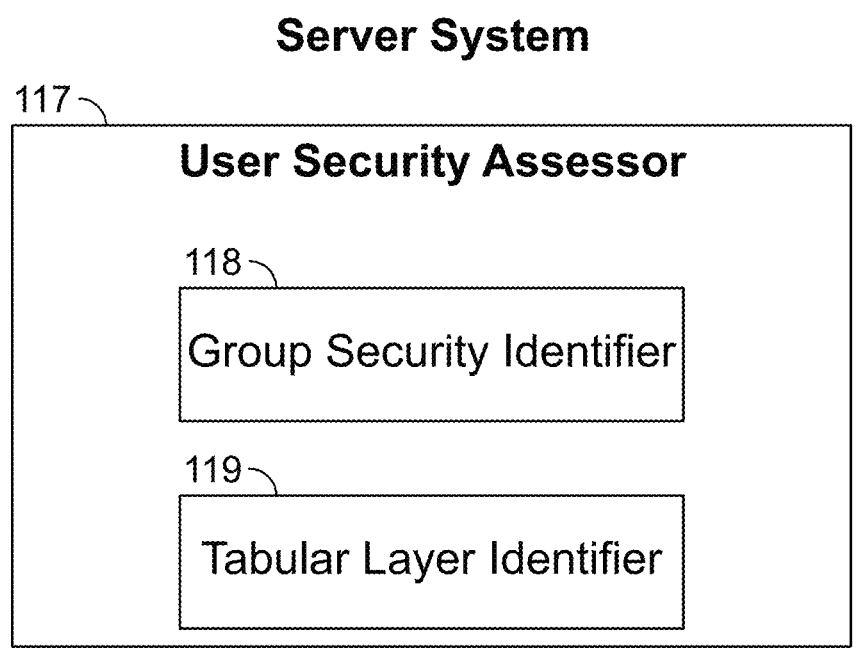
FIG. 4 illustrates a detailed block diagram of the user security tabular data assessor shown in FIG. 1.
Figure 5:
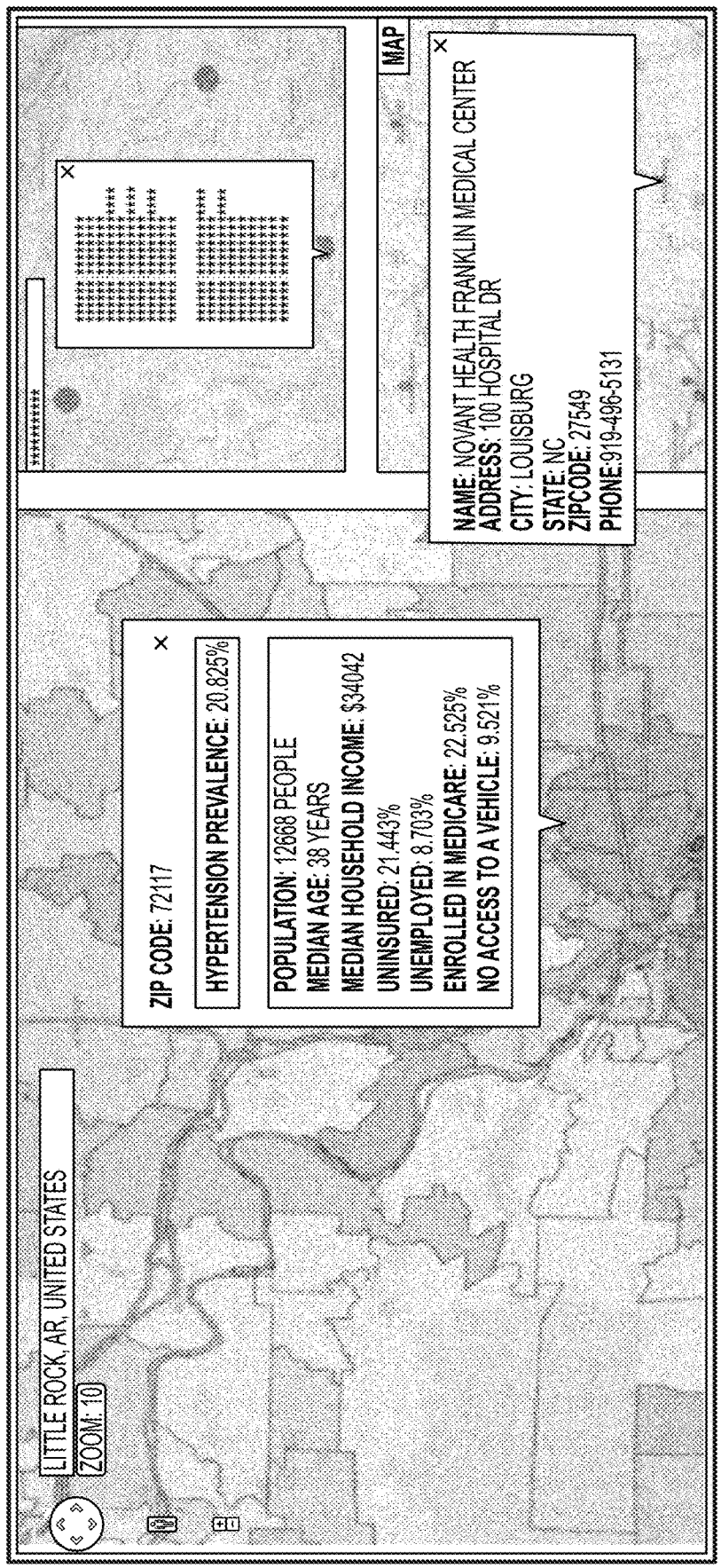
Figure 6:
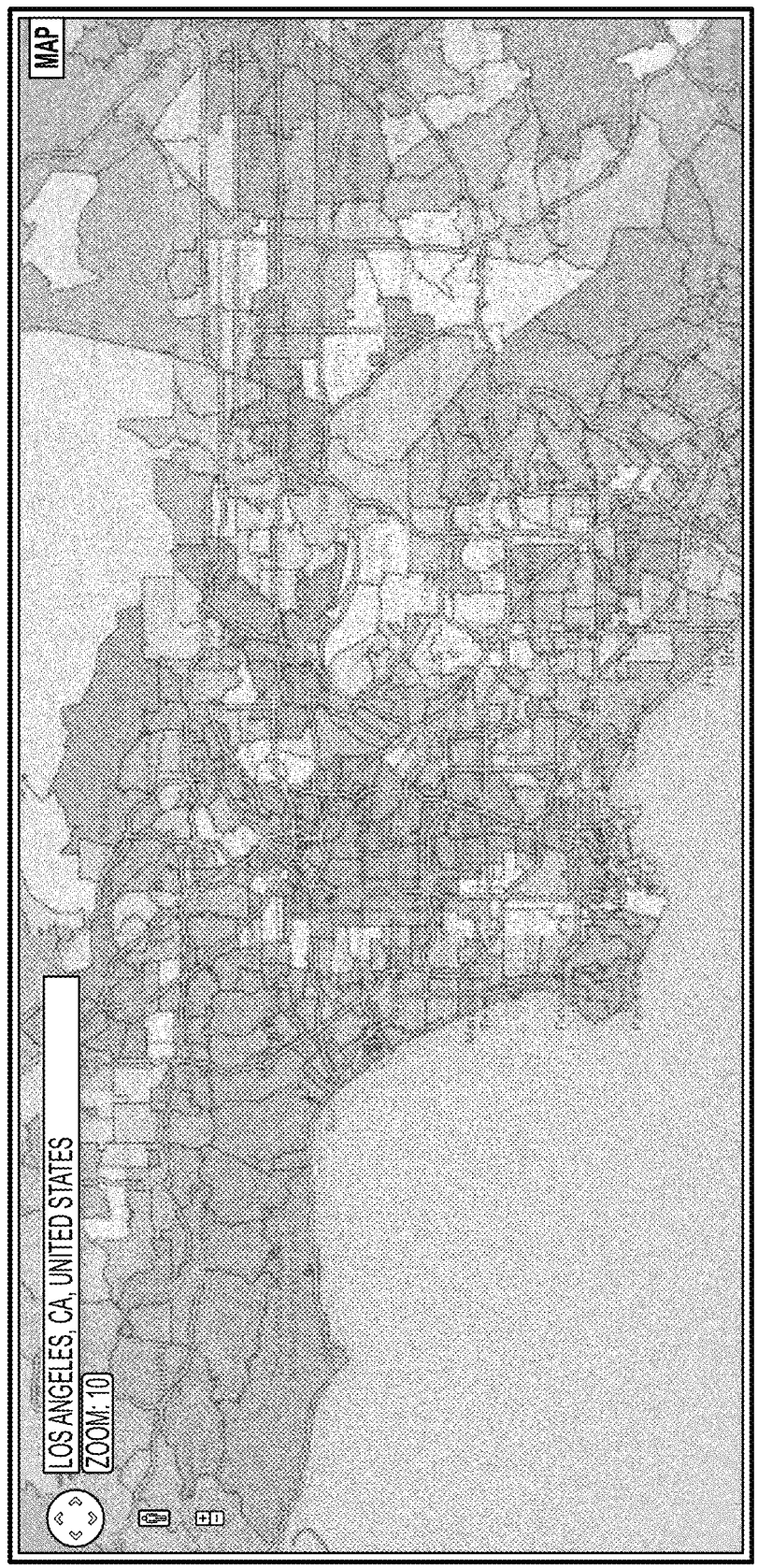

Server system 110 may include any web server such as a cloud-based server or a dedicated server system. Server system 110 in this embodiment includes various hardware and software elements, including map server 111, custom geographic data selection manager 112, community health management (CHM) web server 116, user security tabular data assessor 117, and custom data selection manager 120. Referring to FIG. 3, custom geographic data selection manager 112 may also include map identifier 113 and layer identifier 114. Referring to FIG. 4, user security tabular data assessor 117 may include group security identifier 118 and tabular layer identifier 119.

Server system 110 in this embodiment also includes connections to various databases, including geo-spatial database 115, claims database 121, nutrition database 122, physical fitness database 123, and social determinants of health database 124. One of ordinary skill would appreciate that in other embodiments, server system 110 may implement multiple other servers and databases or fewer than what is shown in FIG. 1. Server system 110 may also include one or more computer processors, one or more data memory storage elements, one or more input/output buses and data ports to enable the communication of data to and from server system 110 via one or more wired, wireless, wifi, cellular, and satellite networks via the Internet, the world wide web, or any other communications protocol.

Geo-spatial database 115 may include and store a plurality of shapefiles. Each shapefile may include one or more points or vertices, one or more lines connecting at least two vertices, and/or one or more polygons connecting at least three vertices. Geo-spatial database 115 may include and store at least one shapefile including a plurality of polygons, each corresponding to a respective zip code. Claims database 121 may include geolocation data, organization data, and bar code scan data files. Nutrition database 122 may include healthcare administrative claims data. Physical fitness database 123 may include geological data and image data of impervious surfaces. Social determinants of health database 124 may include alphanumeric descriptive data.

Figure 2:
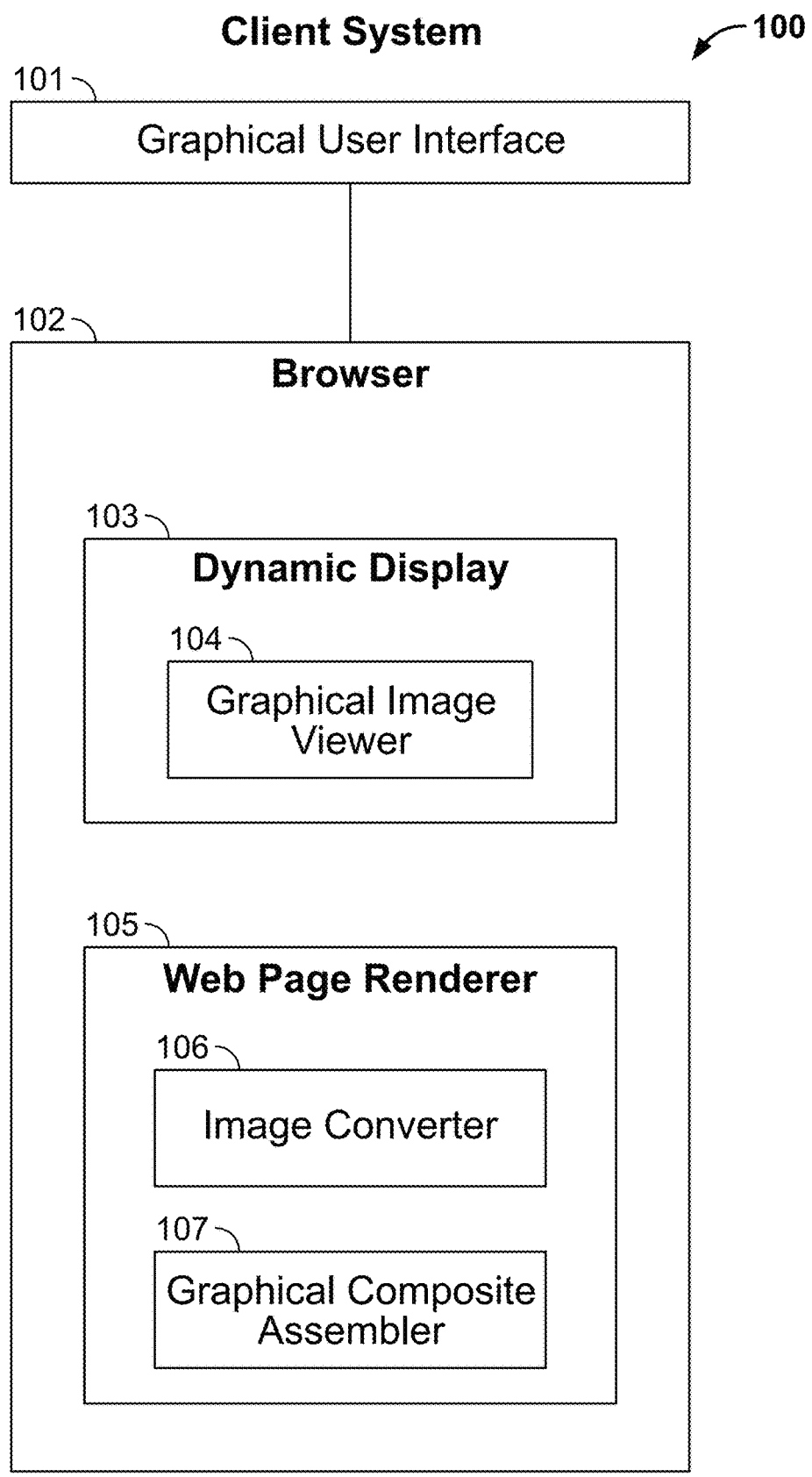
FIG. 2 illustrates a detailed block diagram of the client system shown in FIG. 1.

Client system 100 may include graphical user interface (GUI) 101, such as a display, and Internet web browser 102, such as Internet Explorer, Safari, Firefox, or Google Chrome, to name a few. Client system 100 may also include client ID 108 representing a unique identifier that may be registered with server system 110 so that server system 110 recognizes and returns requested data back to the same client device. Referring to FIG. 2, web browser 102 of client system 100 may include dynamic display 103 including graphical image viewer 104, and web page renderer 105 including image converter 106 and graphical composite assembler 107.

In one embodiment, map server 111 authenticates client ID 108 after receiving a service token from web browser 102. The custom geographic data selection manager 112 receives the client input/selection (i.e. query) for a layer and retrieves, via layer identifier 114, one or more shapefiles (or portions thereof) from geo-spatial database 115. The one or more shapefiles (or portions thereof) retrieved from the geo-spatial database 115 may be referred to as the appropriate shapefiles. To retrieve the appropriate shapefiles, map identifier 113 of custom geographic data selection manager 112 uses a map identification routine to select the requested map, and layer identifier 114 of geographic data selection manager 112 selects the appropriate layers from the selected map. The layers from the selected map include vertices files that are combined to form the shapefile. The selected shapefile is sent to the map server 111 as a response to the original request from the web browser 102.

The custom data selection manager 112 may further retrieve, via map identifier 113, one or more reference shapefiles from an external database. The one or more reference shapefiles may be used to build an underlying reference map upon which the appropriate shapefiles are overlaid.

Figure 7:
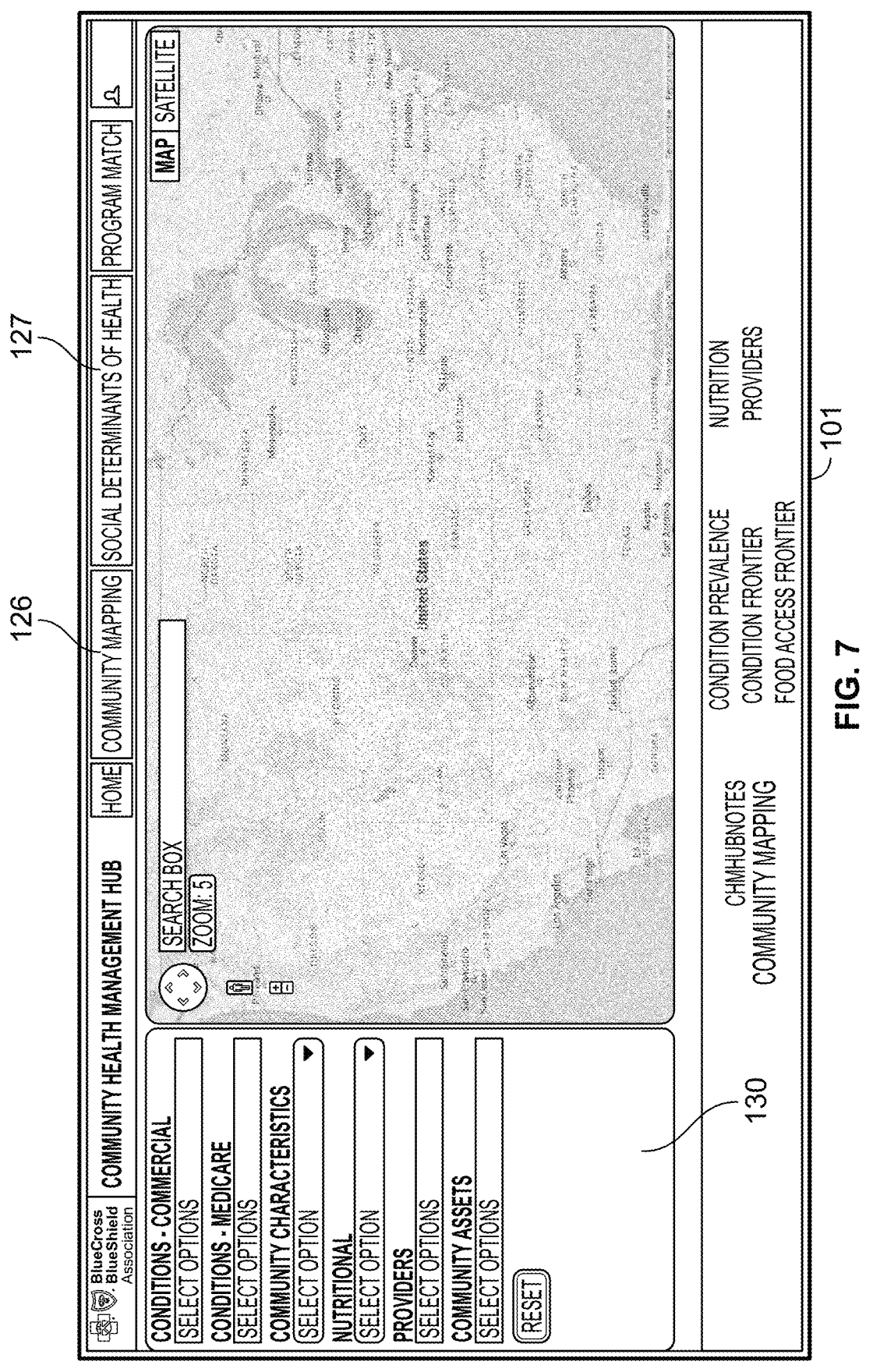
Figure 8:
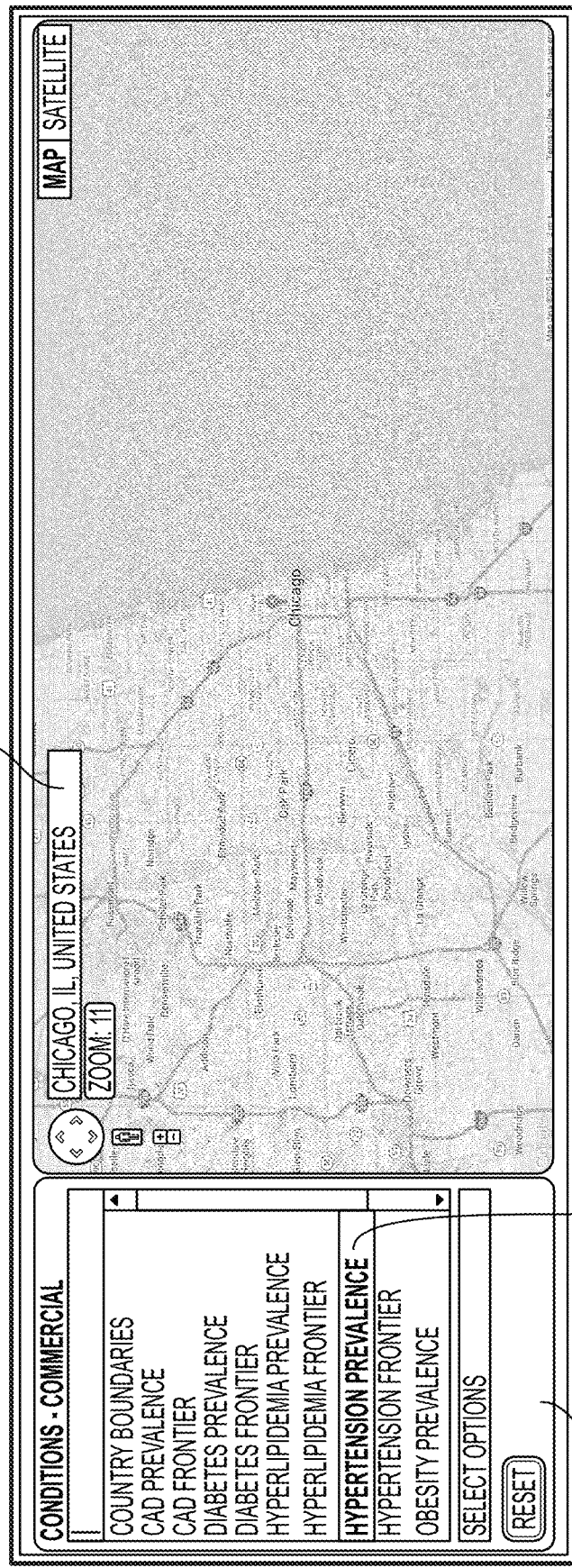

To retrieve the appropriate shapefiles and/or the reference shapefiles, layer identifier 114 and/or map identifier 113 of custom geographic data selection manager 112 may determine outer coordinates of a displayed portion of the reference map. For example, the displayed portion of the reference map in FIG. 7 is almost the entire United States and small portions of the Pacific and Atlantic Oceans, whereas the displayed portion of the reference map in FIG. 8 is Chicago. According to one embodiment, map identifier 113 retrieves the reference shapefiles from the external server before the layer identifier 114 retrieves the appropriate shapefiles from the geo-spatial database 115.

To determine the outer coordinates layer identifier 114 may determine (a) a zoom level of a reference map currently displayed on GUI 101 and (b) a center of the reference map currently displayed on GUI 101. Layer identifier 114 may learn the zoom level of the reference map by querying the client system 100. Alternatively, layer identifier 114 may have previously learned the zoom level of the reference map in order to retrieve appropriate reference shapefiles of the reference map. Based on the zoom level and the center of the reference map, layer identifier 114 may determine outer coordinates of a displayed portion of the reference map. Alternatively or in addition, layer identifier 114 may determine the outer coordinates of the displayed portion of the reference map by determining outer-most vertices, lines, or polygons of reference shapefiles being used to render the displayed portion of the reference map.

Layer identifier 114 may determine which sets of shapefiles stored in the geo-spatial database 115 include the appropriate shapefiles based on a user selection of one or more layers on a drop-down menu displayed on GUI 101. For example, the geo-spatial database 115 may include (a) one set of one or more shapefiles representing zip codes of the United States, (b) one set of one or more shapefiles representing state lines of the United States, (c) one set of one or more shape files representing city boundaries of the United States. Layer identifier 114 may only retrieve shapefiles from the applicable sets of shapefiles. For example, if the user-selected layer is segmented according to zip code, but not according to city boundaries, then the layer identifier 114 may only retrieve shapefiles from sets (a) and/or (b), but not from set (c).

It should thus be appreciated that layer identifier 114 may determine the applicable sets of shapefiles of geo-spatial database 115 and that layer identifier 114 may further determine the appropriate portions of the applicable sets. Put differently, layer identifier 114 may retrieve the appropriate shapefiles from the one or more applicable sets of shapefiles. The appropriate shapefiles may include polygons having one or more vertices with coordinates falling within the displayed portion of the reference map, lines having one or more vertices with coordinates falling within the displayed portion of the reference map, and/or vertices with coordinates falling within the displayed portion of the reference map. The appropriate shapefiles may be sent to the map server 111 as a response to the original request from the web browser 102.

According to one embodiment, the map server 111 may serve the appropriate shapefiles (retrieved by the layer identifier 114) and/or the reference shapefiles (retrieved by the map identifier 113) to the client system 100. The graphical composite assembler 107 may receive the shapefiles from the map server 111 while waiting to receive the customized data from the CHM web server 116. Upon receiving the customized data, the graphical composite assembler 107 may match the appropriate shapefiles (but not the reference shapefiles) with the tabular data received from the CHM web server 116. The image converter 106 may render a series of image tiles or raster files having the polygons, lines, and/or vertices included in the reference shapefiles and the appropriate shapefiles. The polygons, lines, and/or vertices of the appropriate shapefiles may be overlaid on the polygons, lines, and/or vertices of the reference shapefiles and be shaded according to the tabular data received from the CHM web server 116. The graphical image viewer 104 may assemble the rendered image tiles or raster files into an array according to assembly instructions produced by the image converter 106. The reference shapefiles may be rendered according to instructions received from the external server.

According to another embodiment, the map server 111 may convert the appropriate shapefiles and the reference shapefiles into raster files or image tiles. Each raster file or image tile may include polygons from the appropriate shapefiles, shaded according to the health data received from the CHM web server 116 and polygons from the reference shapefiles, shaded according to instructions received from the external server. To perform the conversion, the map server 111 may fill in or shade each polygon included in the appropriate shapefiles based on tabular data received from the CHM web server 116. Put differently, the shading of each polygon of the appropriate shapefiles may be based on data retrieved from CHM Web Server 116. As in the above embodiment, the shaded polygons of the appropriate shapefiles are overlaid on the polygons of the reference shapefiles during rendering. The map server 111 may deliver the raster files or image tiles (which may be images of the shaded polygons of the appropriate shapefiles overlaid onto the polygons of the reference shapefiles), instead of the appropriate shapefiles and the reference shapefiles, to the client system 100. The size of each polygon may based, at least in part, on a zoom level of the GUI 101.

In one embodiment, graphical image viewer 104 is configured to display graphical images in various graphical file formats. Dynamic display 103 of graphical image viewer 104 responds to inputs, such as macros, to dynamically change the display of responsive data on the web browser 102 in accordance with a user's commands. The dynamic display 103, for example, is configured to enable a user to move or pan the image displayed in web browser 102 and to zoom the image in or out. As the user moves, pans, and/or zooms, the dynamic display 103 may update or cause map identifier 113 to update the reference shapefiles being used to render the underlying reference map. As explained above, as the reference shapefiles used to display the underlying reference map are updated, the appropriate shapefiles may also be updated. As the user moves, pans, and/or zooms, the dynamic display 103 may update or cause map server 111 to serve (a) new shapefiles and/or (b) new raster files or image tiles. Web page renderer 105, or similar rendering engine, of web browser 102 ensures the image is properly displayed on the web page in the web browser 102. The web page renderer 105 combines various formats, including HTML and CSS. In one embodiment, the image is in HTML format and the navigation on the web page is performed via CSS.

The graphical composite assembler 107 may receive the data in an asynchronous manner. According to one embodiment, the graphical composite assembler 107 receives the appropriate shapefiles from the map server 111 and then instructs the image converter 106 to render the appropriate shapefiles according to health data later received from the CHM web server 116. According to another embodiment, the graphical composite assembler 107 receives the raster files or image tiles from map server 111 while waiting to receive customized data in tabular format from the CHM web server 116. Upon receiving the customized data in tabular format, the graphical composite assembler 107 may match the raster files or image tiles with the appropriate tabular data into a graphical composite. Image converter 106 may convert the assembled graphical composite into an image that can be viewed by the graphical image viewer 104.

Server system 110 is configured to receive entry by a user of server system 110 of a user ID 109 or other login credentials for ensuring that the user is provided access to only that information to which that user is allowed. Upon logging into the software hosted by server system 110, based upon the client identification and the login credentials of the user, server system 110 automatically modifies the menu of selectable options displayed on graphical user interface 101 of client system 100 for selection by the user. The user may then select from among one or more data analysis from the menu that are pre-customized for that user.

In operation, a user using a client device, such as a desktop computer, a laptop, a tablet, or a mobile device, connected to server system 110 would be provided by server system 110 with a login screen through which the user would enter the user's login credentials, such as login ID and password. Any variation of user authentication may be implemented by server system 110 as may be known in the art. Server system 110 is configured to provide a menu of data analyses from which the user may select. Such data analyses may include the preparation by server system 110 of a composite two-dimensional topographic map for display on the display of the user's device. Server system 110 may provide the user with various options or combination of elements from which the user may select that are associated with the requested data analysis.

Upon receipt of the user's request using web browser 102 connected to server system 110, in one embodiment, cloud-based map server 111 of server system 110 separately sends a request to CHM Web server 116. Map server 111 verifies the client ID 108 of the user's client computing device and sends the request to custom geographic data selection manager 112. Upon receipt of the request, geographic data selection manager 112 uses the map identifier 113 and/or the layer identifier 114 to select the appropriate shapefiles from the geo-spatial database 115 to render a map. Geographic data selection manager 112 sends the appropriate shapefiles to the map server 111. According to one embodiment, and as previously stated, the map server 111 serves the appropriate shapefiles to the client system 100. According to another embodiment, and as previously stated, the map server 111 serves the raster files or image tiles to web browser 102 of client system 100 for integration by web browser 102 into a map comprising a composite visualization of the requested data analysis.

Simultaneously, the CHM Web server 116 sends the request to the user security data assessor 117 to verify the user's group ID 109 and the data layer requested by the user. Upon verification that the user permissions are satisfied, the user request is received by the custom data selection manager 120. The custom data selection manager 120 queries the various databases 121,122,123,124 to retrieve the disparate data. Upon receipt of the disparate data components from the custom data selection manager 120, the CHM Web server 116 serves the data components to web browser 102 of client system 100 for integration by web browser 102 into a map comprising a composite visualization of the requested data analysis. In this way, server system 110 conducts the spatial and statistical analysis to match the user's request, and presents that data in a format that web browser 102 can interpret and assemble to graphically display the results.

Web browser 102 uses graphical composite assembler 107 to match the tabular data with (a) the shapefiles or (b) the raster files/image tiles to produce a composite graphic. The graphical composite assembler 107 may change the format of incoming data from the map server, which may be in the form of raster files, image files, and/or KML files. Image converter 106 converts the composite graphic into a Web page that can be viewed by graphical image viewer 104. Graphical image viewer 104 displays the Web page through graphical user interface 101, which may be any one of a number of displays associated with client system 100. Web browser 102 stores the layer information to prevent the need for server system 110 to retrieve the same layer if the user selects the same layer with new topographical elements.

Example: User Selection of Customized Data Analysis

In one example, a user wishes to conduct data analysis of a national account with employees across the 43,000 zip codes in the United States. In particular, the user desires to prioritize geographic areas where the account's employees have higher prevalence of hypertension in comparison to the prevalence of the general commercial population. Furthermore, the user seeks to limit the data analysis by controlling for social determinants of health. Finally, the user needs to identify local providers, community health centers, farmers markets, and social services that may be ideal partners to support population health management.

The user may log into the software hosted by server system 110 using a web browser 102 displayed on the client device of client system 100. The server system 110 presents a customized menu 130 on the web page displayed in the web browser 102 that is appropriate and/or customized for the user's user ID. The user may select the account and the hypertension prevalence layer. In addition, the user may select the layer that controls for the social determinants of health. Lastly, the user may select the local resources of interest.

The server system 110 automatically responds on the fly to the user's request by facilitating the collection and integration of data stored on disparate data sources, and preformats the results in a way that is interpretable and displayable by the user's web browser without any additional client-side software. The server system 110 pushes that formatted data to the user's web browser, which renders the account-specific information for hypertension prevalence in a composite visualization that allows the user to scan the map of the United States. The visualization renders an image of shape files for each zip code symbolized and/or represented in different colors that reflect zip codes with higher prevalence among the account population. Because the user controlled for social determinants of health, the visualization shades the shape files for the geographic areas controlled for by the user. The user may select or "click" on an area of the map and the shape file produces a pop-up display of the comparative data of the employee population to the general commercial population. The file size for the image could exceed 125 MB. By selecting providers and resources, the user can click on the displayed community assets to reveal the services provided by the local entity or hours of operation. Upon reviewing the services, the user can receive directions to the local entity by entering an address associated with the user's geographic location.

FIGS. 5-52 provide the results displayed in graphical user interface (GUI) 101 of Internet browser 102 of various exemplary searches on server system 110 that integrates community mapping data and social determinants of health data overlaid on a graphical map of the United States. In these embodiments, the data is configured for display by zip code. In other embodiments, the data may be displayed according to any other actual, artificial, or synthetic geographic or other boundary or grouping. For example, the data may be displayed by community, by city/town, by township, by county, by state, and by region, or any combination or subcombination of the foregoing.

Community mapping data may include data concerning medical condition prevalence, medical condition frontier, food access frontier, nutrition, population density centers, and health care providers, as shown by the references positioned on the bottom ribbon on FIG. 7 after selecting the tab 126 of graphical user interface (GUI) 101 of Internet browser 102.

Figure 20:
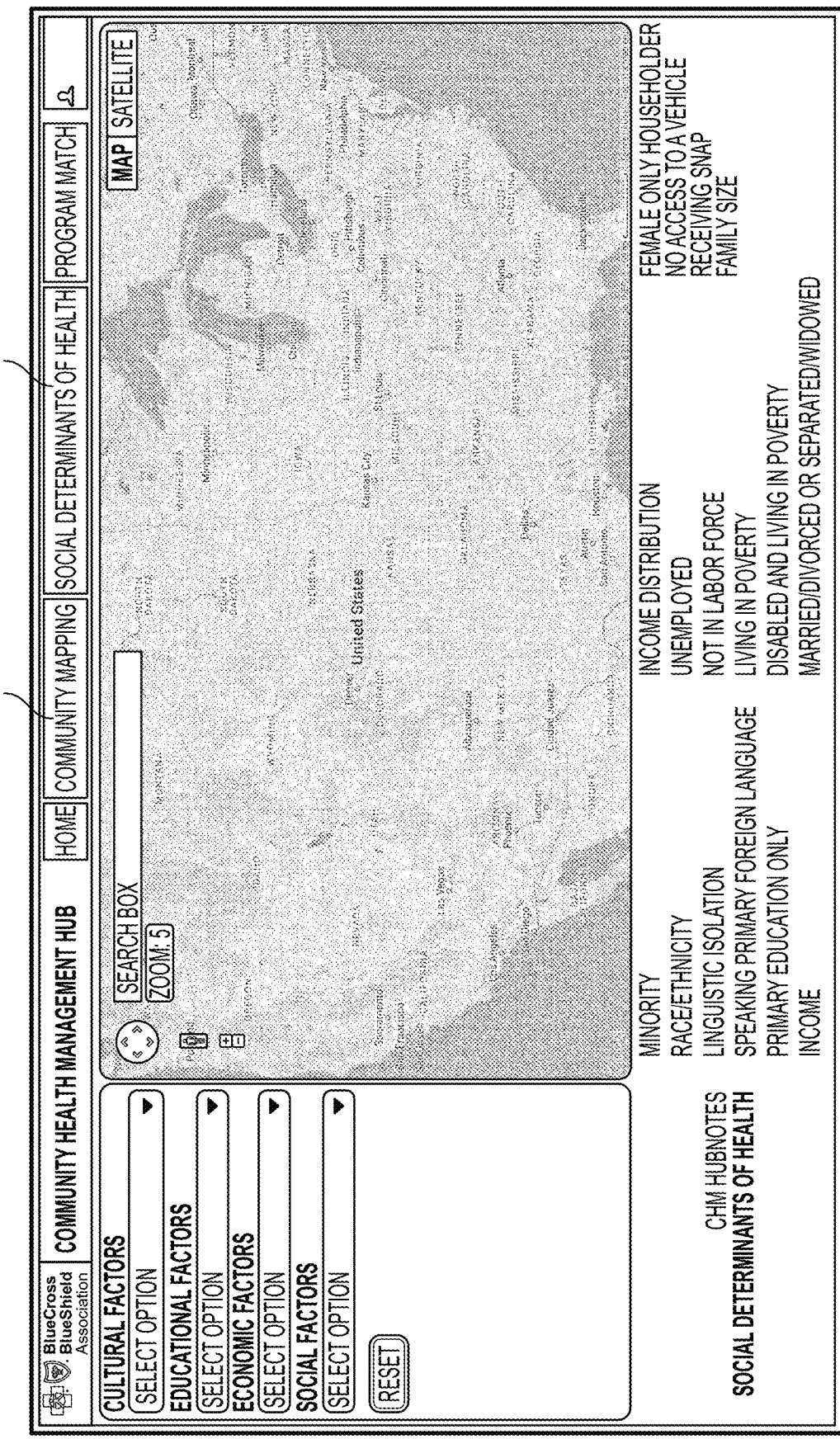

Social determinants of health data may include data concerning minority population prevalence, race/ethnicity prevalence, linguistic isolation prevalence, prevalence of a foreign language as the primary language, level of education, per capita income, income distribution, unemployment prevalence, prevalence of population not in the labor force, poverty prevalence, prevalence of disabled people living in poverty, marital status, prevalence of female only householders, prevalence of no access to a vehicle, prevalence of the population enrolled in Supplemental Nutritional Assistance Program (SNAP), and family size, as shown by the references positioned on the bottom ribbon on FIG. 20 after selecting tab 127 of graphical user interface (GUI) 101 of Internet browser 102. One of ordinary skill would appreciate that other community mapping data and/or social determinants of health data may be utilized.

Figure 9:
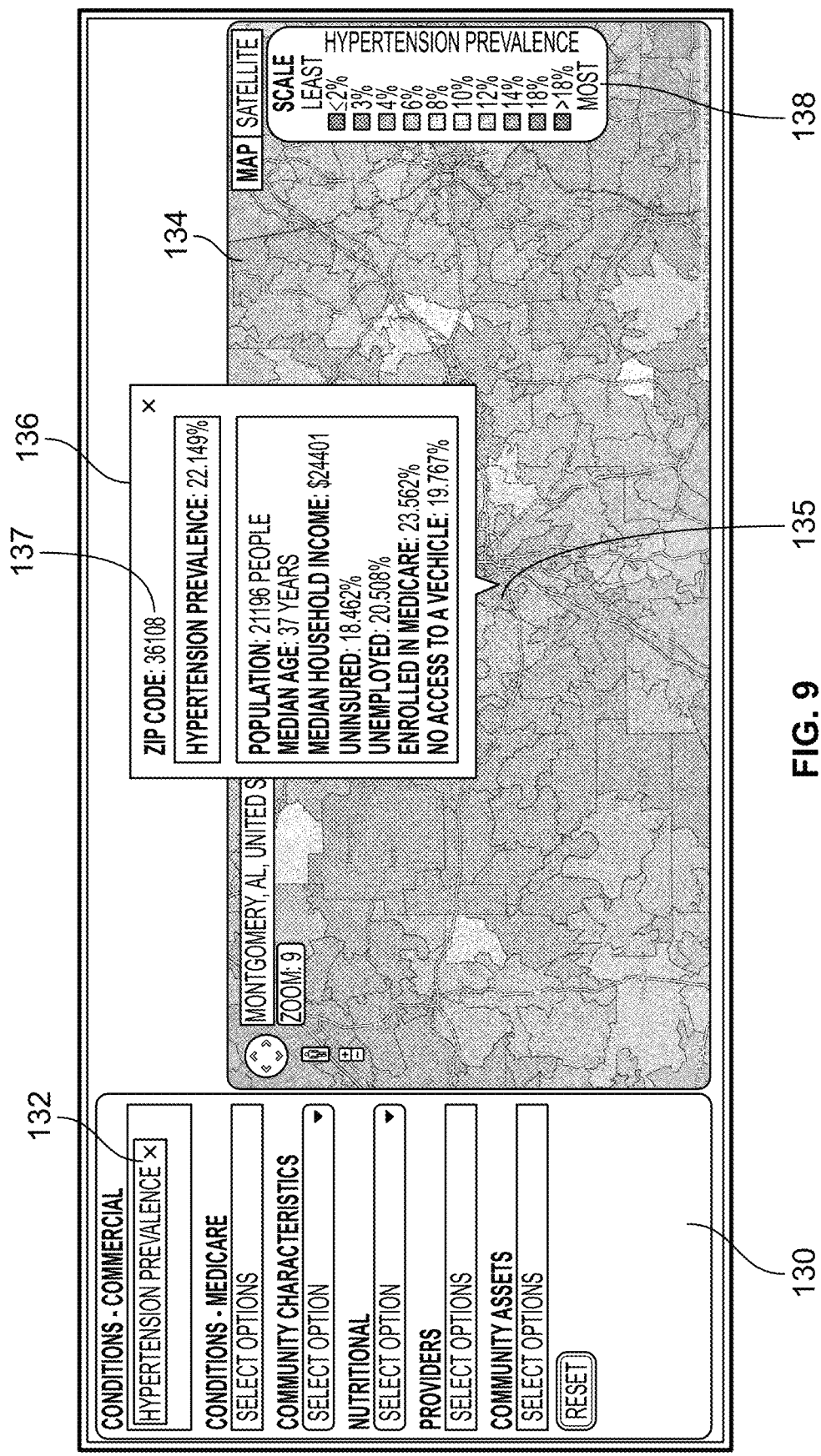

Condition prevalence in this disclosure refers to the proportion of the commercial population that presents in a reporting period, for example, the preceding 12-month period, with one inpatient claim of a particular health condition of interest or 2 outpatient claims of the condition of interest in the reporting period. For example, a user seeking to know the proportion of the commercial population that presents in a reporting period, for example, the preceding 12-month period, with one inpatient claim of a particular health condition of interest or 2 outpatient claims of the condition of interest in the reporting period may query system 110, as shown in FIGS. 8-9.

In this embodiment, as shown in FIG. 8, after entering a location, such as the name of a city, an address, or a zip code, into search box 128, a user may select the "hypertension prevalence" dropdown option 132 from among one or more selectable medical conditions in customized menu 130 to obtain the percentage of the population in the geographic location who is considered to have hypertension. The prevalence of this condition is presented to the user in graphical map image 134 where a different color or shading style is assigned to each zip code shown in the image 134 according to the prevalence of the item being searched. The geographic breadth of the image 134 may default to a particular zoom level, which zoom level may be adjustable by the user.

The image 134 is dynamically interactive with the user. Consequently, the user may select a particular color coded region corresponding to a particular zip code to obtain further statistics on the prevalence of the condition being searched. As shown in FIG. 9, for example, the user selected the geographic tile 135 corresponding to zip code "36108" (item 137), after which system 110 responds by displaying text box 136 with detailed statistical data corresponding to that zip code and for the selected health condition, which in this example, is hypertension prevalence, including community characteristics for the general population in that zip code. Legend 138 may be configured to dynamically update with information corresponding to the zoom level of image 134.

Condition frontier in this disclosure refers to, for any given medical condition selected above, the observed-to-expected ratio of the commercial population compared to the general population. Populations in underperforming zip codes may be identified relative to nationwide zip codes with these characteristics. Social Determinants of Health (SDOH) include cultural factors (e.g., race/ethnicity and language), economic factors (e.g., per capita income), educational factors (e.g., completion of primary education) and social factors (e.g., female head of household and access to vehicle).

Figure 10:
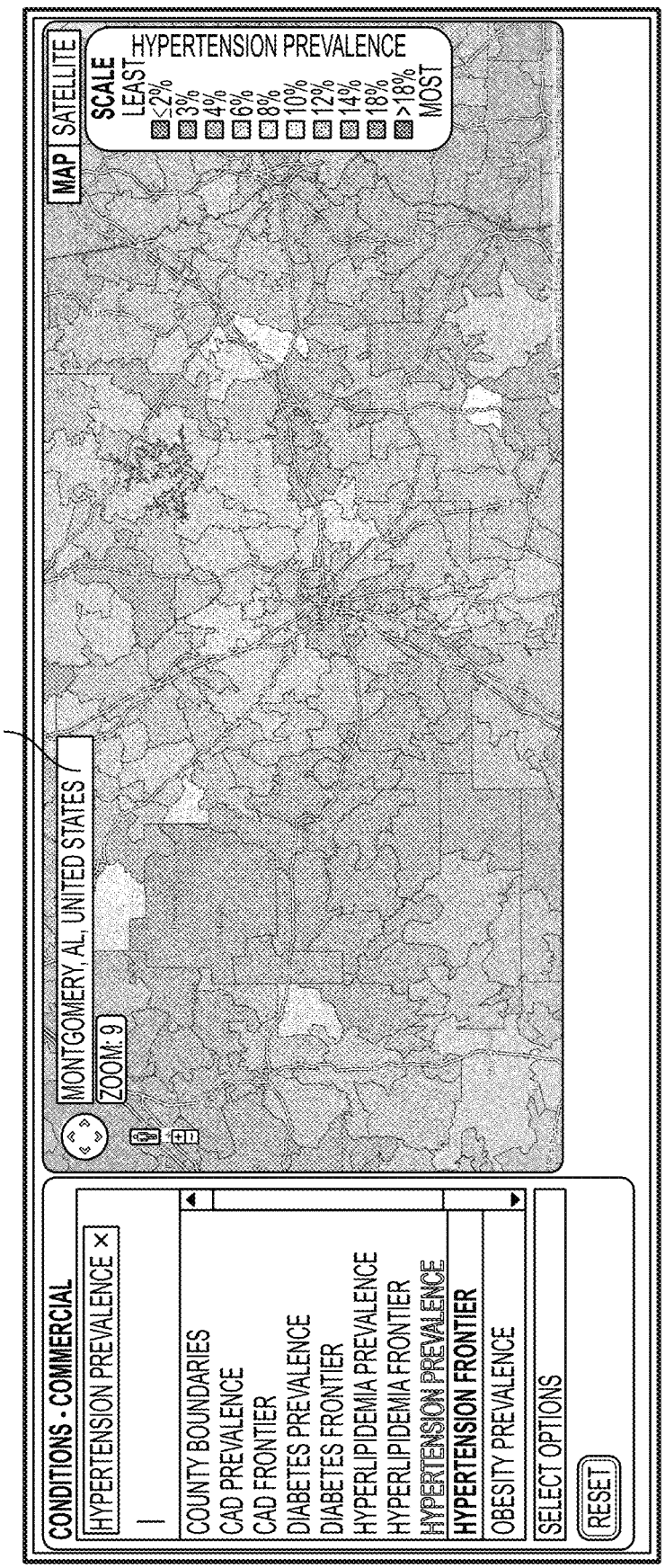
Figure 11:
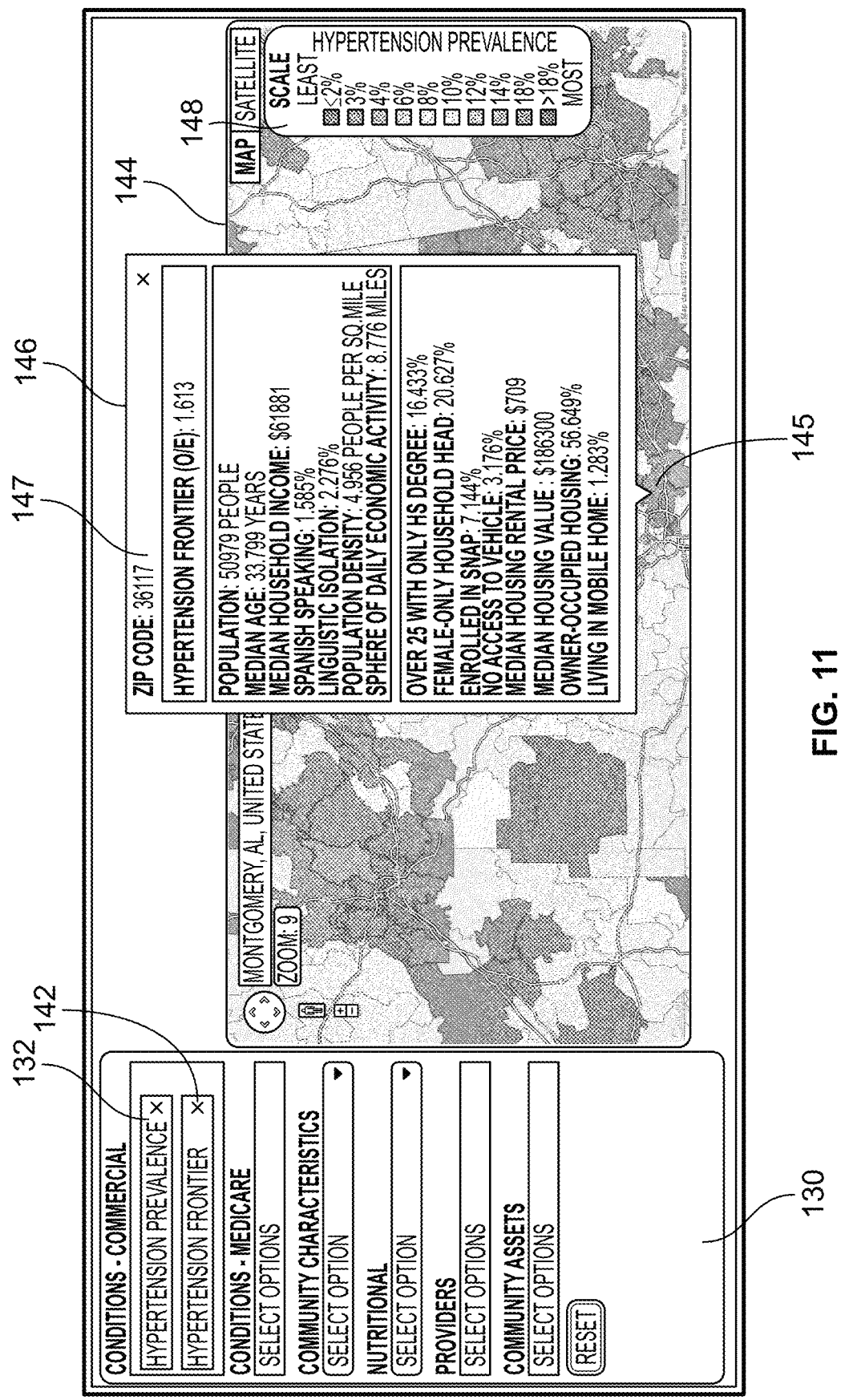

FIGS. 10 and 11 take the foregoing example a step further by identifying one or more social factors that may explain the prevalence of hypertension in the selected location. For example, once hypertension prevalence displayed in the user's browser, the user may select "Hypertension Frontier" in the dropdown option 142 from among one or more selectable options in customized menu 130 to identify underperforming zip codes relative to nationwide zip codes with similar community characteristics. The prevalence of hypertension (or any condition that is previously selected) is presented to the user in graphical map image 144 where a different color or shading style is assigned to each zip code shown in the image 144 according to the prevalence of the item being searched. The geographic breadth of the image 144 may default to a particular zoom level, which zoom level may be adjustable by the user.

The image 144 is dynamically interactive with the user. Consequently, the user may select a particular color coded region corresponding to a particular zip code to obtain further statistics on the item being searched (in this example, the hypertension frontier). As shown in FIG. 11, for example, the user selected the geographic tile 145 corresponding to zip code "36117" (item 147), after which system 110 responds by displaying text box 146 with detailed statistical data corresponding to that zip code and for the selected health condition, which in this example, is hypertension prevalence and the hypertension observed-to-expected ratio (O/E) associated with that condition for that zip code, including community characteristics for the general population in that zip code. Legend 148 may be configured to dynamically update with information corresponding to the zoom level of image 144.

Figure 12:
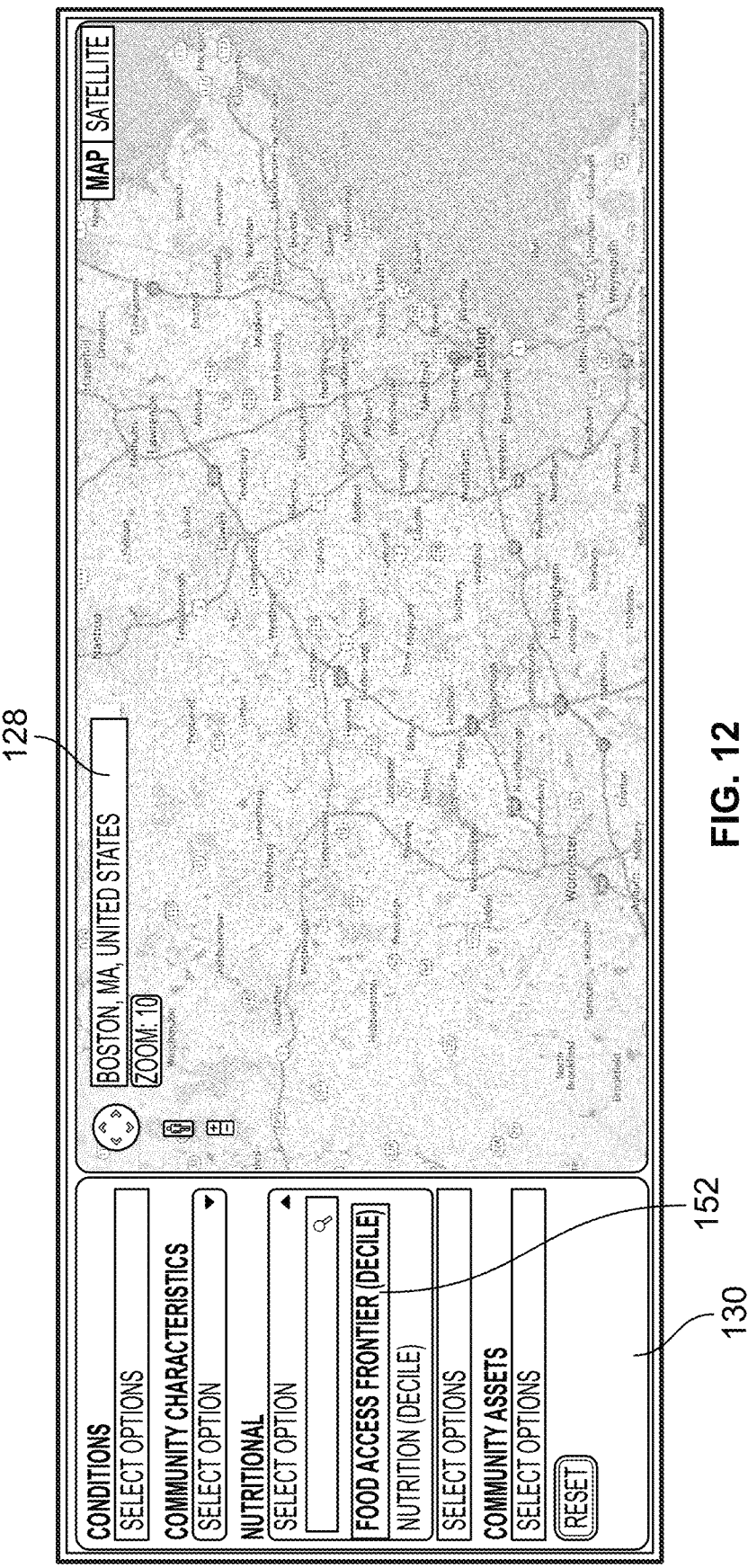
Figure 13:
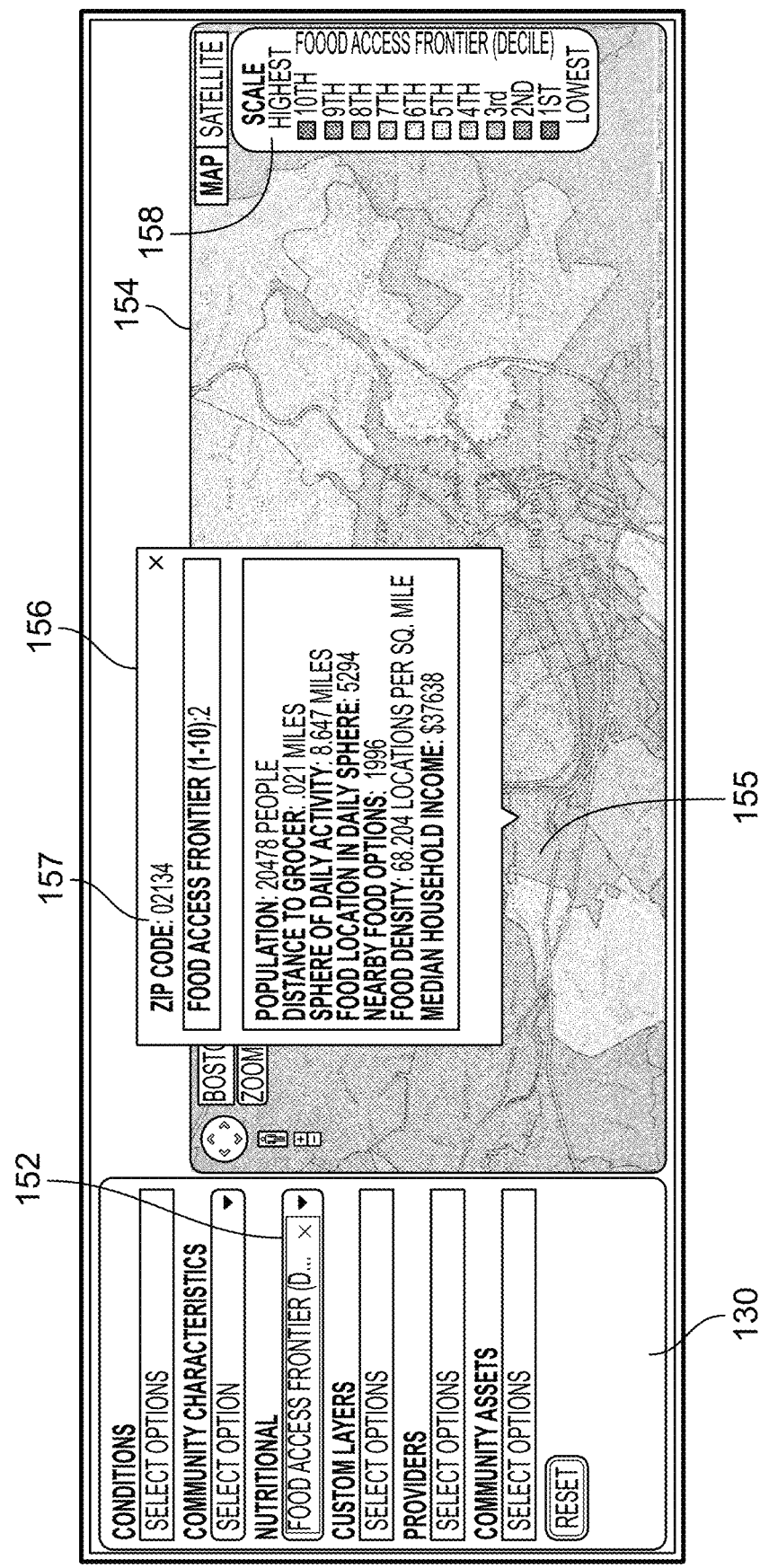

Food access frontier in this disclosure refers to the availability of food options and access thereof, by zip code. The food access frontier comparison considers relatively low areas of healthy food options (e.g., "food deserts") and high areas of unhealthy food options (e.g., "food swamps"). The methodology employed by server system 110 may control for median household income and commuting patterns, which may be described as part of the economic sphere of daily activity. The calculated results may be arrayed by deciles, as shown in FIGS. 12-13.

For example, after entering a location, such as the name of a city, an address, or a zip code, into search box 128, a user may select the "food access frontier" dropdown option 152 from among one or more selectable nutritional options in customized menu 130 to obtain the availability by the population to different food options in that geographic location.

As discussed above, the results of the food access frontier search for the particular geographic location entered into search box 128 are presented to the user in graphical map image 154 where a different color or shading style is assigned to each zip code shown in the image 154 according to the prevalence of the item being searched. The geographic breadth of the image 154 may default to a particular zoom level, which zoom level may be adjustable by the user.

As discussed above, the image 154 is dynamically interactive with the user. Consequently, the user may select a particular color coded region corresponding to a particular zip code to obtain further statistics on the food access frontier. As shown in FIG. 13, for example, the user selected the geographic tile 155 corresponding to zip code "36117" (item 157), after which system 110 responds by displaying text box 156 with detailed statistical data corresponding to that zip code and for the selected nutritional dropdown item. In this example, the food access frontier (in deciles), average distance to the nearest grocer, food options within the daily commuting sphere, number of food options, and median household income may provide an indication of the environmental and socioeconomic impact on health of the population represented by the selected geographic location. Legend 158 may be configured to dynamically update with information corresponding to the zoom level of image 154.

Figure 14:
Figure 15:
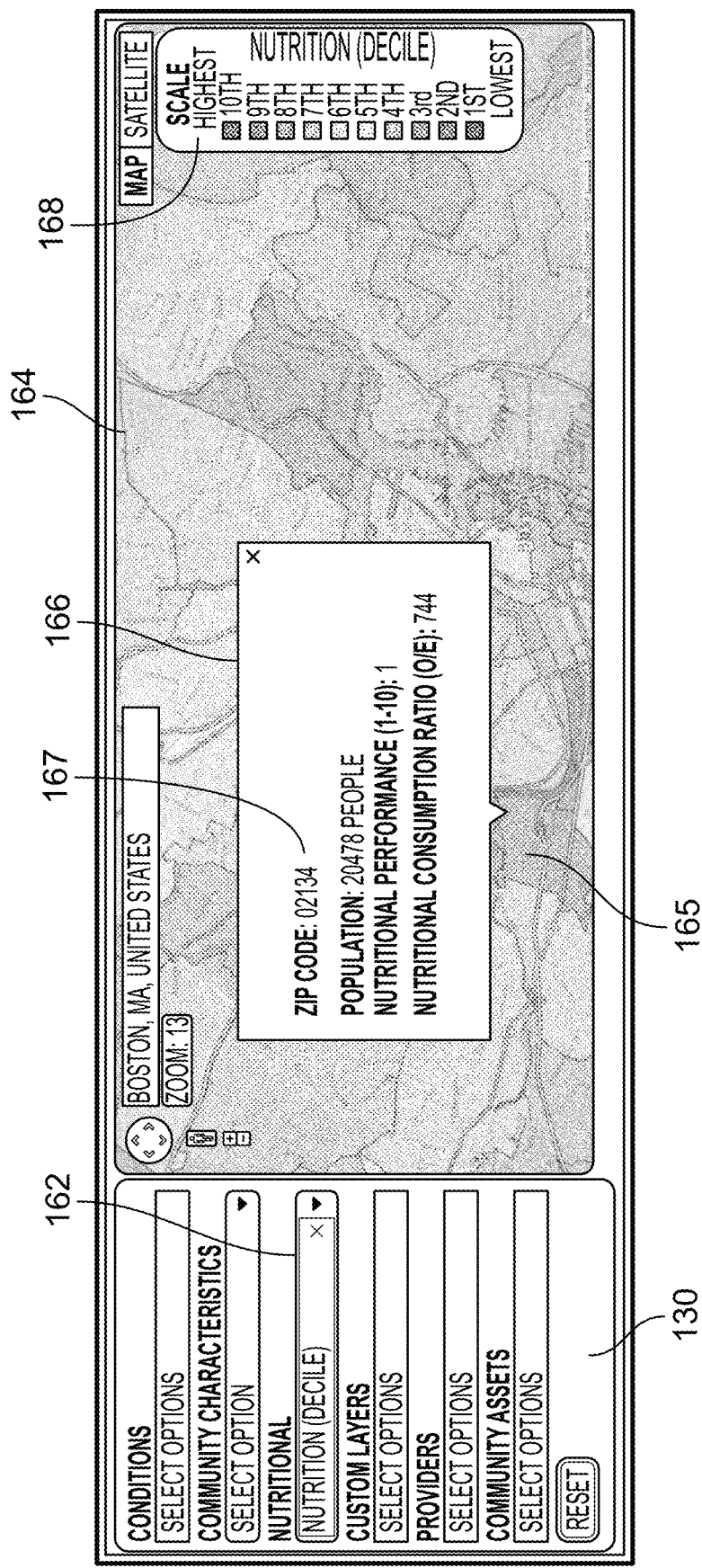

Nutrition in this disclosure refers to a nutritional performance measure, which may compare scanned grocery store purchases at the zip code level for both chain and independent stores. The comparison may consider fruits, whole grains, and vegetables relative to total purchases. The methodology employed by server system 110 may control for median household income and commuting patterns, which may be described as part of the economic sphere of daily activity. The calculated results may be arrayed by deciles, as shown in FIGS. 14-15.

For example, after entering a location, such as the name of a city, an address, or a zip code, into search box 128, a user may select the "nutrition (decile)" dropdown option 162 from among one or more selectable nutritional options in customized menu 130 to obtain food purchasing patterns at the selection location.

As discussed above, the results of the nutrition search for the particular geographic location entered into search box 128 are presented to the user in graphical map image 164 where a different color or shading style is assigned to each zip code shown in the image 164 according to the prevalence of the item being searched. The geographic breadth of the image 164 may default to a particular zoom level, which zoom level may be adjustable by the user.

As discussed above, the image 164 is dynamically interactive with the user. Consequently, the user may select a particular color coded region corresponding to a particular zip code to obtain further statistics on nutrition for the selected geographic location. As shown in FIG. 15, for example, the user selected the geographic tile 165 corresponding to zip code "02134" (item 167), after which system 110 responds by displaying text box 166 with detailed statistical data corresponding to that zip code and for the selected nutritional dropdown item. In this example, the nutritional performance (in deciles) and the observed-to-expected (O/E) ratio are presented in text box 166, which may provide an indication of the environmental and socioeconomic impact on health of the population represented by the selected geographic location. Legend 168 may be configured to dynamically update with information corresponding to the zoom level of image 164.

Figure 16:
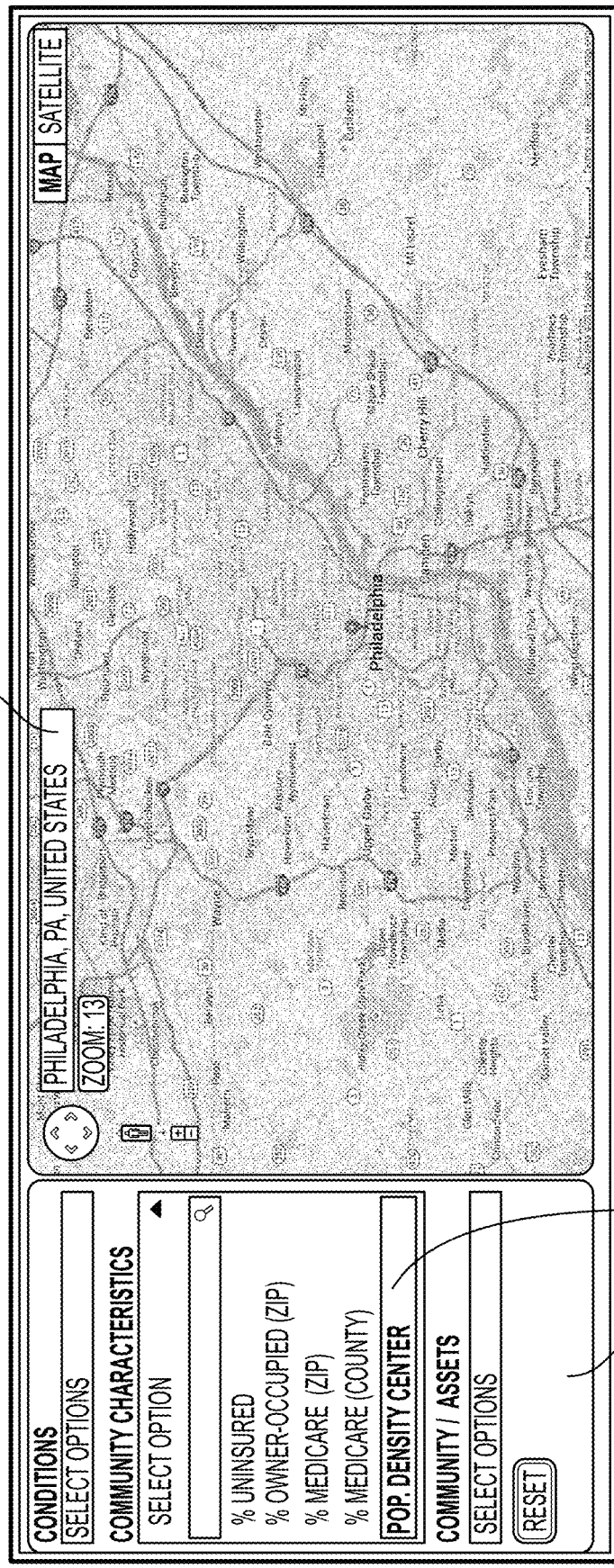
Figure 17:
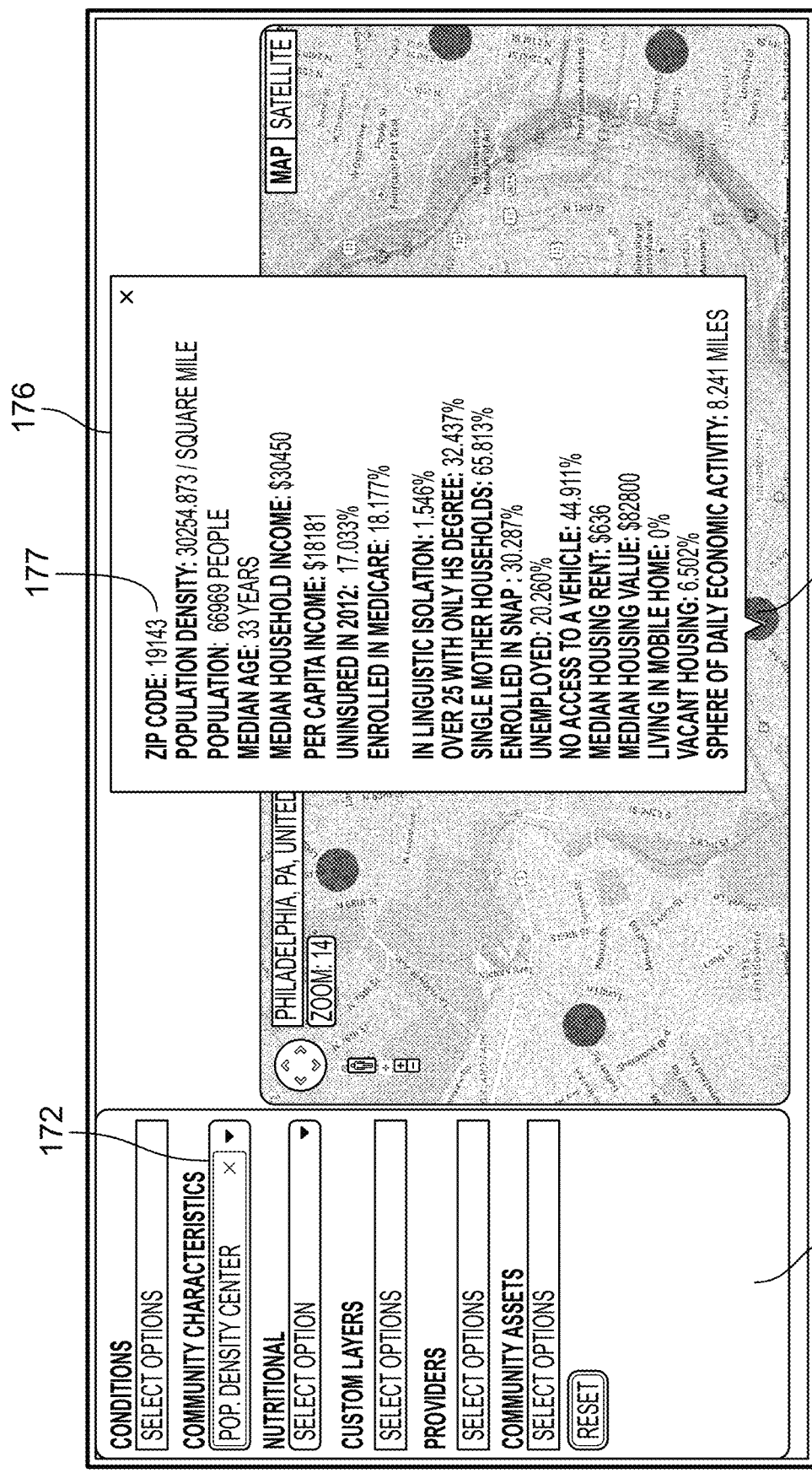

Population density center in this disclosure refers to a measure of a community characteristic to provide the spatial location of the population density. This measure may aggregates the location of the population from the block level to the zip code. The measure calculation may utilize US Census data at the block level to determine population per square mile, as shown in FIGS. 16-17.

For example, after entering a location, such as the name of a city, an address, or a zip code, into search box 128, a user may select the "population density center" dropdown option 172 from among one or more selectable community characteristics options in customized menu 130 to obtain the density of the population, among other statistics, at a selected location.

As discussed above, the results of the population density search for the particular geographic location entered into search box 128 are presented to the user in graphical map image 174 where a selectable icon corresponding to population density and other statistics for that geographical location overlays image 174. The geographic breadth of the image 174 may default to a particular zoom level, which zoom level may be adjustable by the user.

As discussed above, the image 174 is dynamically interactive with the user. Consequently, the user may select a particular icon to obtain further statistics on the geographic location. As shown in FIG. 17, for example, the user selected the icon 175 corresponding to zip code "19143" (item 177), after which system 110 responds by displaying text box 176 with detailed statistical data corresponding to people residing in that zip code and for the selected community characteristics dropdown item.

Providers in this disclosure refers to the spatial location of health care providers in the community. In combination with other layers, the health care provider location layer allows users to identify potential partners to address population health.

Figure 18:
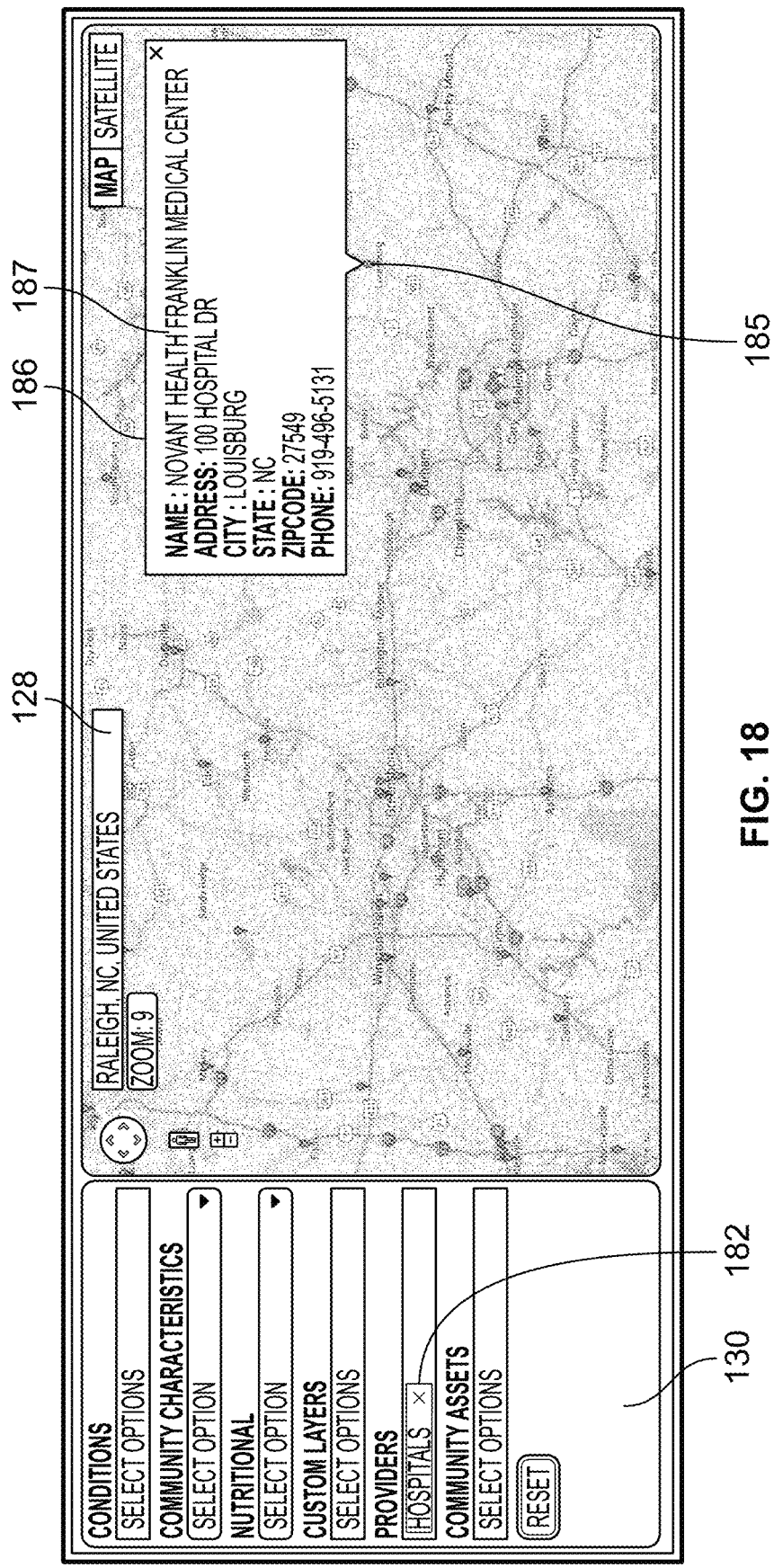
Figure 19:
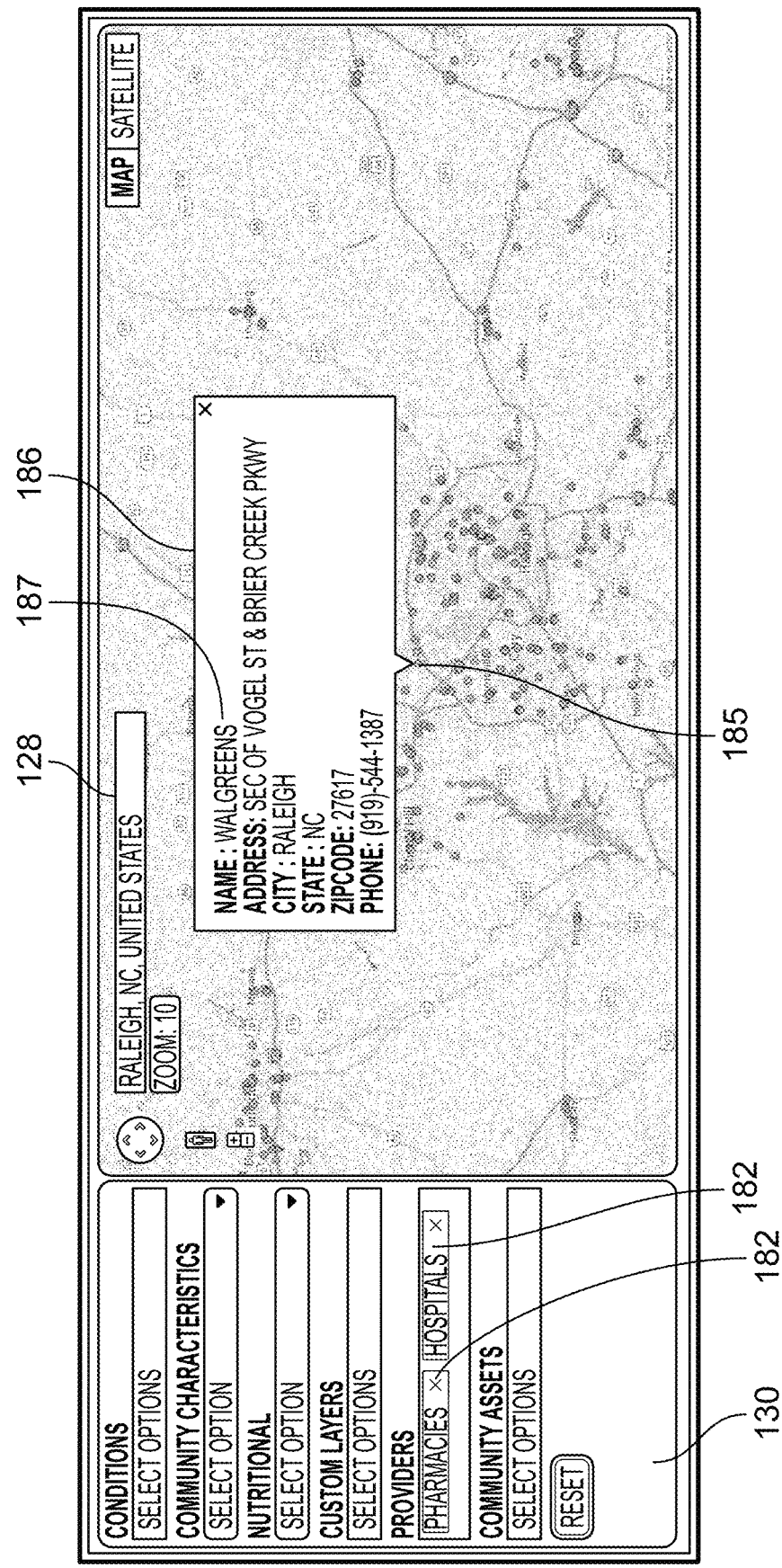

As shown in FIGS. 18-19, after entering a location, such as the name of a city, an address, or a zip code, into search box 128, one or more health care providers 182 may be displayed in image 184 that correspond to the selected location. For example, a user may select the "hospitals" or the "hospitals" and the "pharmacies" dropdown option 182 from among one or more selectable provider options in customized menu 130 to obtain information concerning health care providers and/or pharmacies that serve that particular location or geographic region.

As discussed above, the results of the provider search for the particular geographic location entered into search box 128 are presented to the user in graphical map image 184 where a selectable icon corresponding to the selected item being searched and other statistics for that item are overlaid onto image 184. The geographic breadth of the image 184 may default to a particular zoom level, which zoom level may be adjustable by the user.

As discussed above, the image 184 is dynamically interactive with the user. Consequently, the user may select a particular icon to obtain further statistics on the geographic location. As shown in FIGS. 18 and 19, for example, the user selected the icon 185 corresponding to "Novant Health Franklin Medical Center" (item 187 in FIG. 18) and "Walgreens" (item 187 in FIG. 19), after which system 110 responds by displaying text box 186 with detailed statistical data corresponding to the selected health care provider.

Turning now to FIGS. 20-52, there is shown various exemplary search options for various exemplary social determinants of health, such minority population prevalence, race/ethnicity prevalence, linguistic isolation prevalence, prevalence of a foreign language as the primary language, level of education, per capita income, income distribution, unemployment prevalence, prevalence of population not in the labor force, poverty prevalence, prevalence of disabled people living in poverty, marital status, prevalence of female only householders, prevalence of no access to a vehicle, prevalence of the population enrolled in Supplemental Nutritional Assistance Program (SNAP), and family size, among others.

Figure 21:
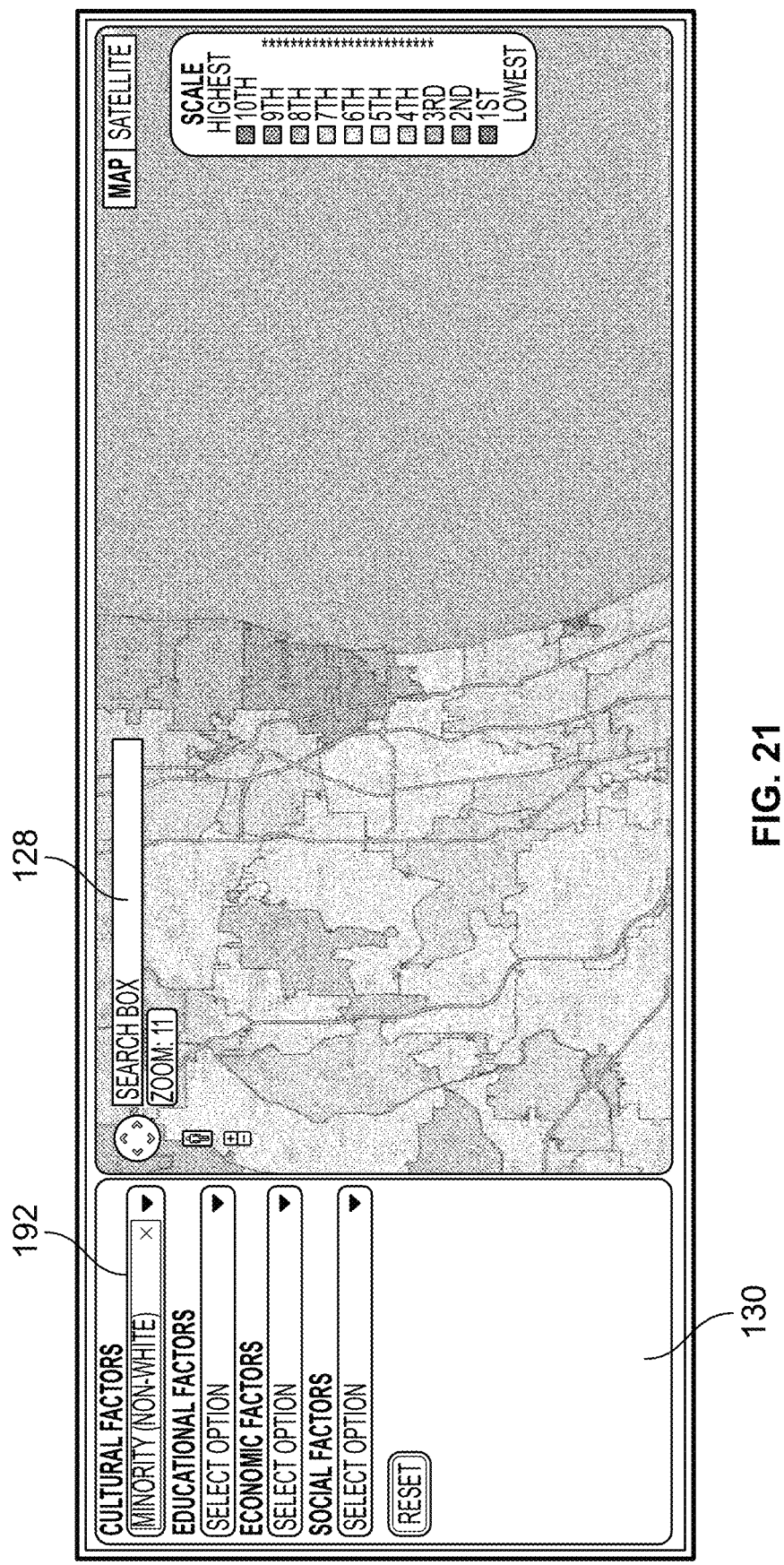
Figure 22:
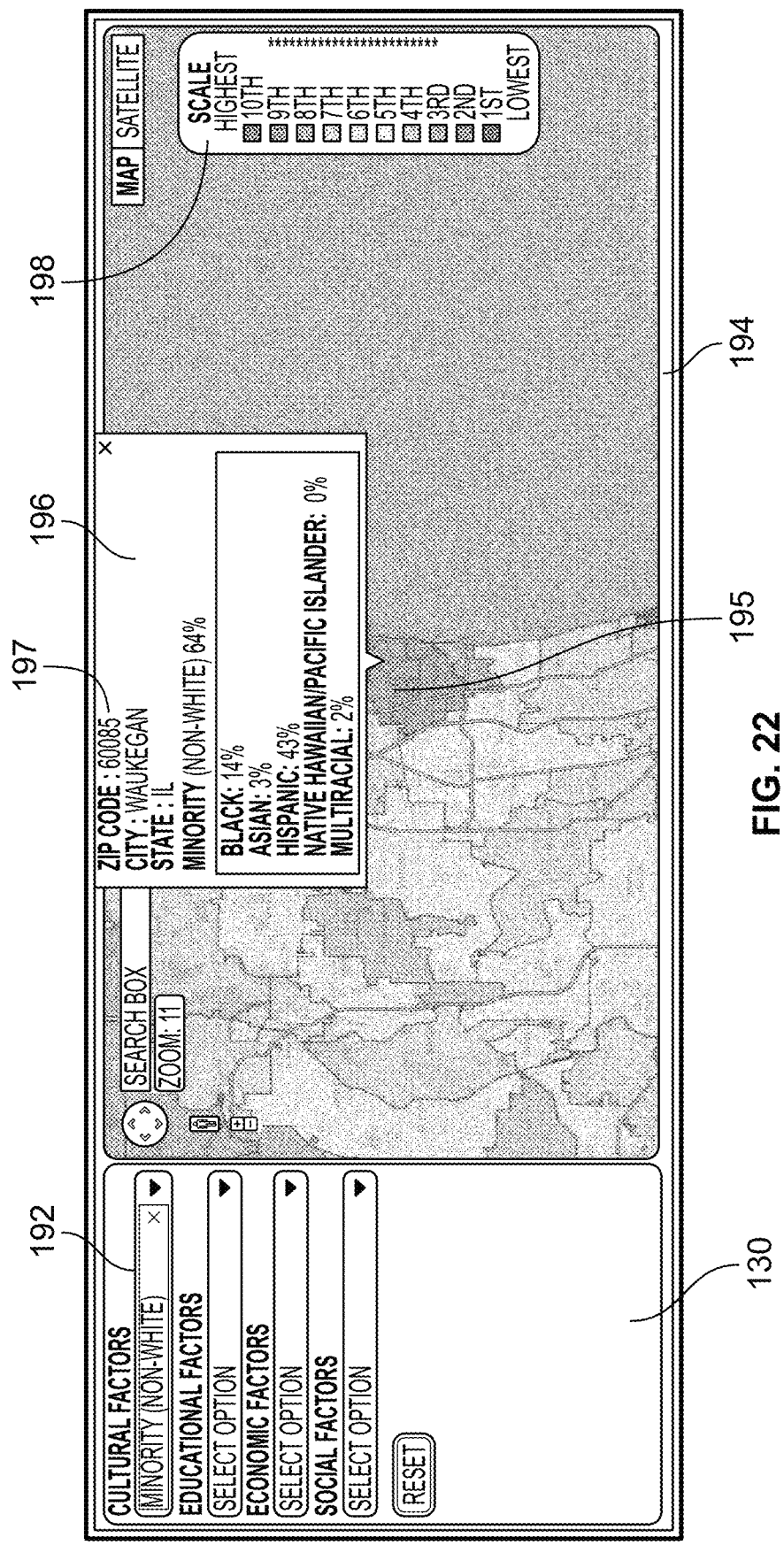

For example, FIGS. 21-22 show that after entering a location, such as the name of a city, an address, or a zip code, into search box 128, a user may select the "minority (non-white)" dropdown option 192 from among one or more cultural factors options in customized menu 130 to obtain minority statistics of the population, among other statistics, at the selected location.

As discussed above, the results of the minority search for the particular geographic location entered into search box 128 are presented to the user in graphical map image 194 where a different color or shading style is assigned to each zip code shown in the image 194 according to the prevalence of the item being searched. The geographic breadth of the image 194 may default to a particular zoom level, which zoom level may be adjustable by the user.

As discussed above, the image 194 is dynamically interactive with the user. Consequently, the user may select a particular color coded region corresponding to a particular zip code to obtain further statistics on nutrition for the selected geographic location. As shown in FIG. 22, for example, the user selected the geographic tile 195 corresponding to zip code "60085" (item 197), after which system 110 responds by displaying text box 196 with detailed statistical data corresponding to that zip code and for the selected cultural factors dropdown item. Legend 198 may be configured to dynamically update with information corresponding to the zoom level of image 194.

Figure 23:
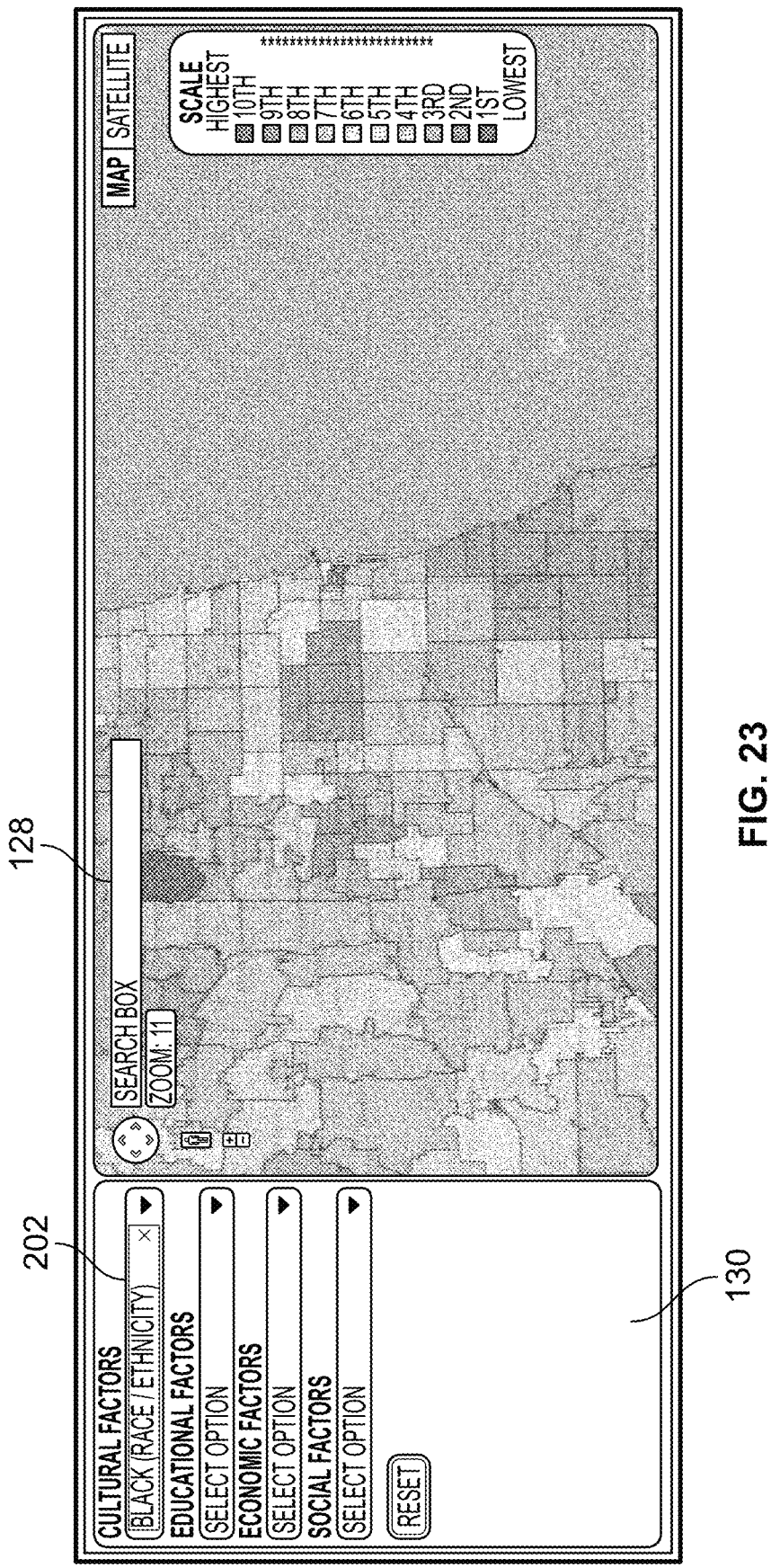
Figure 24:
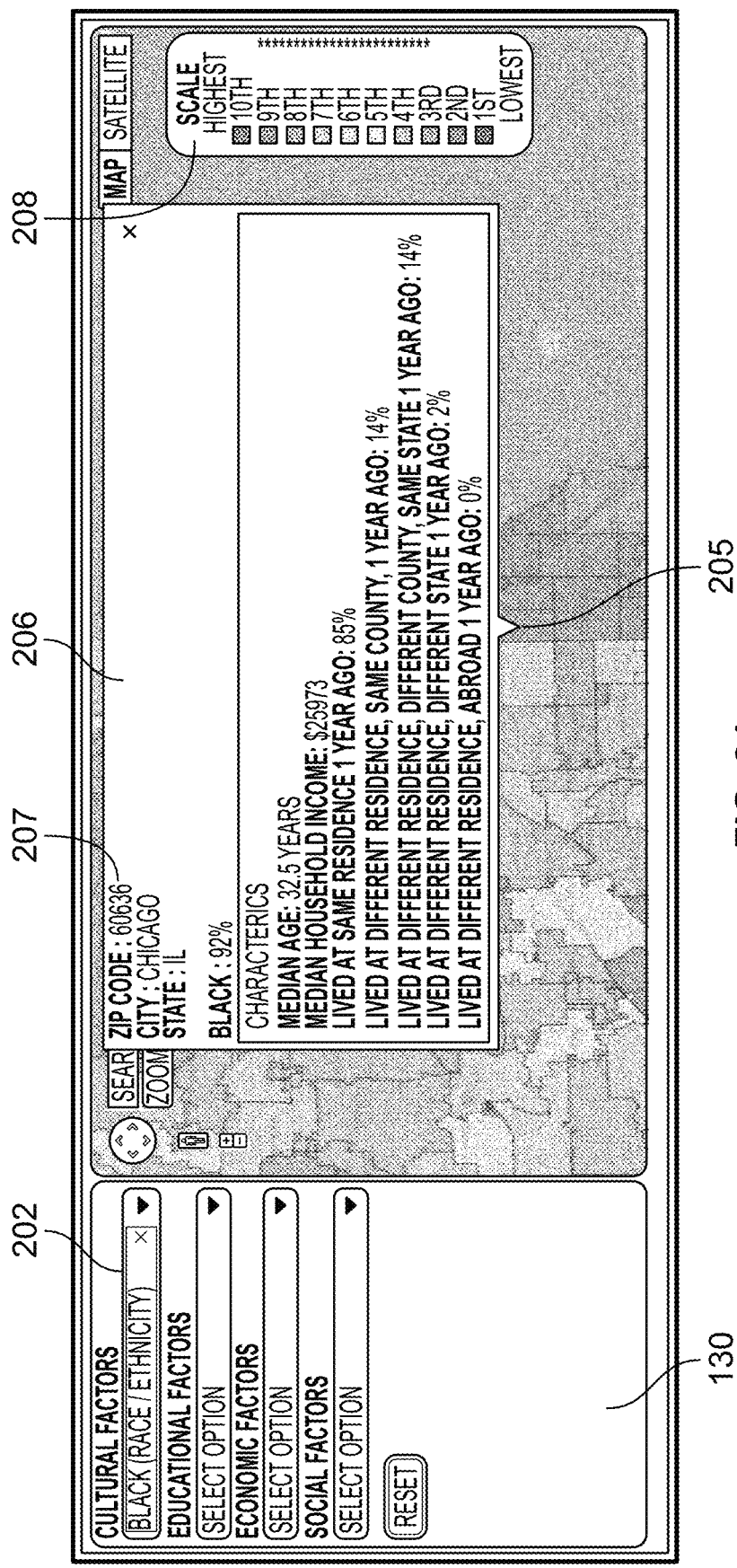

Similarly, FIGS. 23-24 show that after entering a location, such as the name of a city, an address, or a zip code, into search box 128, a user may select the "Black (Race/Ethnicity)" dropdown option 202 from among one or more cultural factors options in customized menu 130 to obtain minority statistics of the population, among other statistics, at the selected location.

As discussed above, the results of the black (race/ethnicity) search for the particular geographic location entered into search box 128 are presented to the user in graphical map image 204 where a different color or shading style is assigned to each zip code shown in the image 204 according to the prevalence of the item being searched. The geographic breadth of the image 204 may default to a particular zoom level, which zoom level may be adjustable by the user.

As discussed above, the image 204 is dynamically interactive with the user. Consequently, the user may select a particular color coded region corresponding to a particular zip code to obtain further statistics on race/ethnicity for the selected geographic location. As shown in FIG. 24, for example, the user selected the geographic tile 205 corresponding to zip code "60636" (item 207), after which system 110 responds by displaying text box 206 with detailed statistical data corresponding to that zip code and for the selected cultural factors dropdown item. Legend 208 may be configured to dynamically update with information corresponding to the zoom level of image 204.

Figure 25:
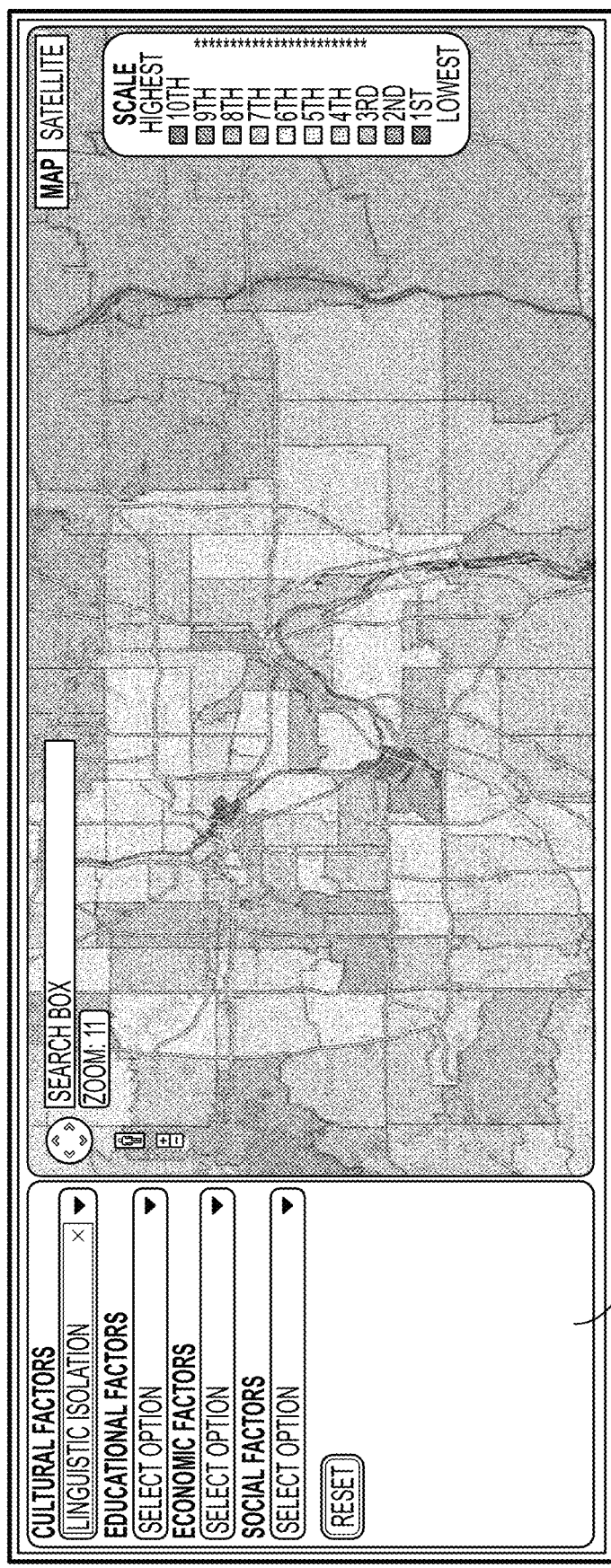
Figure 26:
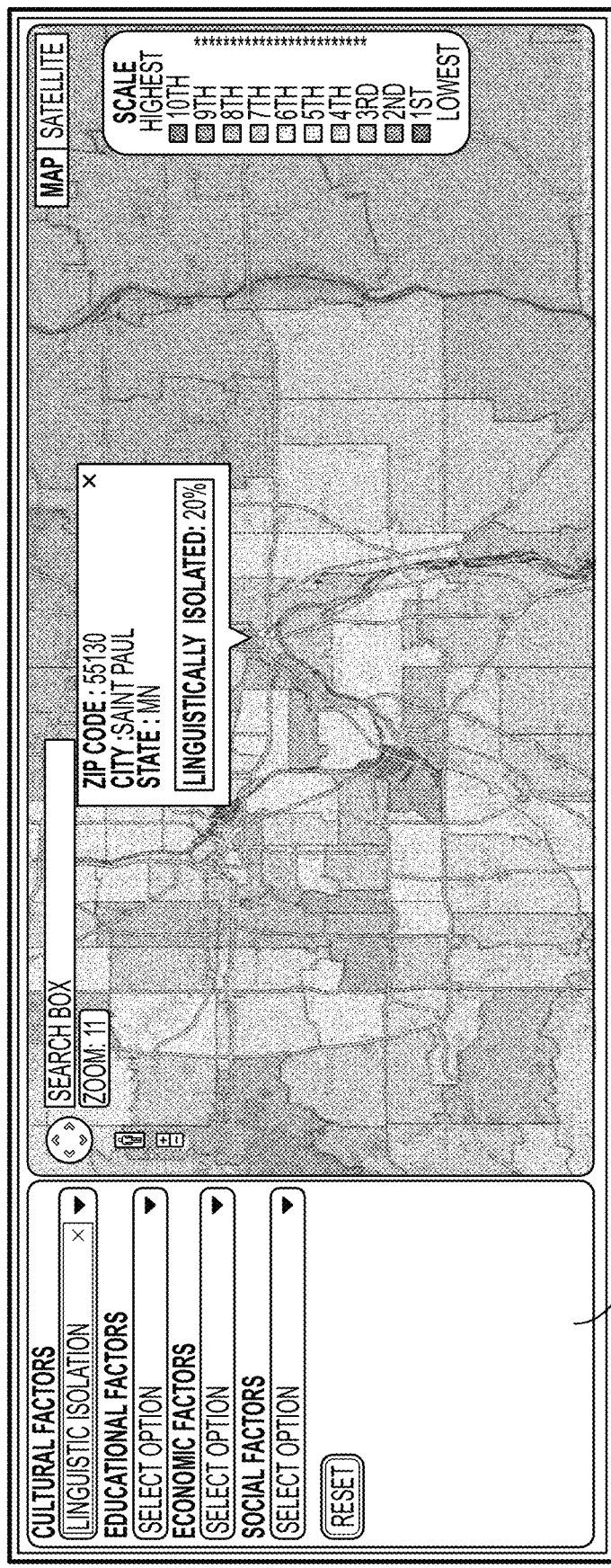
Figure 27:
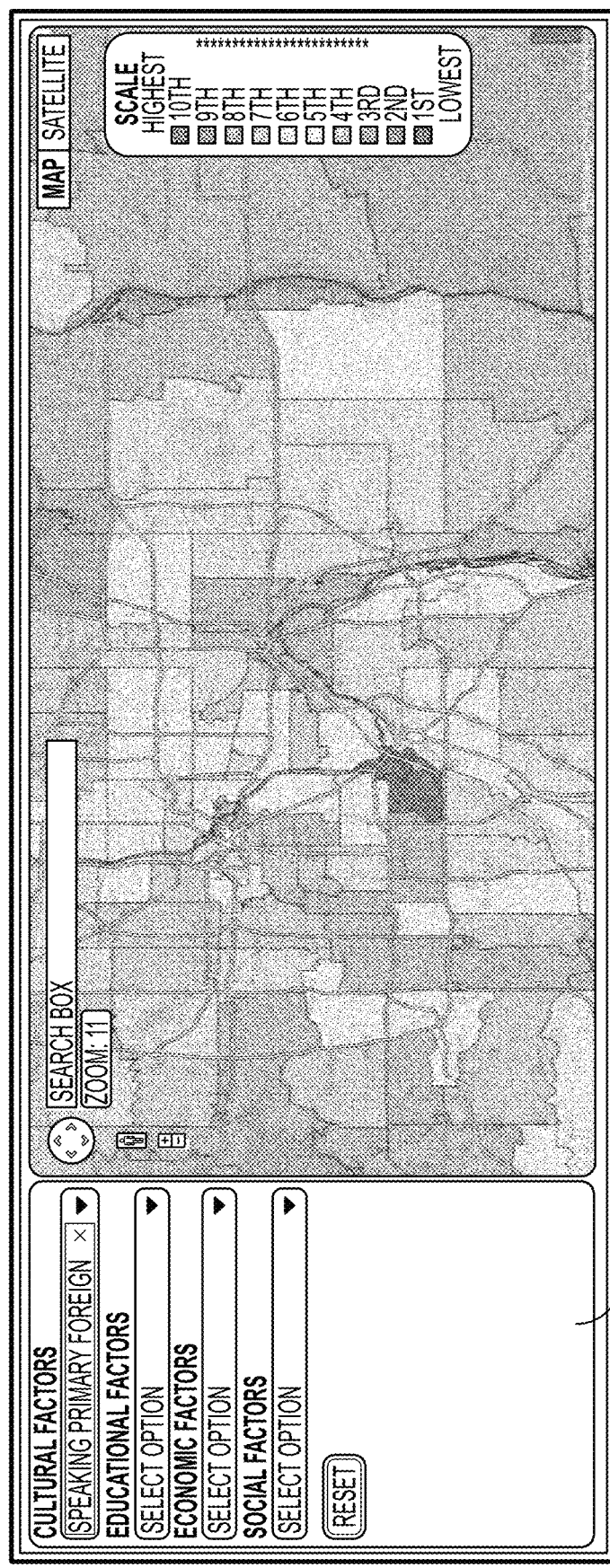
Figure 28:
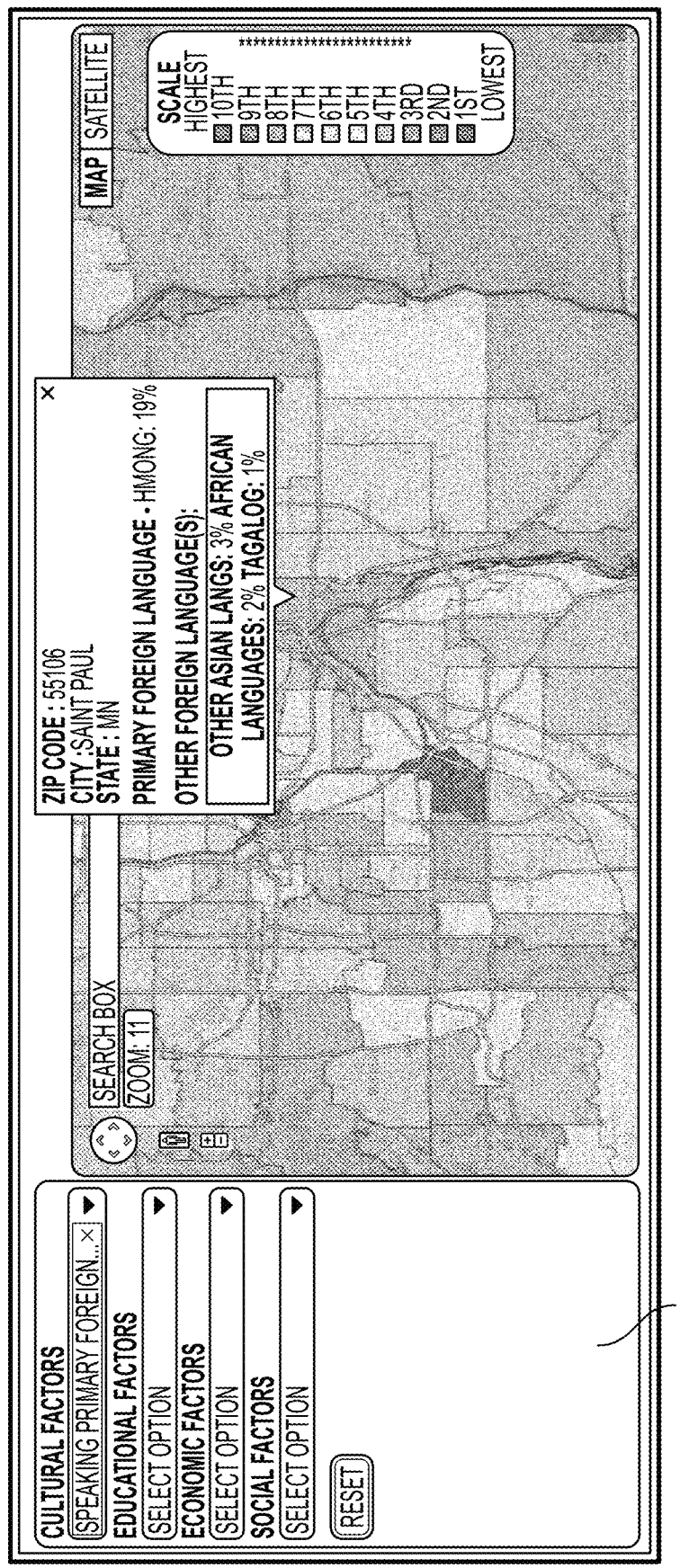

Similarly, FIGS. 25-26 show representative cultural factor data associated with linguistics isolation, which is defined in this embodiment as referring to the prevalence of families and/or the proportion of the population in the selected geographic location that have no one over the age of 14 having English as the primary language. FIGS. 27-28 show representative cultural factor data associated with speaking primarily a foreign language, which is defined in this embodiment as referring to the identities and prevalence of the primary or preferred foreign languages spoken within the selected geographic location. Each of these cultural factor options for a selected geographic location may be displayed in the same way as discussed above.

Figure 29:
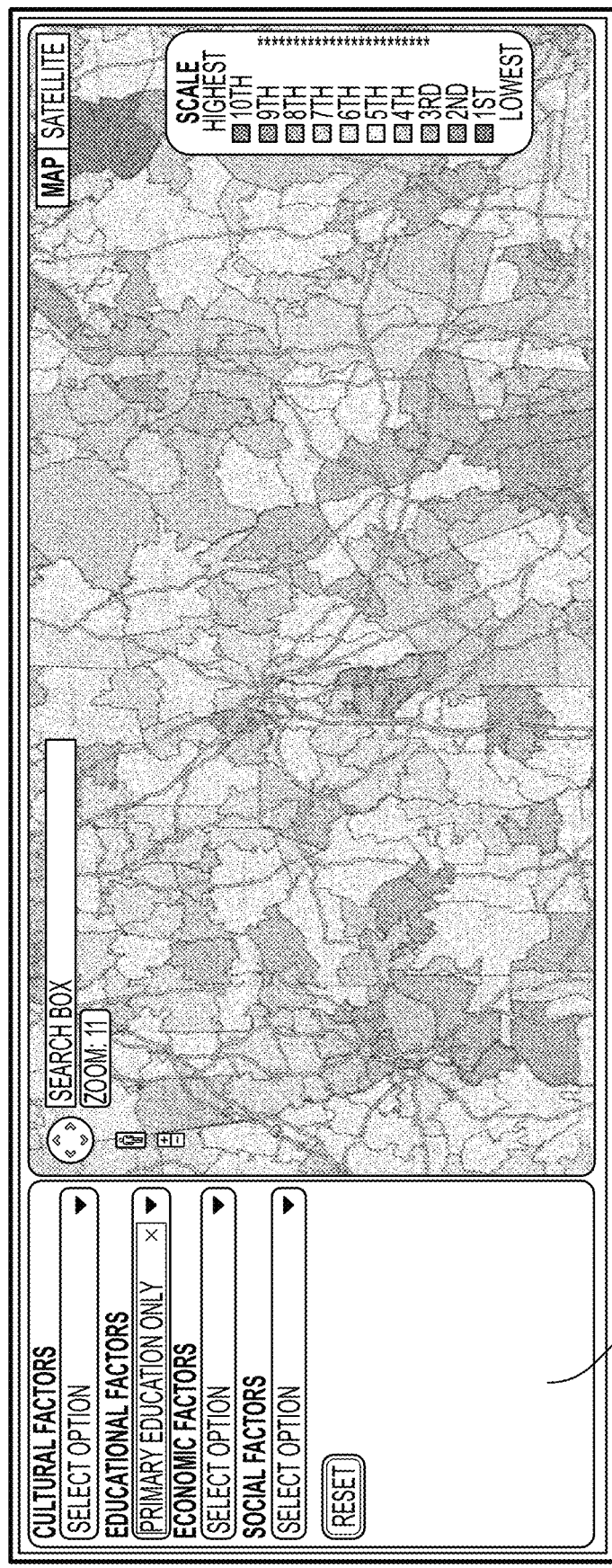
Figure 30:
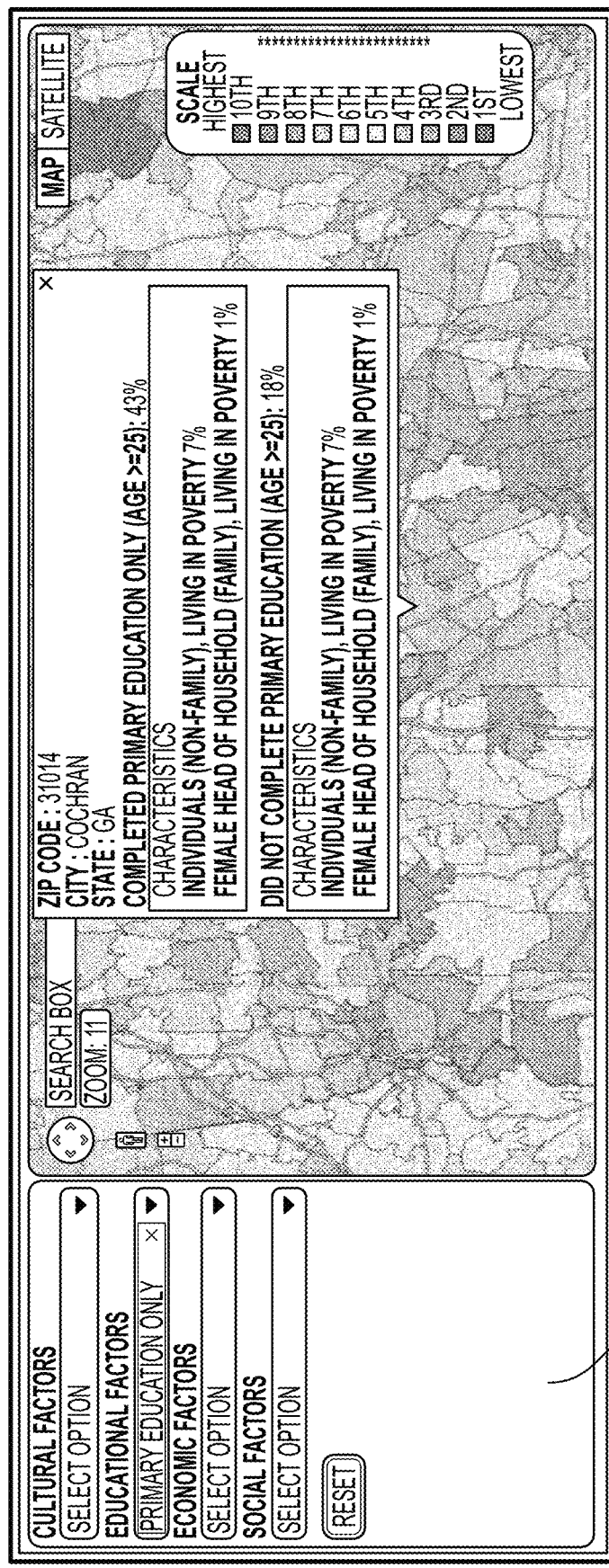

FIGS. 29-30 show representative educational factor data associated with the proportion of people having a selected level of education in a selected geographic location. For example, a user using system 110 may identify zip codes having a higher proportion of people that have completed only primary education, along with other socioeconomic statistics about the population.

Figure 31:
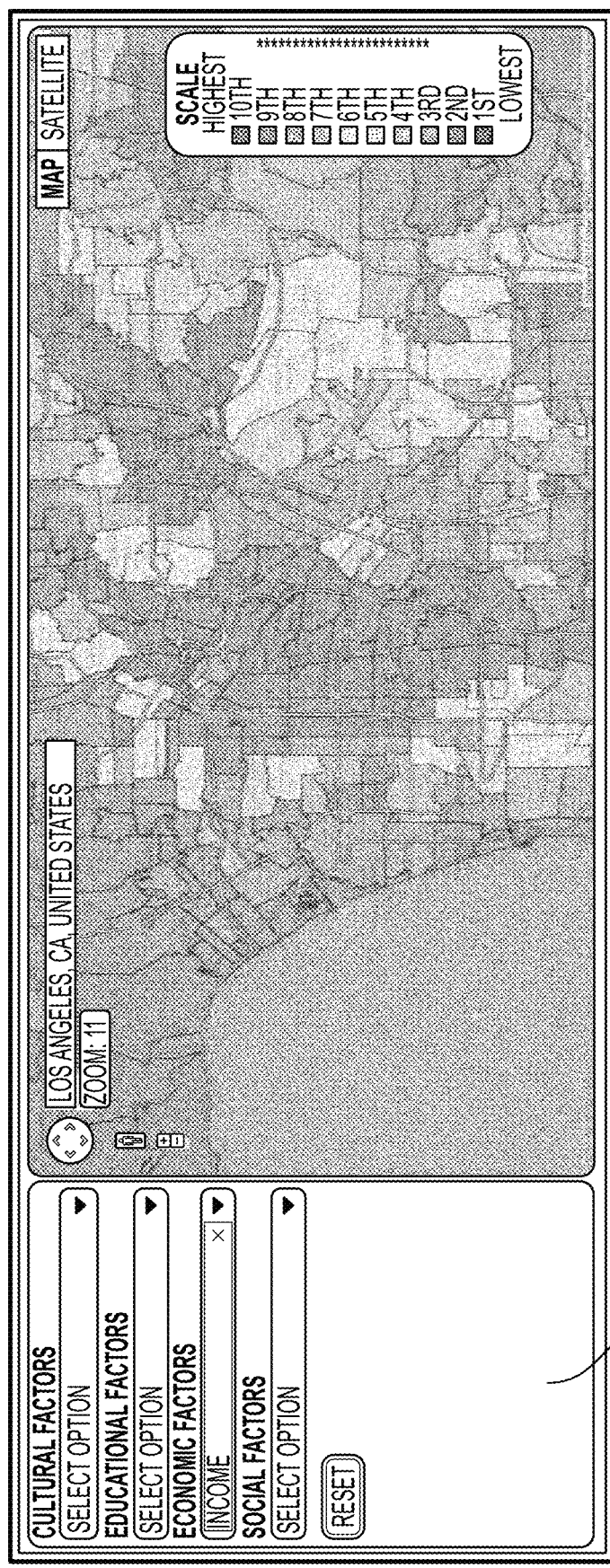
Figure 32:
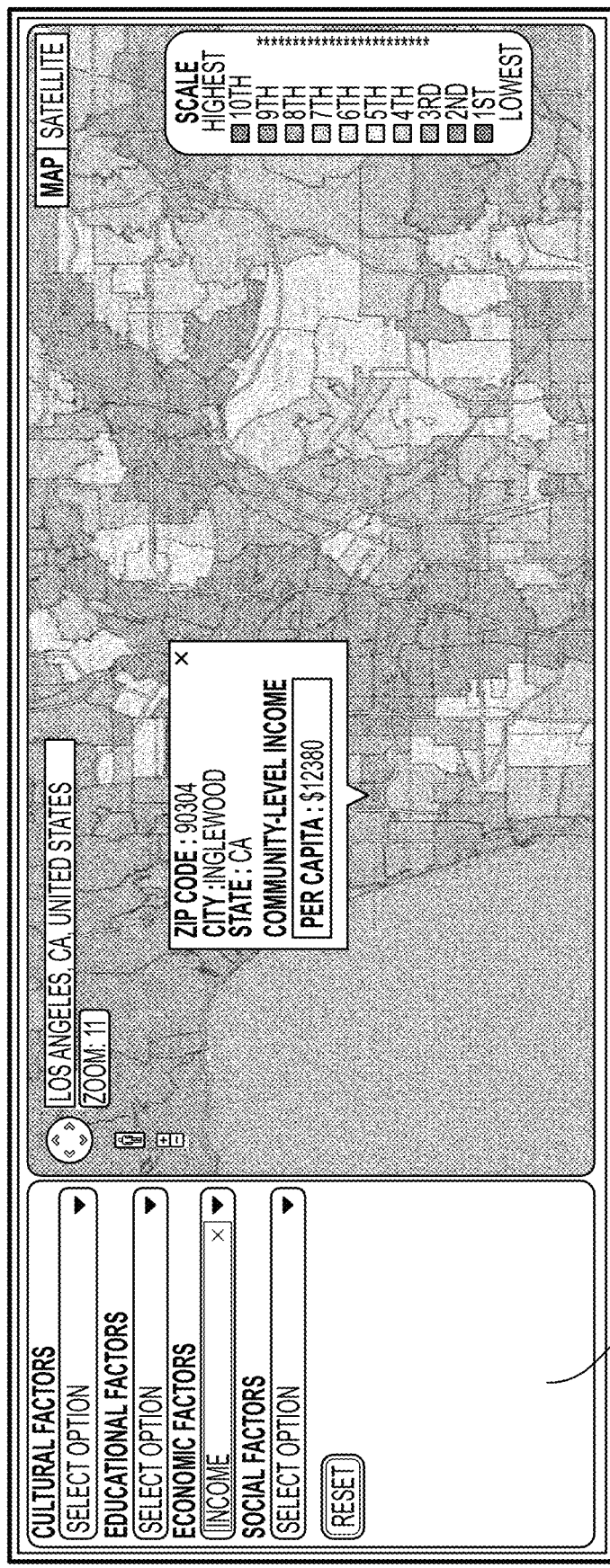
Figure 33:
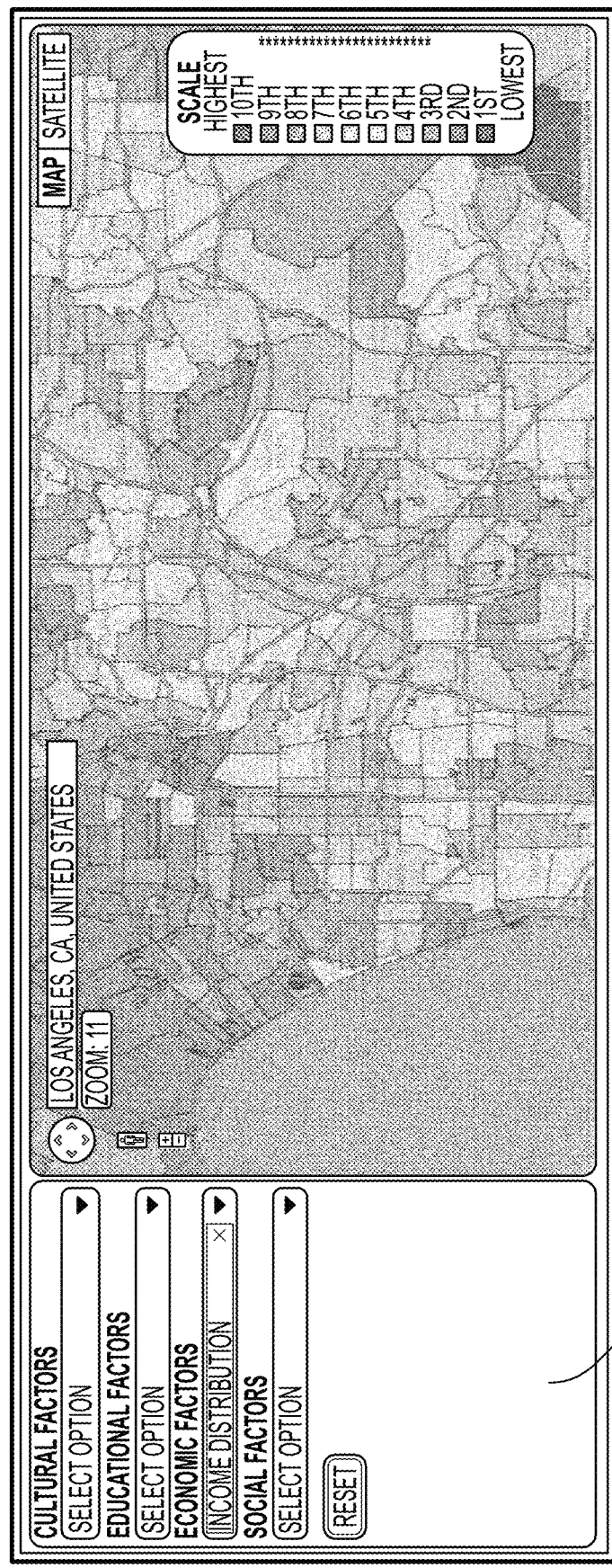
Figure 34:
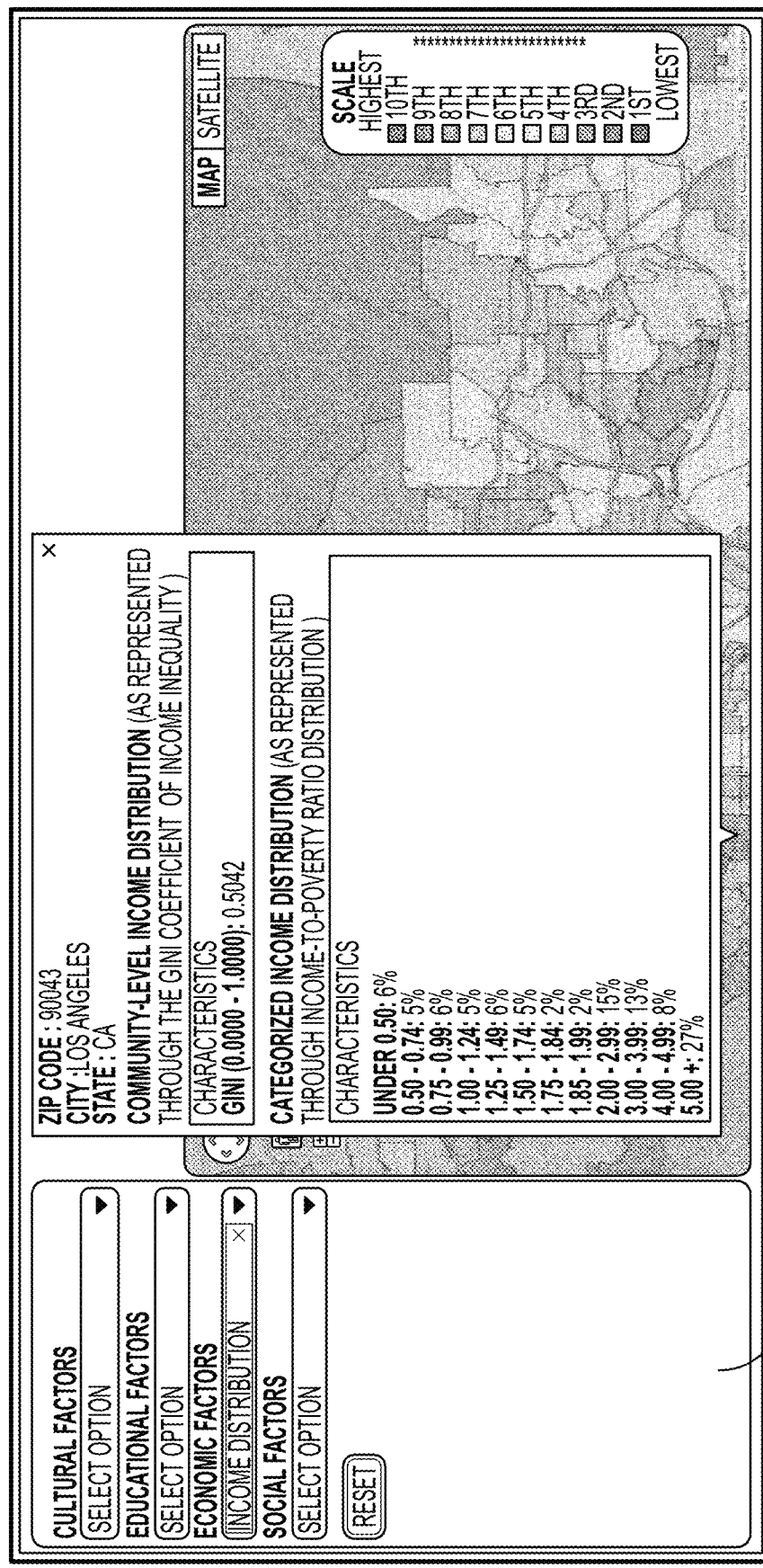

FIGS. 31-32 show representative economic factor data associated with the per capita income of people in a selected geographic location. FIGS. 33-34 show another example of economic factor data reflecting the distribution of income in the selected geographic location. System 110 may use a zip code Gini coefficient, which is a measure of inequality of a distribution (in this example, wealth) defined as a ratio with values between 0 and 1. The numerator is the area between the Lorenz curve of the distribution and the uniform distribution line. The denominator is the area under the uniform distribution line. System 110 may display a pop-up window representing an income distribution layer, which may contains additional detailed information for the categorical distribution of income-to-poverty ratio. In one embodiment, the income-to-poverty ratio is a family's or person's income divided by their poverty threshold, as defined by the US Census Bureau. The income-to-poverty ratio categories shown in FIG. 34 represent variations of the poverty level within a zip code or geographic location. Ratios below 1.00 (below 100% of poverty) are below the official poverty definition provided by the US Census Bureau, while ratios of 1.00 or greater (100% of poverty or greater) indicate income above the poverty level. Ratios below 0.50 (50% of poverty) may be described as "severe poverty", while those with ratios at/or above 1.00 but less than 1.25 may be described as "near poverty".

Figure 35:
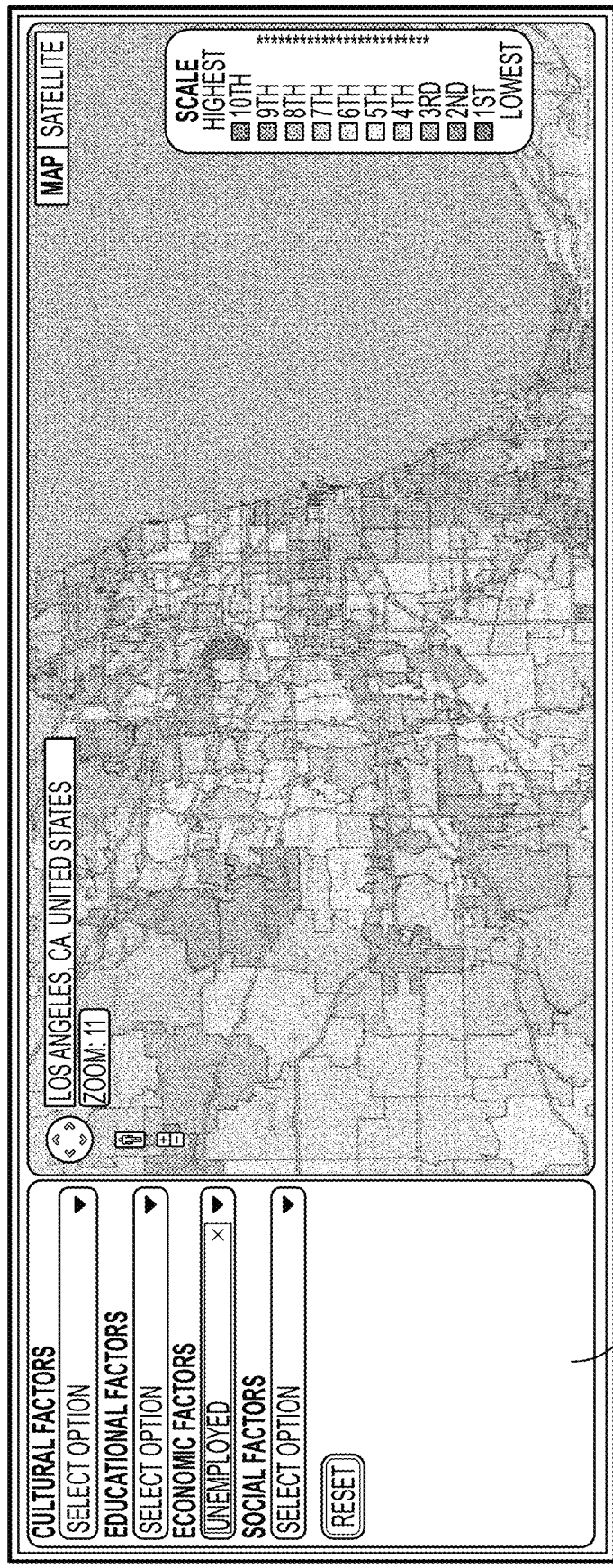
Figure 36:
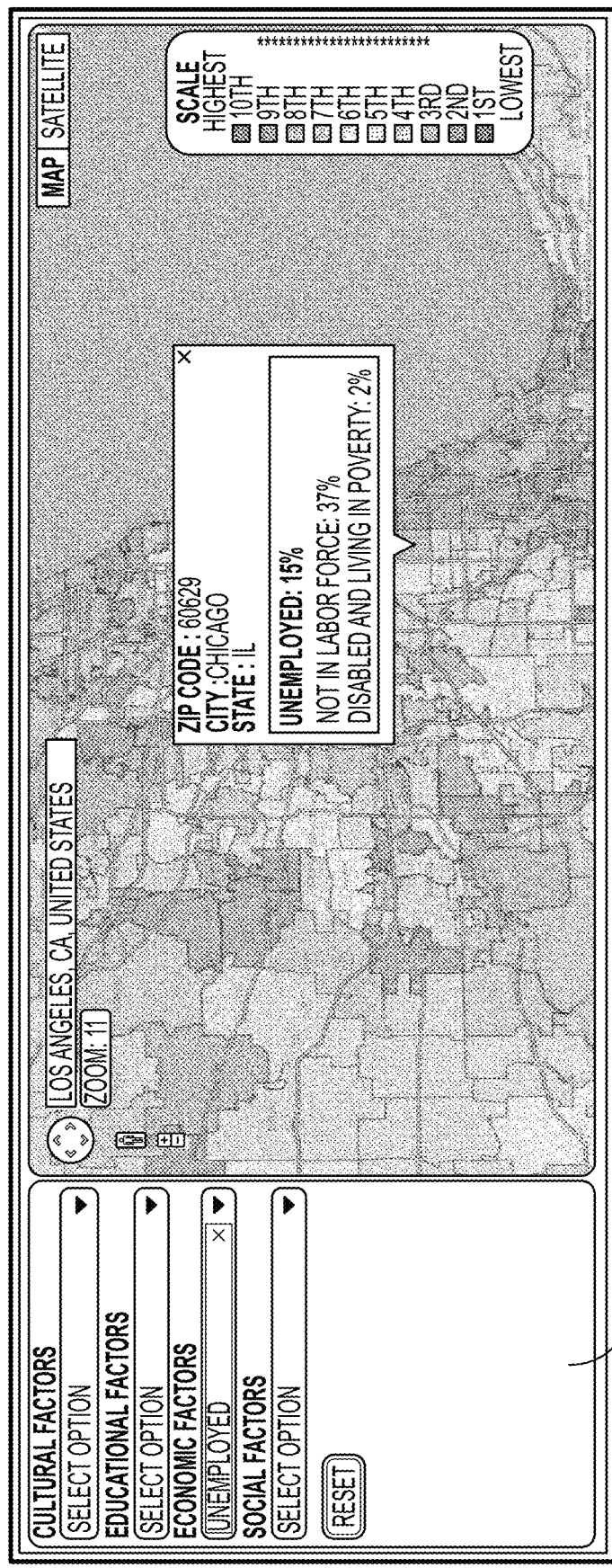
Figure 37:
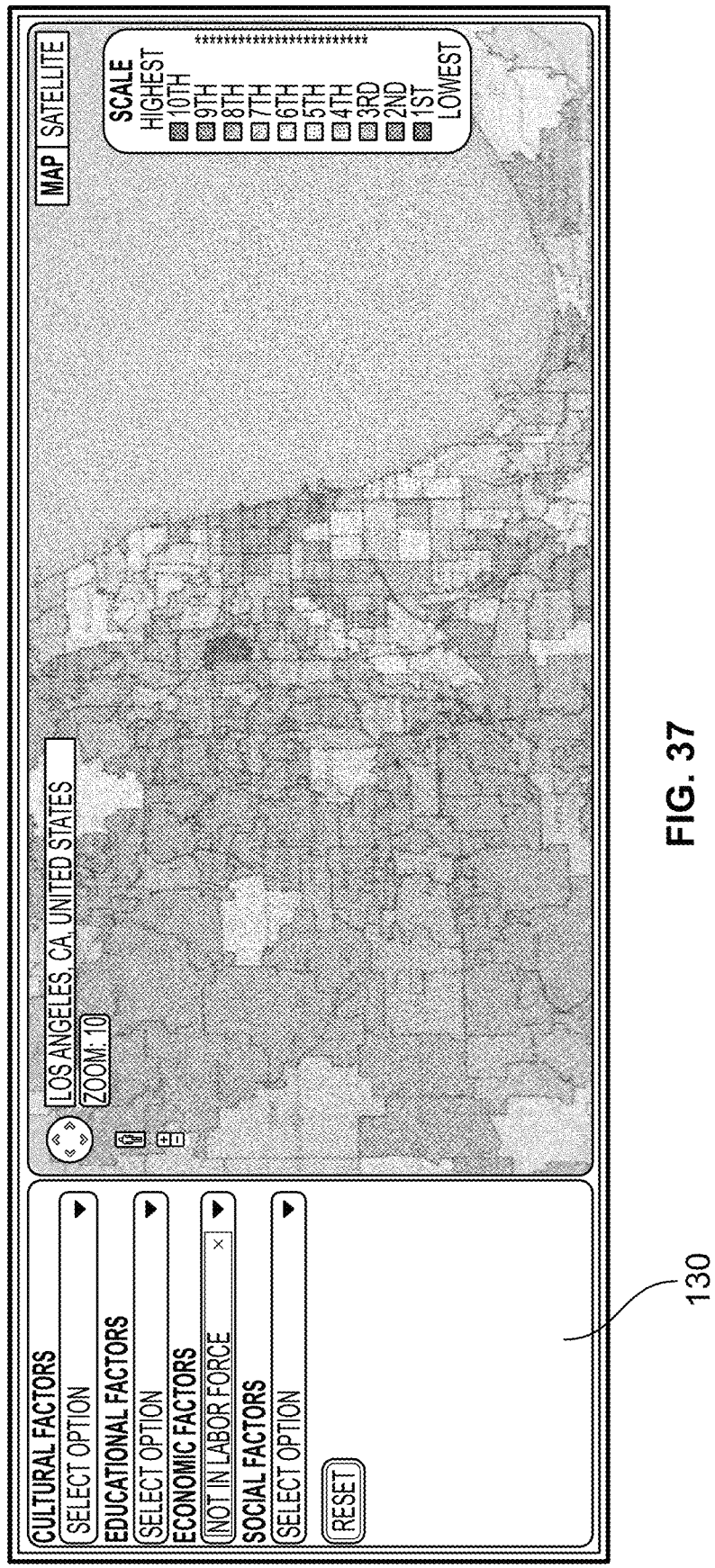
Figure 38:
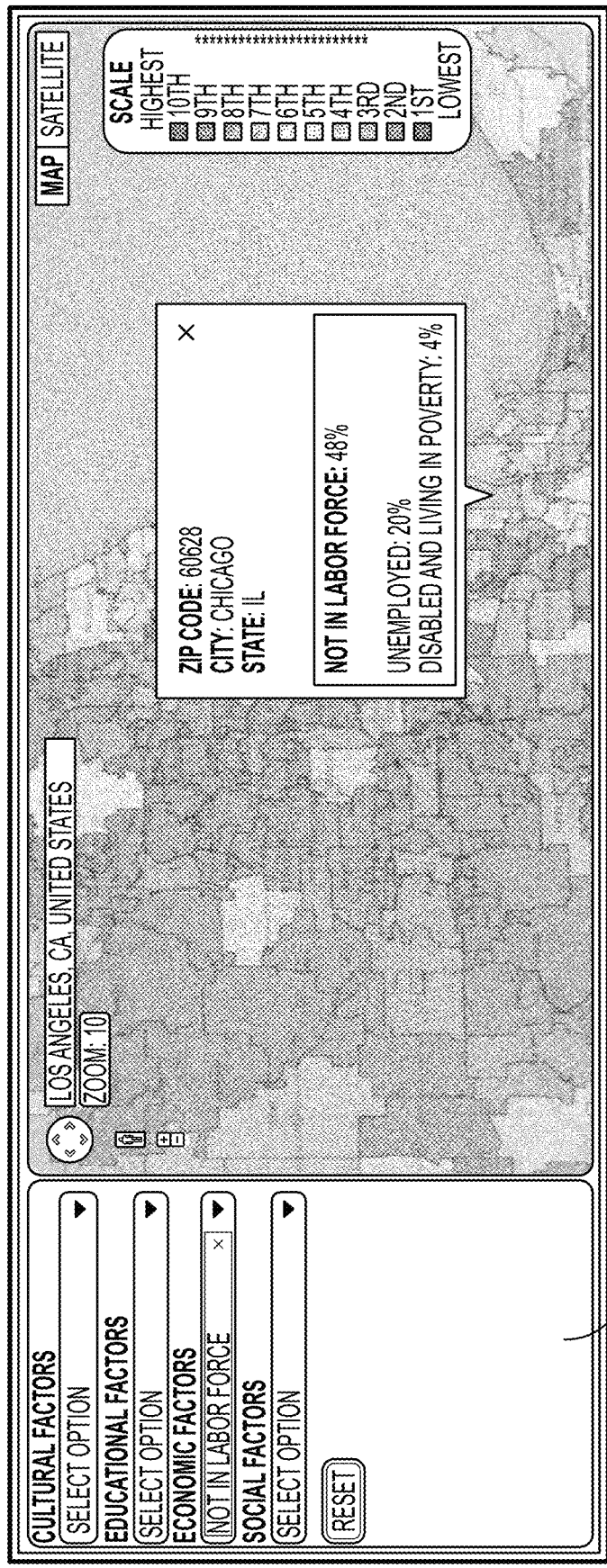
Figure 39:
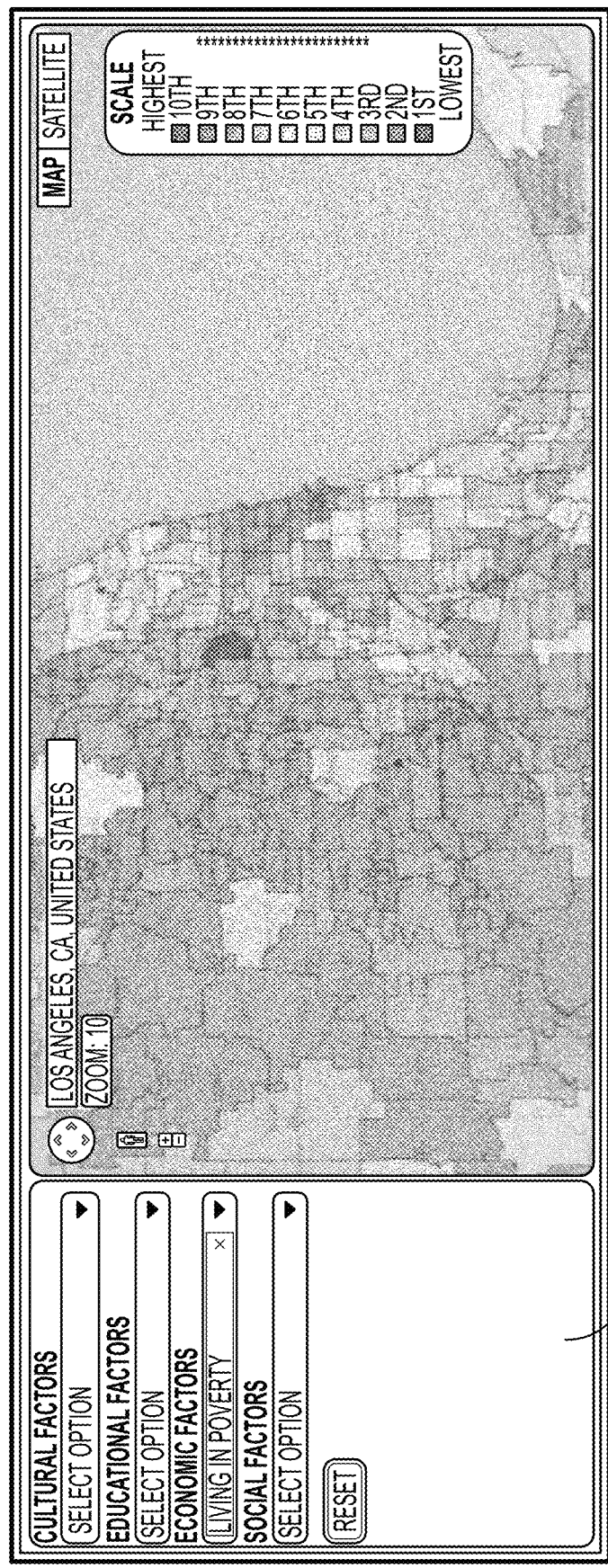
Figure 40:
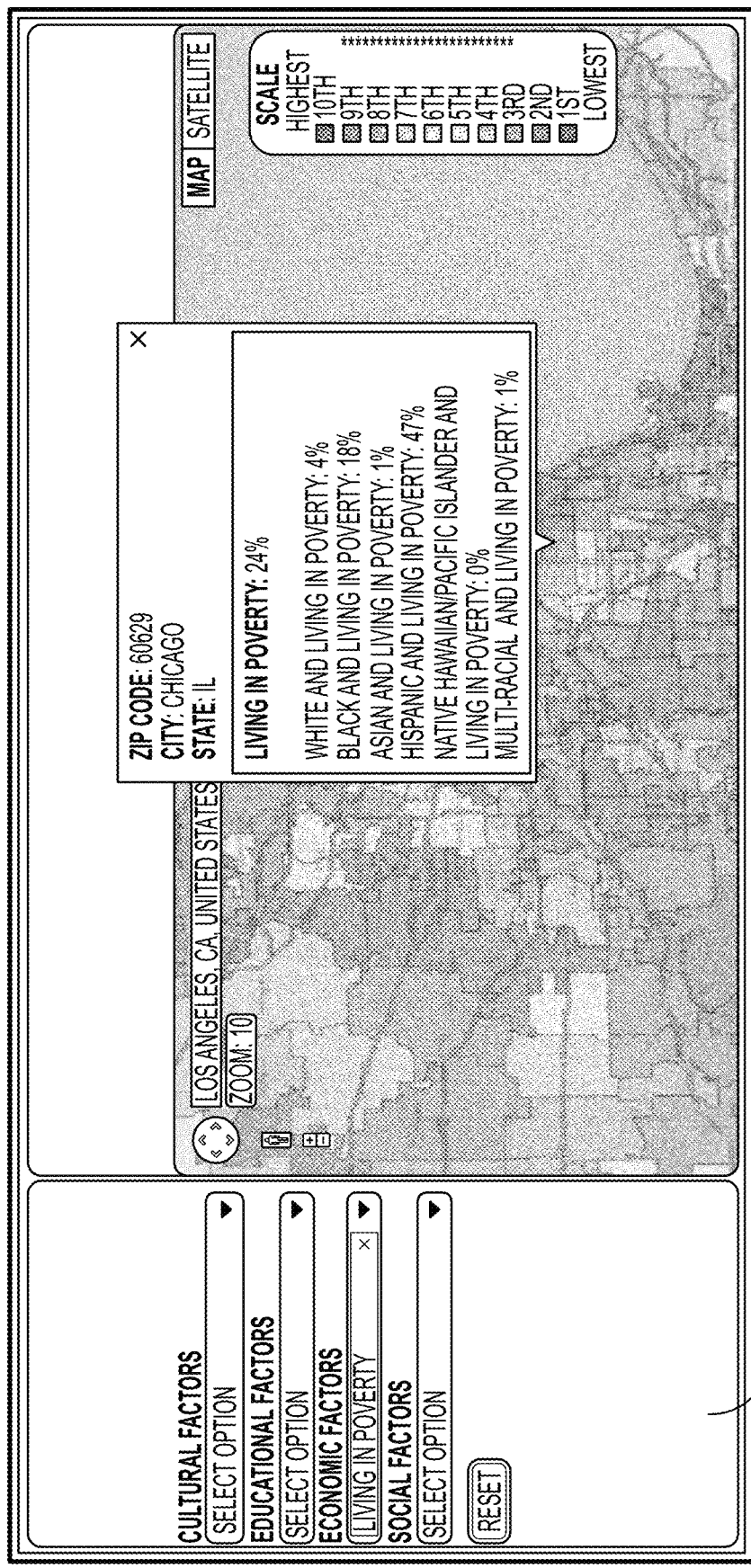
Figure 41:
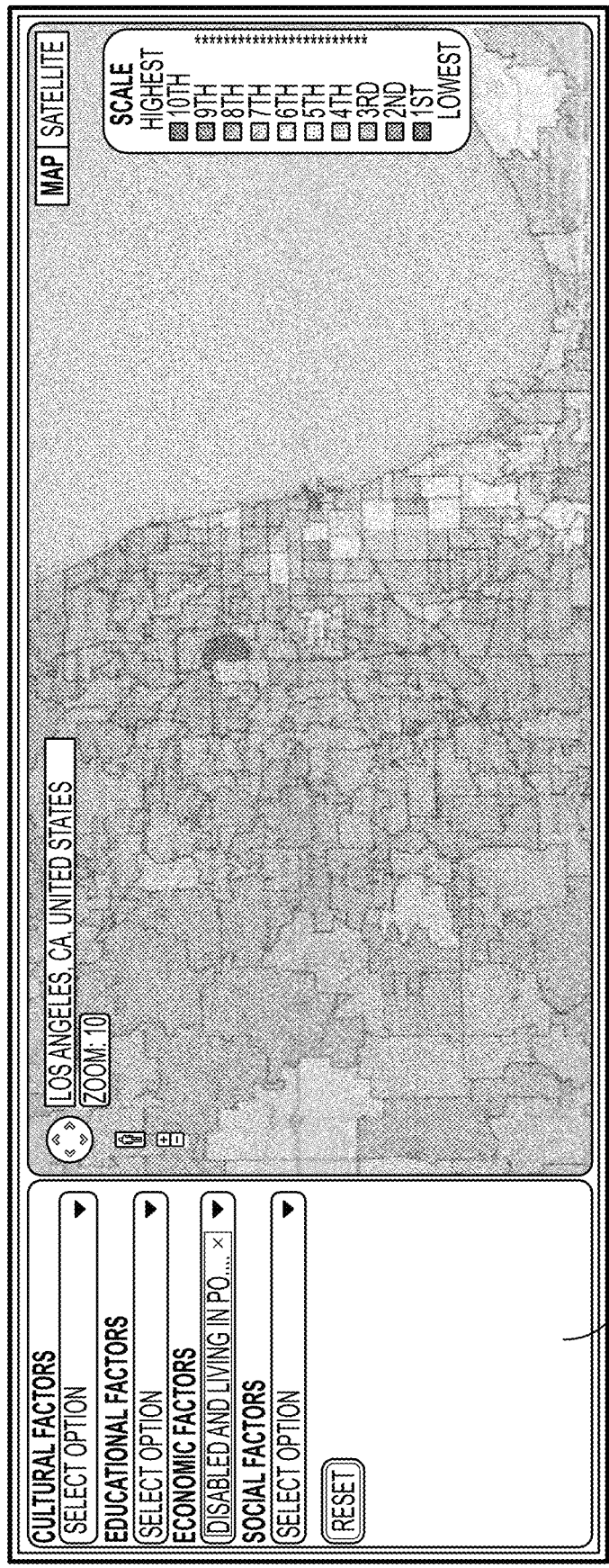
Figure 42:
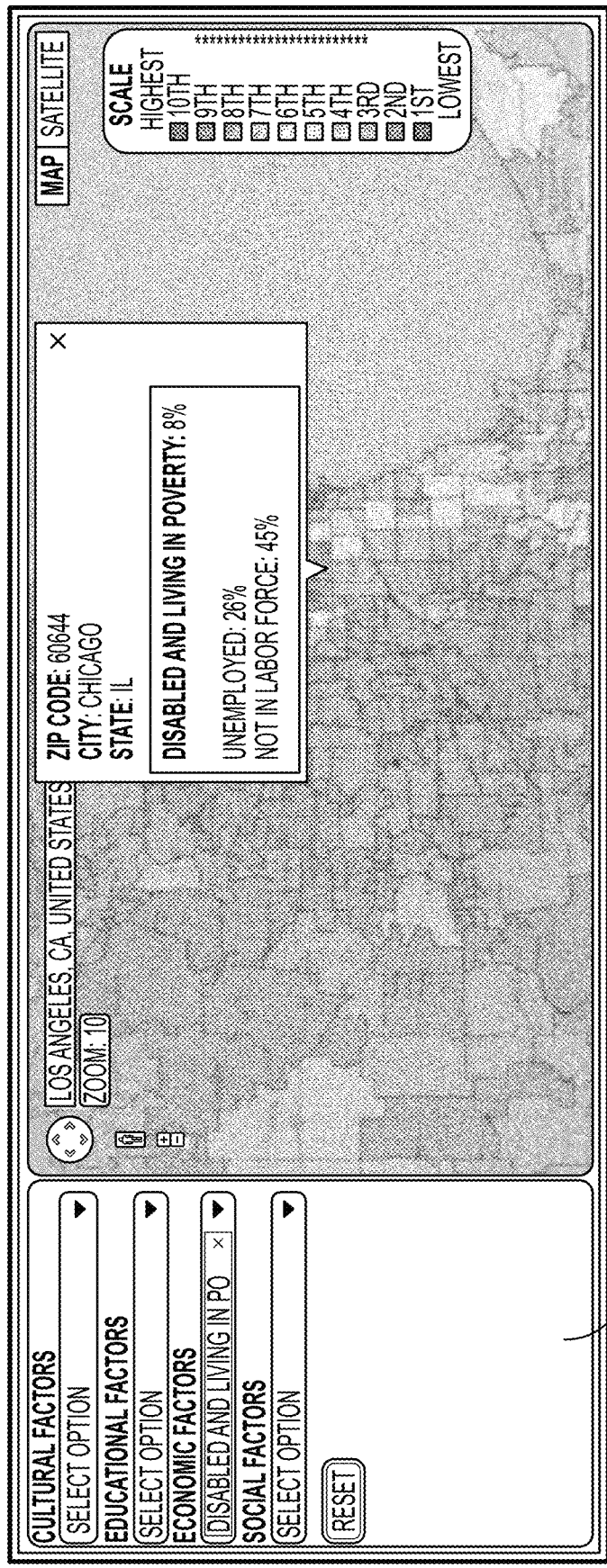

FIGS. 35-36 show representative economic factor data associated with the rate of unemployment in a selected geographic location. FIGS. 37-38 show representative economic factor data associated with the prevalence and/or proportion of people not in the labor force in a selected geographic location. FIGS. 39-40 show representative economic factor data associated with the prevalence of families living in poverty in a selected geographic location. In one embodiment, poverty is defined by the US Census Bureau as money income, before taxes, relative to family size and composition and do not vary geographically. FIGS. 41-42 show representative economic factor data associated with the prevalence and/or proportion of disabled people who are living in poverty in a selected geographic location. This layer may identify the relationship between disability and poverty and the impact of the foregoing on health.

Figure 43:
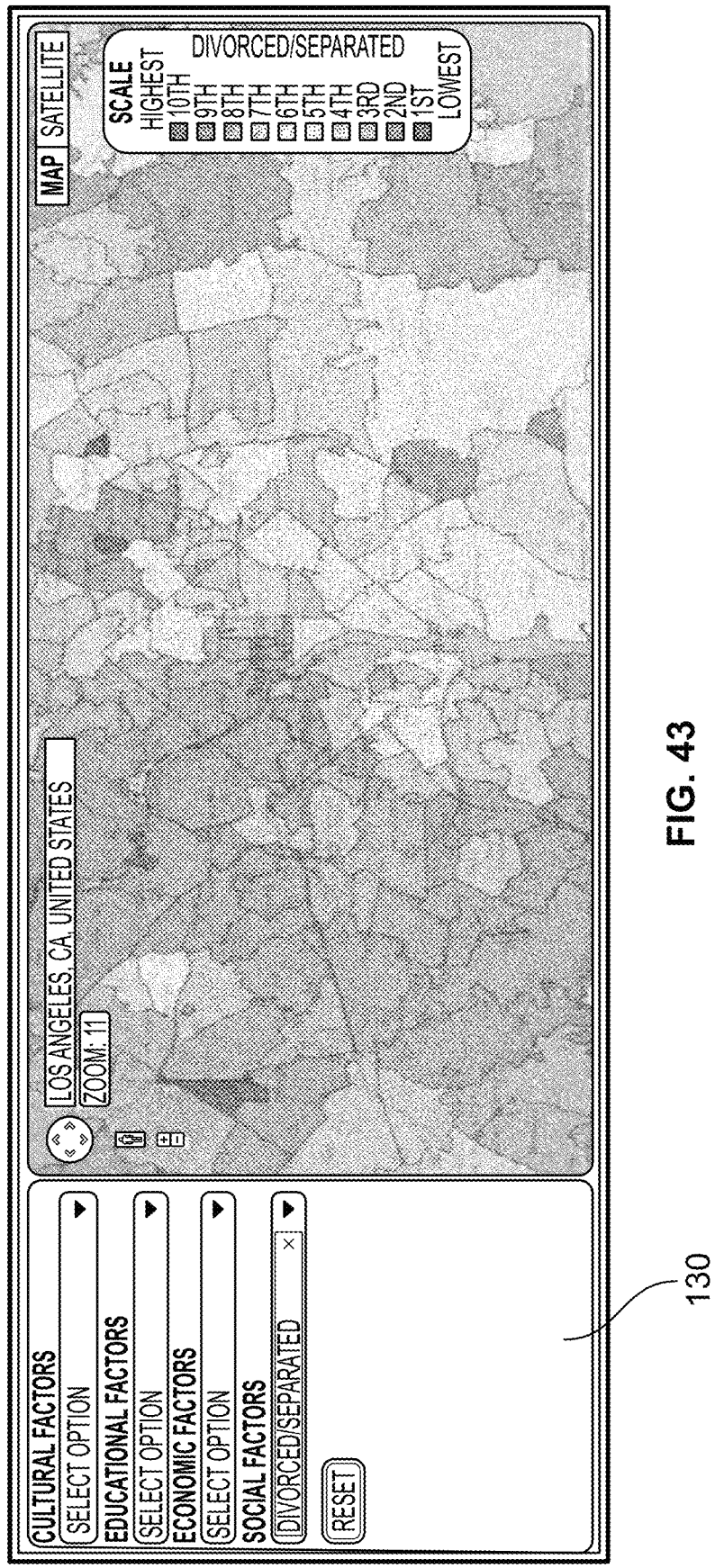
Figure 44:
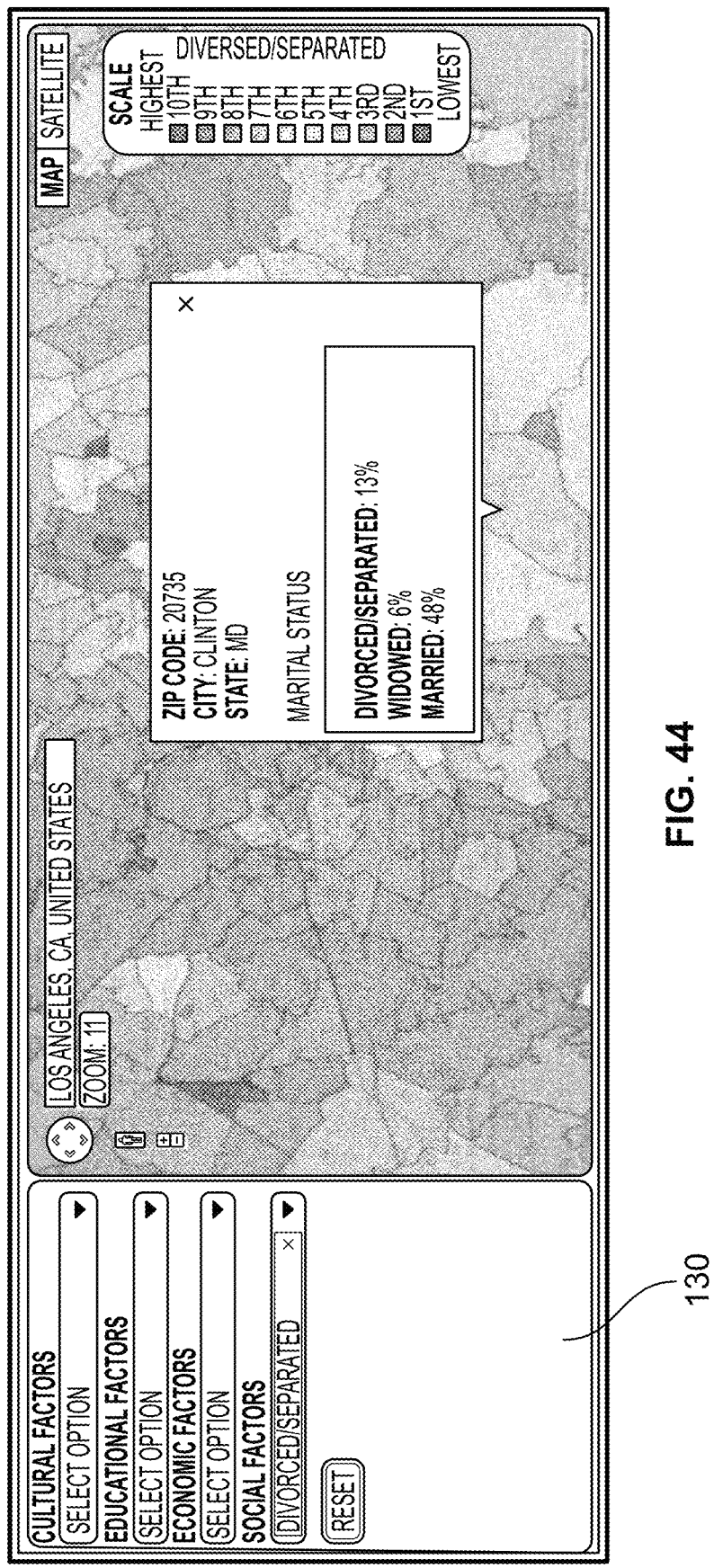
Figure 45:
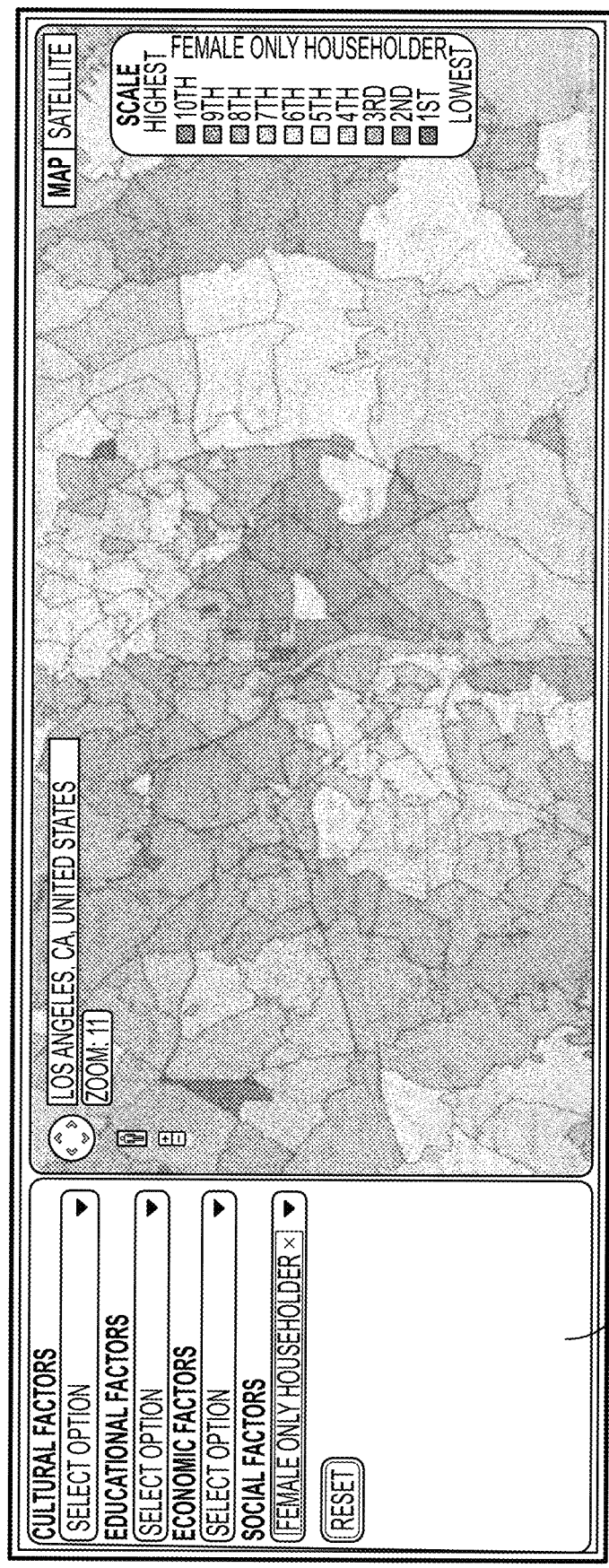
Figure 46:
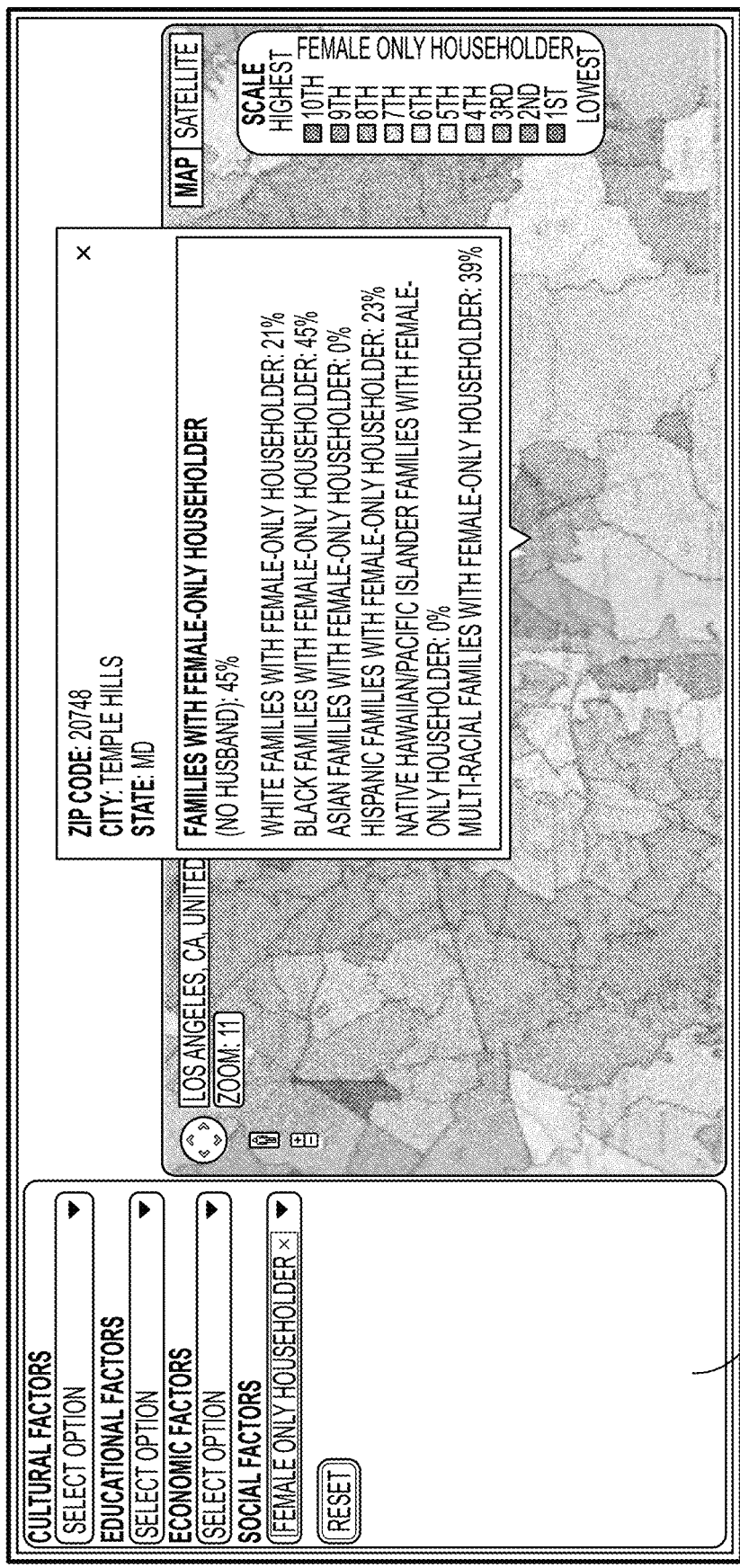
Figure 47:
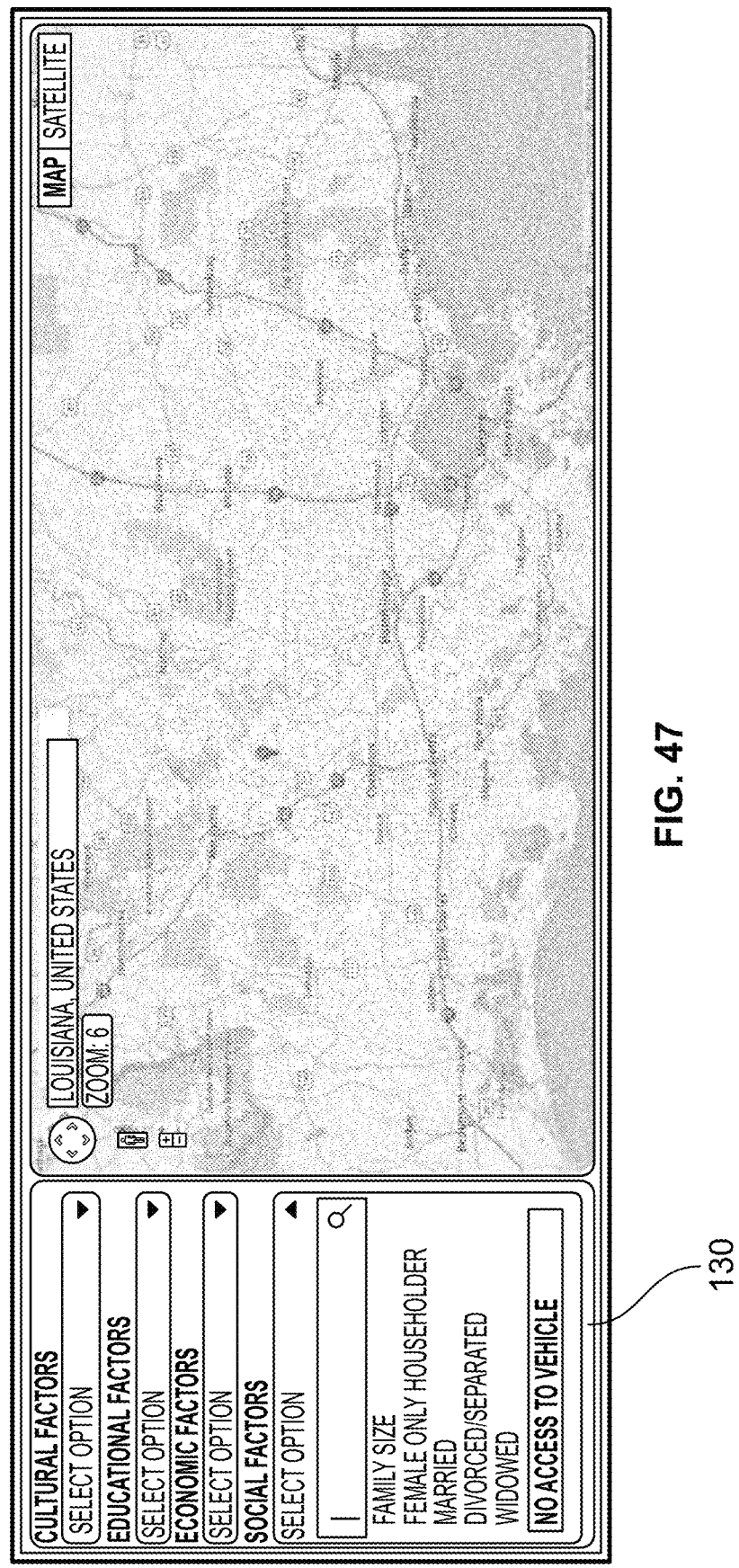
Figure 48:
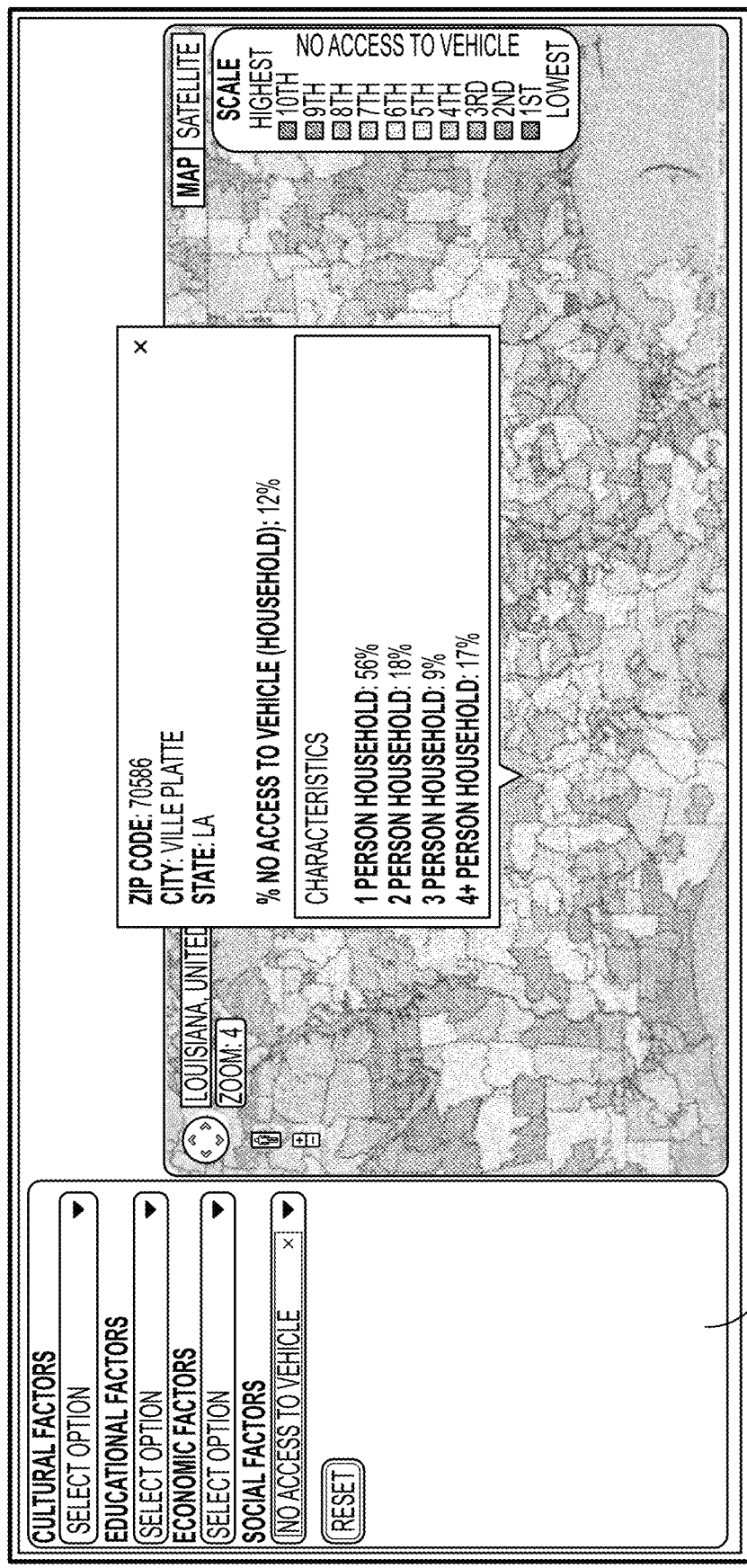
Figure 49:
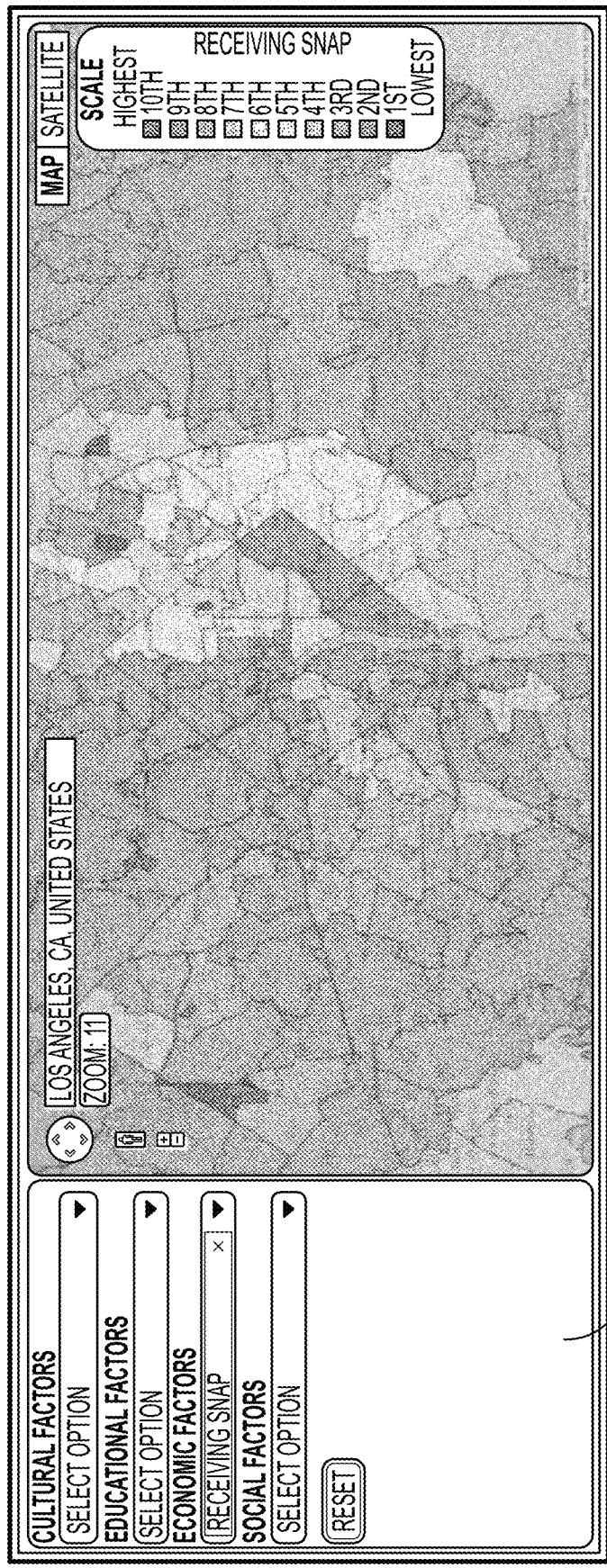
Figure 50:
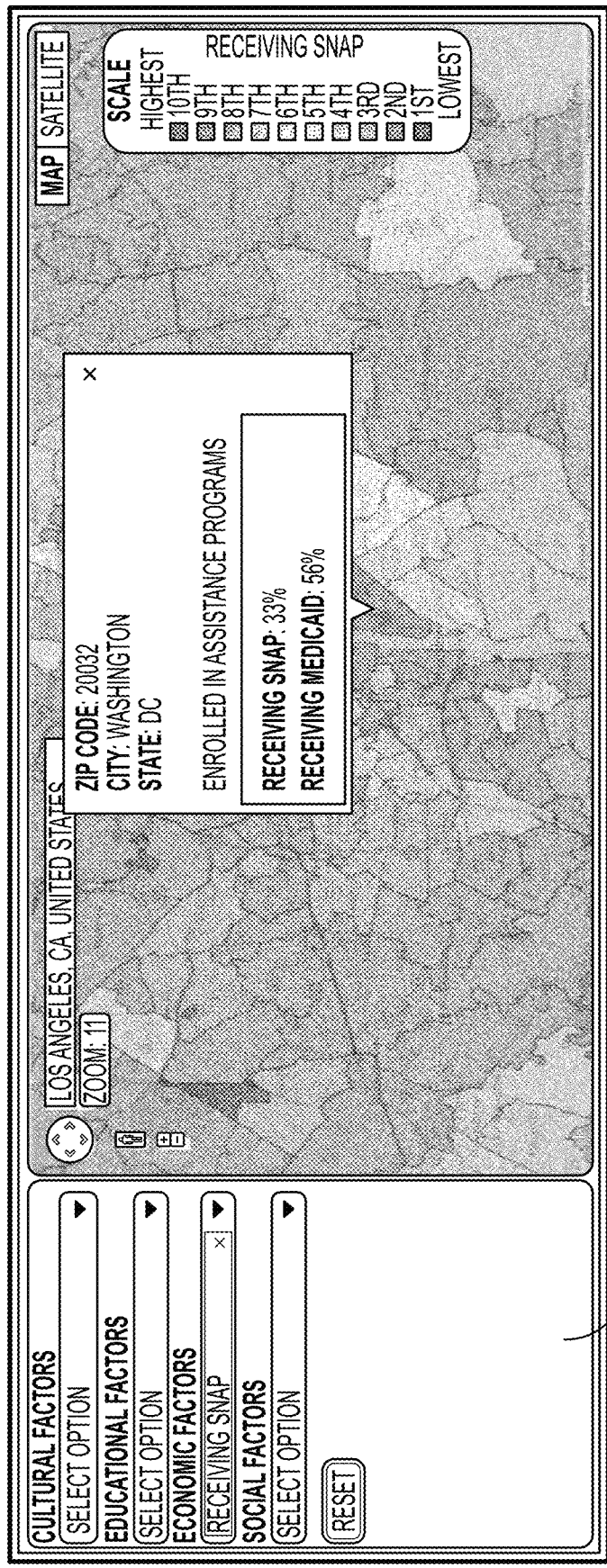
Figure 51:
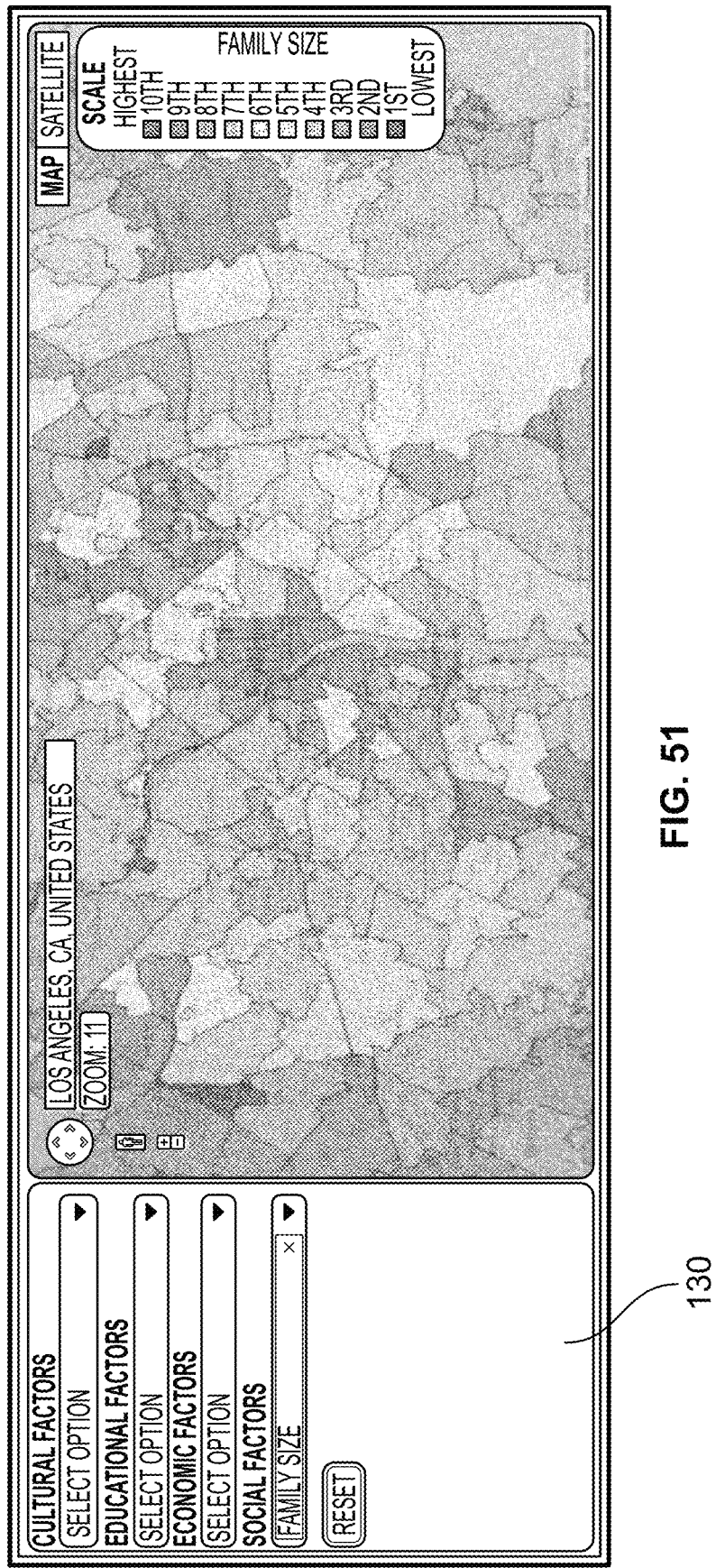
Figure 52:
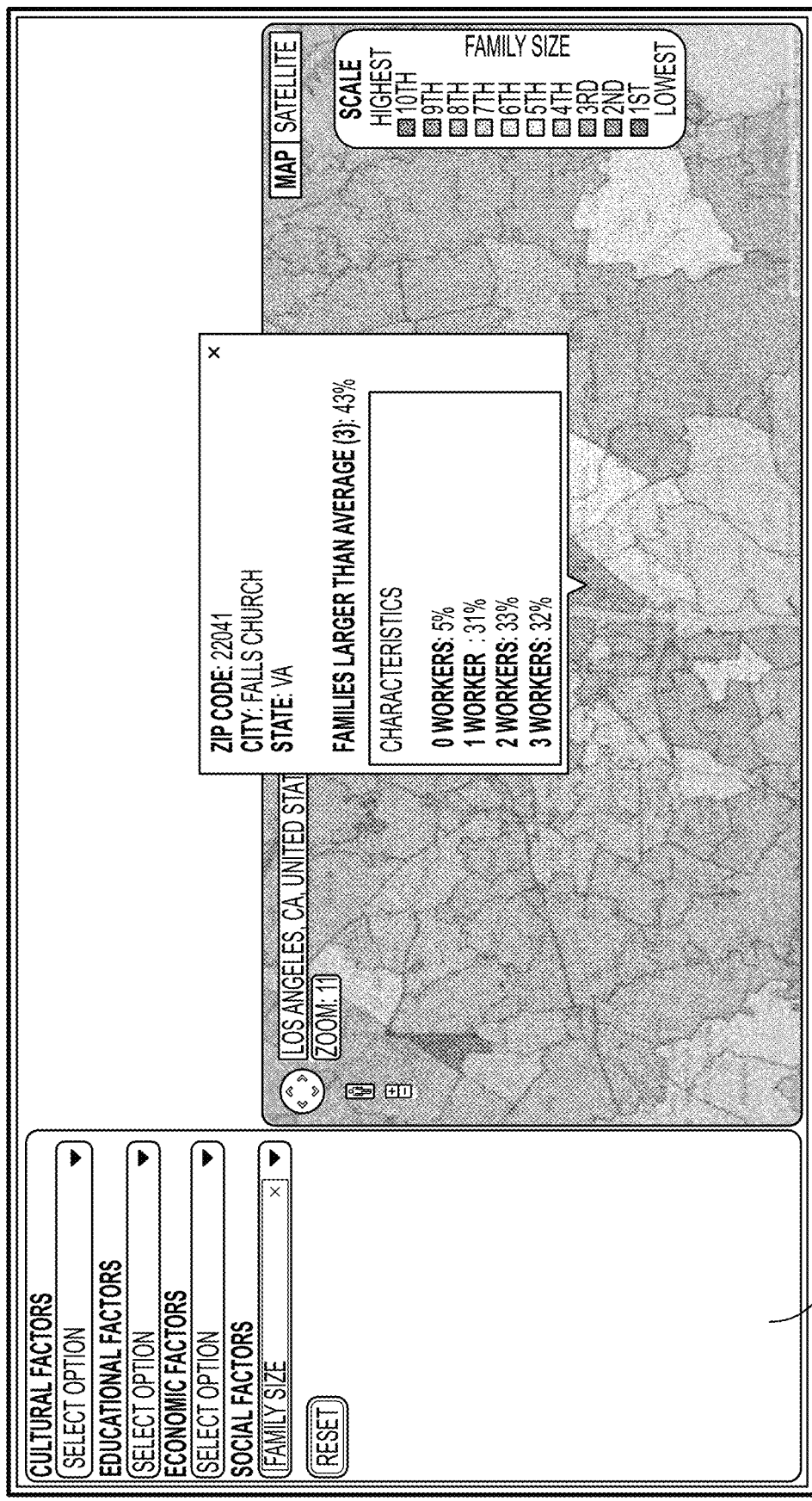

FIGS. 43-44 show representative social factor data associated with the prevalence and/or proportion of people of a specific marital status, such as divorced, separated, widowed, and married, in a selected geographic location. FIGS. 45-46 show representative social factor data associated with the prevalence and/or proportion of families having a female as the householder in a selected geographic location. In one embodiment, a family household contains at least 2 persons—the householder and at least one other person related to the householder by birth, marriage, or adoption. FIG. 46 shows representative detailed social factor data for female as the householder together with the distribution by race/ethnic groups. FIGS. 47-48 show representative social factor data associated with the prevalence and/or proportion of people without access to a vehicle in a selected geographic location. FIGS. 49-50 show representative economic factor data associated with the proportion of the population enrolled in Supplemental Nutritional Assistance Program (SNAP) in a selected geographic location. FIGS. 51-52 show representative social factor data associated with the prevalence and/or proportion of families exceeding the average family size in a selected geographic location.

To display one or more of the images described above in graphical user interface (GUI) 101, system 110 may be configured as one or more layers positioned on top of the reference map powered by the external server (e.g., Google®). Any of the community mapping factors or social determinants of health factors described above may be combined with one another to express or filter the data in any one of a number of ways. The resulting image tiles, raster files, and/or shapefiles may be stored/saved for future recall to avoid having to retrace one's steps to arrive at the same window sizing and selection of factors and location. Any of the resulting images may be captured, bookmarked, and or transmitted to another user via email, chat, or any other connectivity tool.

One or more aspects of server system 110 are operable by one or more computers and/or one or more programmable logic controllers (PLC's). The computers and/or PLC's may be connected to one another and to other computers or devices via a wired or wireless network. These devices may be connected to one or more remote computers and/or web servers via a wired or wireless connection to the Internet.

The computers and one or more PLC's include a processor, such as a central processing unit (CPU), for executing software, particularly software stored in memory or on any computer readable medium, for use by or in connection with any computer related system or method.

A computer readable medium includes any electronic, magnetic, optical, or other physical device or apparatus that can contain or store a computer program for use by or in connection with a computer related system or method. Memory can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, memory may incorporate electronic, magnetic, optical, and/or other types of storage media. Memory can have a distributed architecture where various components are situated remote from one another, but are still accessed by a processor.

The software may include one or more separate programs comprising ordered listings of executable instructions for implementing logical functions. The software stored in memory or on any computer readable medium may include one or more computer programs, each including executable instructions executed by the processor. An operating system may control the execution of other computer programs and can provide scheduling, input-output control, file and data management, memory management, and communication control and related services.

In one embodiment, the PLC may include a computer processor such as a central processing unit (CPU), memory, operating software stored in memory, and various input and output (I/O) devices or data paths. The I/O devices may include input devices, such as a keyboard, mouse, touch screen, and/or any other user interface. The I/O devices may also include output devices, such as a computer display, a modem, a router, serial and parallel wired and wireless communication components and any other elements needed to connect to, for example, another computer or device via a local network or the Internet whether wired or wirelessly.

While specific embodiments have been described in detail, it will be appreciated by those skilled in the art that various modifications and alternatives to those details could be developed in light of the overall teachings of the disclosure. Accordingly, the disclosure herein is meant to be illustrative only and not limiting as to its scope and should be given the full breadth of the appended claims and any equivalents thereof.

What is claimed is:

1. A geographic-based population information system, comprising:
one or more servers configured to:
receive, from a web browser, a request for a desired segmenting granularity of a geographical area, the desired segmenting granularity corresponding with a center of the geographical area and a zoom level, the geographical area including geographic segments at the desired segmenting granularity;
retrieve shapefiles based on the geographical area and the desired segmenting granularity, the shapefiles defining static geographic boundaries of the geographic segments at the desired segmenting granularity;
retrieve population data corresponding to each of the geographic segments within the geographical area from one or more databases;
generate symbolization instructions for the geographic segments of the geographical area based on the population data;
produce image tiles for the geographic segments of the geographical area, wherein each of the image tiles corresponds to a set of the static geographic boundaries that is filled based on a respective set of the symbolization instructions; and
serve the image tiles to the web browser for overlay onto the geographical area.

2. The system of claim 1, wherein the symbolization instructions include color or shading instructions.

3. The system of claim 1, wherein the one or more servers are configured to receive, from the web browser, user selections for the center and the zoom level of the desired segmenting granularity of the geographical area.

4. The system of claim 3, wherein the one or more servers are configured to receive the user selection for the zoom level from a list including a city level, a zip code level, and a county level.

5. The system of claim 3, wherein the one or more servers are configured to retrieve updated sets of the shapefiles and the population data in response to identifying a change in the user selections of at least one of the center or the zoom level.

6. The system of claim 1, wherein one or more of the shapefiles retrieved by the one or more servers includes a polygon with vertices having coordinates that define one or more of the static geographic boundaries at the desired segmenting granularity of the geographical area.

7. The system of claim 1, wherein the one or more servers are further configured to include tile-arrangement instructions for arranging the image tiles onto the geographical area.

8. A geographic-based community information system, comprising:
one or more servers configured to:
receive, from a web browser, a request for a desired segmenting granularity of a geographical area, the desired segmenting granularity corresponding with a center of the geographical area and a zoom level, the geographical area including geographic segments at the desired segmenting granularity;
retrieve shapefiles based on the geographical area and the desired segmenting granularity, the shapefiles defining static geographic boundaries of the geographic segments at the desired segmenting granularity;
retrieve community mapping data corresponding to each of the geographic segments within the geographical area from one or more databases;
generate symbolization instructions for the geographic segments of the geographical area based on the community mapping data;
produce image tiles for the geographic segments of the geographical area, wherein each of the image tiles corresponds to a set of the static geographic boundaries that is filled based on a respective set of the symbolization instructions; and
serve the image tiles to the web browser for overlay onto the geographical area.

9. The system of claim 8, wherein the symbolization instructions include color or shading instructions.

10. The system of claim 8, wherein the one or more servers are configured to receive, from the web browser, user selections for the center and the zoom level of the desired segmenting granularity of the geographical area.

11. The system of claim 10, wherein the one or more servers are configured to receive the user selection for the zoom level from a list including a city level, a zip code level, and a county level.

12. The system of claim 10, wherein the one or more servers are configured to retrieve updated sets of the shapefiles and the community mapping data in response to identifying a change in the user selections of at least one of the center or the zoom level.

13. The system of claim 8, wherein one or more of the shapefiles retrieved by the one or more servers includes a polygon with vertices having coordinates that define one or more of the static geographic boundaries at the desired segmenting granularity of the geographical area.

14. The system of claim 8, wherein the one or more servers are further configured to include tile-arrangement instructions for arranging the image tiles onto the geographical area.

15. A geographic-based socio-health information system, comprising:
one or more servers configured to:
receive, from a web browser, a request for a desired segmenting granularity of a geographical area, the desired segmenting granularity corresponding with a center of the geographical area and a zoom level, the geographical area including geographic segments at the desired segmenting granularity;
retrieve shapefiles based on the geographical area and the desired segmenting granularity, the shapefiles defining static geographic boundaries of the geographic segments at the desired segmenting granularity;
retrieve social determinants of health data corresponding to each of the geographic segments within the geographical area from one or more databases;
generate symbolization instructions for the geographic segments of the geographical area based on the social determinants of health data;
produce image tiles for the geographic segments of the geographical area, wherein each of the image tiles corresponds to a set of the static geographic boundaries that is filled based on a respective set of the symbolization instructions; and
serve the image tiles to the web browser for overlay onto the geographical area.

16. The system of claim 15, wherein the symbolization instructions include color or shading instructions.

17. The system of claim 15, wherein the one or more servers are configured to receive, from the web browser, user selections for the center and the zoom level of the desired segmenting granularity of the geographical area.

18. The system of claim 17, wherein the one or more servers are configured to retrieve updated sets of the shapefiles and the social determinants of health data in response to identifying a change in the user selections of at least one of the center or the zoom level.

19. The system of claim 15, wherein one or more of the shapefiles retrieved by the one or more servers includes a polygon with vertices having coordinates that define one or more of the static geographic boundaries at the desired segmenting granularity of the geographical area.

20. The system of claim 15, wherein the one or more servers are further configured to include tile-arrangement instructions for arranging the image tiles onto the geographical area.

* * * * *